United States Patent
Steeneck et al.

(10) Patent No.: US 10,981,908 B2
(45) Date of Patent: Apr. 20, 2021

(54) ARYL HYDROCARBON RECEPTOR (AHR) MODULATOR COMPOUNDS

(71) Applicant: PHENEX PHARMACEUTICALS AG, Ludwigshafen (DE)

(72) Inventors: Christoph Steeneck, Heidelberg (DE); Ulrich Deuschle, Speyer (DE); Michael Albers, Mannheim (DE); Thomas Hoffmann, Speyer (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 0 days.

(21) Appl. No.: 16/479,130

(22) PCT Filed: Feb. 1, 2018

(86) PCT No.: PCT/EP2018/052542
§ 371 (c)(1),
(2) Date: Jul. 18, 2019

(87) PCT Pub. No.: WO2018/141857
PCT Pub. Date: Aug. 9, 2018

(65) Prior Publication Data
US 2019/0389857 A1    Dec. 26, 2019

(30) Foreign Application Priority Data
Feb. 1, 2017 (EP) .................................. 17000158

(51) Int. Cl.
*C07D 471/04* (2006.01)
(52) U.S. Cl.
CPC ................ *C07D 471/04* (2013.01)
(58) Field of Classification Search
CPC .... C07D 471/04; A61K 31/437; A61K 45/06; A61K 35/00
See application file for complete search history.

(56) References Cited

U.S. PATENT DOCUMENTS

| | | | |
|---|---|---|---|
| 8,901,118 B2 | 12/2014 | Zhang et al. | |
| 9,102,672 B2* | 8/2015 | Hadida-Ruah | ............ A61P 5/00 |
| 9,676,748 B2 | 6/2017 | Wu et al. | |
| 2004/0180946 A1 | 9/2004 | Sircar et al. | |
| 2012/0295904 A1 | 11/2012 | Zhi et al. | |
| 2013/0338201 A1 | 12/2013 | Song | |
| 2016/0175278 A1 | 6/2016 | Sherr et al. | |
| 2020/0031805 A1 | 1/2020 | Deuschle et al. | |

FOREIGN PATENT DOCUMENTS

| | | |
|---|---|---|
| WO | 92/02500 A1 | 2/1992 |
| WO | 98/22457 A1 | 5/1998 |
| WO | 2005/005414 A2 | 1/2005 |
| WO | 2007/057329 A1 | 5/2007 |
| WO | 2011/097079 A1 | 8/2011 |
| WO | 2011/117264 A1 | 9/2011 |
| WO | 2011/133637 A2 | 10/2011 |
| WO | 2012/123745 A1 | 9/2012 |
| WO | 2014/060328 A1 | 4/2014 |
| WO | 2014/100620 A2 | 6/2014 |
| WO | 2018/141855 A1 | 8/2018 |
| WO | 2018/141857 A1 | 8/2018 |
| WO | 2018/153893 A1 | 8/2018 |

OTHER PUBLICATIONS

Vezina, Biochem Pharm, vol. 77, 566-576, 2009. (Year: 2009).*
Monteleone, Gastroenterology, vol. 28 (4), 310-313, 2012. (Year: 2012).*
Kerkvliet, Biochem Pharm, vol. 77, 2009, 746-760. (Year: 2009).*
U.S. Appl. No. 16/479,847, filed Jul. 22, 2019, Steeneck et al.
U.S. Appl. No. 16/483,981, filed Aug. 6, 2019, Deuschle et al.
Bessede et al., "Aryl hydrocarbon receptor control of a disease tolerance defence pathway," *Nature* 511: 184-190, 2014 (19 pages).
Foster, "Deuterium isotope effects in studies of drug metabolism," *Trends in Pharmacological Sciences* 5: 524-527, 1984 (5 pages).
Hanan et al., "Discovery of Selective and Noncovalent Diaminopyrimidine-Based Inhibitors of Epidermal Growth Factor Receptor Containing the T790M Resistance Mutation," *J. Med. Chem.* 57: 10176-10191, 2014.
Koliopanos et al., "Increased arylhydrocarbon receptor expression offers a potential therapeutic target for pancreatic cancer," *Oncogene* 21: 6059-6070, 2002.
Li et al., "Expression of aryl hydrocarbon receptor in relation to p53 status and clinicopathological parameters in breast cancer," *Int. J. Clin. Exp. Pathol.* 7(11): 7931-7937, 2014.
Li et al., "LEADOPT: An automatic tool for structure-based lead optimization, and its application in structural optimizations of VEGFR2 and SYK inhibitors," *European Journal of Medicinal Chemistry* 93: 523-538, 2015.
Murray et al., "AH Receptor Ligands in Cancer: Friend and Foe," *Nat. Rev. Cancer* 14(12): 801-814, 2014.
Naud et al., "Structure-Based Design of Orally Bioavailable 1H-Pyrrolo[3,2-c]pyridine Inhibitors of Mitotic Kinase Monopolar Spindle 1 (MPS1)," *J. Med. Chem.* 56: 10045-10065, 2013.

(Continued)

Primary Examiner — D Margaret M Seaman
(74) Attorney, Agent, or Firm — Seed IP Law Group LLP

(57) ABSTRACT

The present invention relates to compounds which can act as aryl hydrocarbon receptor (AhR) modulators and, in particular, as AhR antagonists. The invention further relates to the use of the compounds for the treatment and/or prophylaxis of diseases and/or conditions through binding of said aryl hydrocarbon receptor by said compounds.

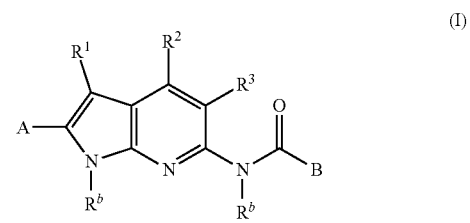

(I)

18 Claims, No Drawings

(56) References Cited

OTHER PUBLICATIONS

Richmond et al., "The Aryl Hydrocarbon Receptor Is Constitutively Active in Advanced Prostate Cancer Cells," *PLOS One* 9(4): e95058, 2014 (11 pages).

Romani et al., "Microbiota control of a tryptophan-AhR pathway in disease tolerance to fungi," *Eur. J. Immunol.* 44: 3192-3200, 2014.

Safe et al., "Role of the Aryl Hydrocarbon Receptor in Carcinogenesis and Potential as a Drug Target," *Toxicological Sciences* 135(1): 1-16, 2013.

Zelante et al., "Tryptophan Catabolites from Microbiota Engage Aryl Hydrocarbon Receptor and Balance Mucosal Reactivity via Interleukin-22," *Immunity* 39: 372-385, 2013.

Official Action from European Patent Office re extended European search report, dated Mar. 22, 2017, for Patent Application No. 17000157.2, 10 pages.

Official Action from European Patent Office re extended European search report, dated Mar. 23, 2017, for Patent Application No. 17000158.0, 4 pages.

Official Action from European Patent Office re extended European search report, dated Mar. 30, 2017, for Patent Application No. 17000276.0, 5 pages.

International Search Report, dated Mar. 12, 2018, for International Application No. PCT/EP2018/052542, 4 pages.

International Search Report, dated Mar. 29, 2018, for International Application No. PCT/EP2018/052538, 5 pages.

International Search Report, dated May 3, 2018, for International Application No. PCT/EP2018/054234, 5 pages.

Official Action from Intellectual Property India dated Mar. 17, 2020, for Application No. 201917029340, 6 pages.

Official Action from Chile Ministerio de Economia dated Jul. 13, 2020, for Application No. 201902108 filed Feb. 1, 2018, 12 pages.

Official Action from Intellectual Property India dated Sep. 11, 2020, for Application No. 201917029343, 5 pages.

Official Action from Japan Patent Office dated Sep. 15, 2020, for Application No. 2019-561370, 3 pages (translation).

\* cited by examiner

ARYL HYDROCARBON RECEPTOR (AHR) MODULATOR COMPOUNDS

The present invention relates to compounds which can act as aryl hydrocarbon receptor (AhR) modulators and, in particular, as AhR antagonists. The invention further relates to the use of the compounds for the treatment and/or prophylaxis of diseases and/or conditions through binding of said aryl hydrocarbon receptor by said compounds.

The aryl hydrocarbon receptor (AhR) is a ligand-modulated transcription factor, belonging to the basic helix-loop-helix PAS (Per-Amt-Sim homology domain) family, that is expressed in most tissues in mice and humans and known to mediate many of the toxicities of 2,3,7,8-Tetrachlorodibenzo-p-dioxin (TCDD) in mice. The AhR protein is localized in the cytoplasm of eukaryotic cells in complexes with HSP90 and other proteins. Binding of agonistic ligands, such as TCDD, leads to dissociation of AhR from the HSP90 containing complex, transport to the nucleus and association with its heterodimeric partner ARNT. This heterodimeric complex can bind to AhR response elements located in promoter regions of genes such as CYP1A1, CYP1B1, ALDH3A1, NQO1, UGT1A1 etc. and induces the transcription of such genes in case of very potent and efficacious AhR agonists, such as TCDD.

By regulating the expression of genes involved in xenobiotic transformation (e.g. CYP1A1), the AhR plays a significant role in the detoxification of xenobiotic substances in liver and intestine, which are prominent locations of AhR expression. This activity might be underlying some of the described chemoprevention and tumor suppression effects exerted by AhR. On the other hand, CYP1A1 is known to metabolize some pro-cancerogens, such as benzo(a)pyrene into DNA reactive intermediates leading to mutagenesis and tumor formation (Murray et al. Nat Rev Cancer. 2014 December; 14(12):801-14; Safe et al Toxicol Sci. 2013 September; 135(1):1-16).

In mouse cancer models, knock-down of AhR typically resulted in decreased proliferation and/or invasion and migration of cancer cell lines and overexpression of constitutive active AhR results in vivo in enhanced stomach and liver cancers (Safe et al Toxicol Sci. 2013 September; 135(1):1-16).

The AhR is relatively strongly expressed in intestinal epithelial tissues, lung epithelium and skin. In these tissues the AhR expression is particularly high in cells of lymphoid origin such as T-cells, Dendritic Cells, Langerhans Cells, Macrophages, Mast cells etc. One possible function in these compartments is to integrate signals from the commensal microbiomes in the intestine, the lung and the skin, which are known to produce diverse mixtures of indolic AhR modulators that are thought to balance the responses of the immune system towards the microbiome (Bessede et al., Nature. 2014 Jul. 10; 511(7508):184-90, Zelante et al. Immunity. 2013 Aug. 22; 39(2):372-85, Romani et al., Eur J Immunol. 2014 November; 44(11):3192-200).

The expression of AhR has been found to be constitutive active in advanced human prostate cancer (Richmond et al., 2014, PLoS ONE 9(4): e95058), overexpressed in breast cancer (Li et al., Int J Clin Exp Pathol. 2014 Oct. 15; 7(11):7931) and pancreas cancer (Koliopanos et al., Oncogene. 2002 Sep. 5; 21(39):6059-70). Modulation of the AhR pathway activity by small molecule modulators might be beneficial for some of these devastating diseases with very limited treatment options.

In a recently published Patent Application US 2016/0175278 by the Trustees of Boston University, novel small molecule agents characterized as AhR modulators are being claimed for inhibiting cancer cell proliferation and tumor cell invasion and metastasis.

AhR modulators and in particular modulators with primarily antagonistic activities might be useful as medicaments for the treatment of solid tumors (e.g., pancreatic cancer, prostate cancer, breast cancer, colon cancer).

The problem underlying the present invention is to provide compounds which have a AhR-antagonistic activity and can be used in the treatment and/or prophylaxis of AhR-mediated diseases.

Said problem has been solved by a compound according to the following Formula (I), an enantiomer, diastereomer, tautomer, solvate, prodrug or pharmaceutical acceptable salt thereof.

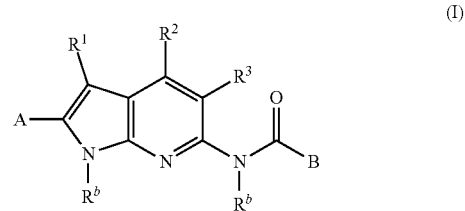

(I)

wherein
A and B are independently selected from 6- to 10-membered mono- or bicyclic aryl and 5- to 10-membered mono- or bicyclic heteroaryl containing 1 to 4 heteroatoms independently selected from N, O and S,
wherein aryl and heteroaryl are unsubstituted or substituted with 1 to 7 substituents independently selected from the group consisting of halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, NR$^a$C(O)—$C_{1-6}$-alkyl, S(O)$_2$N(R$^a$)$_2$, NR$^a$S(O)$_2$—$C_{1-3}$-alkyl and $C_{1-3}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo, or
wherein two substituents on the aryl or heteroaryl group together with the atoms they are attached to may form a 5- to 7-membered saturated or partially unsaturated carbocyclic ring or heterocyclic ring containing 1 to 3 heteroatoms independently selected from O, N and S, wherein the carbocyclic or heterocyclic is unsubstituted or substituted with 1 to 5 substituents independently selected from the group consisting of halogen, $C_{1-6}$-alkyl and halo-$C_{1-6}$-alkyl;
$R^1$, $R^2$, $R^3$ are each independently selected from hydrogen, halogen, $C_{1-3}$-alkyl, halo-$C_{1-3}$-alkyl, OH, O—$C_{1-3}$-alkyl, and CN;
$R^a$ is hydrogen or $C_{1-6}$-alkyl; and
$R^b$ is hydrogen or $C_{1-6}$-alkyl.

In another embodiment in combination with any of the above or below embodiments, $R^b$ in the compound according to Formula (I) is hydrogen.

In another embodiment in combination with any of the above or below embodiments, A in the compound according to Formula (I) is substituted with 1 to 5 substituents selected from halogen, $C_{1-6}$-alkyl, halo-$C_{1-6}$-alkyl, CN, $SO_2CH_3$, C(O)OR$^a$, C(O)N(R$^a$)$_2$ and $C_{3-6}$-cycloalkyl which is unsubstituted or substituted with $C_{1-3}$-alkyl or halo-$C_{1-3}$-alkyl.

In another embodiment in combination with any of the above or below embodiments, A in the compound according to Formula (I) is

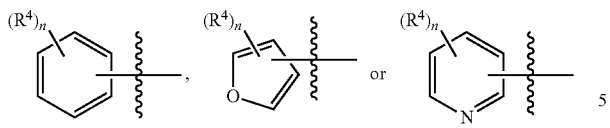 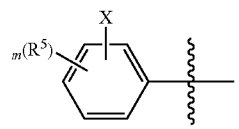

wherein
R⁴ is independently halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, NR$^a$C(O)—$C_{1-6}$-alkyl, S(O)$_2$N(R$^a$)$_2$, NR$^a$S(O)$_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo; and
n is 0 to 5.

In a more preferred embodiment in combination with any of the above or below embodiments, n is 1 to 5 and R⁴ is independently selected from halogen, $C_{1-6}$-alkyl, halo-$C_{1-6}$-alkyl, CN and $C_{3-6}$-cycloalkyl which is unsubstituted or substituted with 1 or 2 substituents independently selected from the group consisting of halogen, $C_{1-3}$-alkyl and halo-$C_{1-3}$-alkyl.

In another embodiment in combination with any of the above or below embodiments, A in the compound according to Formula (I) is

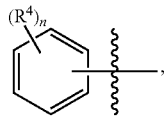

wherein
R⁴ is independently halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, NR$^a$C(O)—$C_{1-6}$-alkyl, S(O)$_2$N(R$^a$)$_2$, NR$^a$S(O)$_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo;
R$^a$ is hydrogen or $C_{1-6}$-alkyl, and
n is 0 to 5.

In another embodiment in combination with any of the above or below embodiments, A in the compound according to Formula (I) is

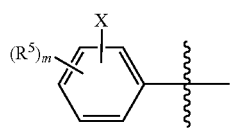

wherein
X is halogen, $C_{1-6}$-alkyl or $C_{3-6}$-cycloalkyl, wherein the alkyl and cycloalkyl are unsubstituted or substituted with 1 to 3 substituents independently selected from the group consisting of halogen, $C_{1-3}$-alkyl and halo-$C_{1-3}$-alkyl;
R⁵ is independently halogen or CN; and
m is 0 to 4.

In another embodiment in combination with any of the above or below embodiments, A in the compound according to Formula (I) is wherein X is $CH_3$, $CH_2CH_3$, $CHF_2$ or $CF_3$;
R⁵ is independently halogen or CN; and
m is 0 to 4.

In another embodiment in combination with any of the above or below embodiments, B in the compound according to Formula (I) is a 5- or 6-membered heteroaryl containing 1 to 4 heteroatoms independently selected from N, O and S, which is unsubstituted or substituted with 1 to 5 substituents independently selected from the group consisting of halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, NR$^a$C(O)—$C_{1-6}$-alkyl, S(O)$_2$N(R$^a$)$_2$, NR$^a$S(O)$_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo; and
R$^a$ is hydrogen or $C_{1-6}$-alkyl.

In another embodiment in combination with any of the above or below embodiments, B in the compound according to Formula (I) is a 5- or 6-membered heteroaryl containing 1 to 3 heteroatoms independently selected from N, O and S, which is unsubstituted or substituted with 1 to 2 substituents independently selected from the group consisting of $C_{1-6}$-alkyl, halo-$C_{1-6}$-alkyl, C(O)OR$^a$, C(O)N(R$^a$)$_2$ and $C_{3-6}$-cycloalkyl.

In another embodiment in combination with any of the above or below embodiments, B in the compound according to Formula (I) is a 9- or 10-membered heteroaryl containing 1 to 4 heteroatoms independently selected from N, O and S, which is unsubstituted or substituted with 1 to 2 substituents independently selected from the group consisting of $C_{1-6}$-alkyl, halo-$C_{1-6}$-alkyl, and $C_{3-6}$-cycloalkyl or B is a 6- or 10-membered aryl, which is unsubstituted or substituted with 1 to 2 substituents independently selected from the group consisting of halogen and $C_{1-6}$-alkyl.

In another embodiment in combination with any of the above or below embodiments, B in the compound according to Formula (I) is

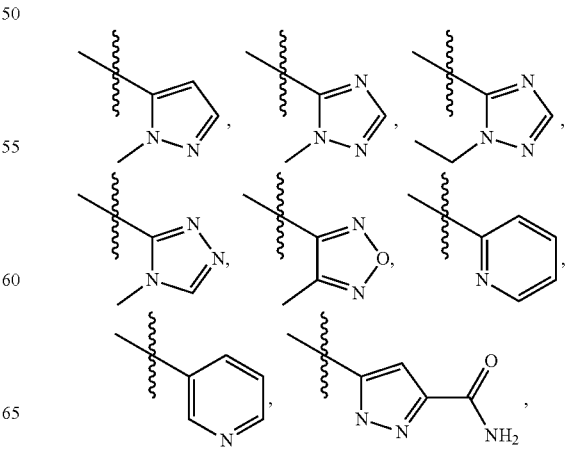

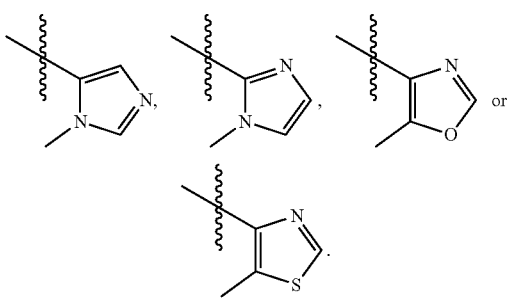

In another embodiment in combination with any of the above or below embodiments, B in the compound according to Formula (I) is

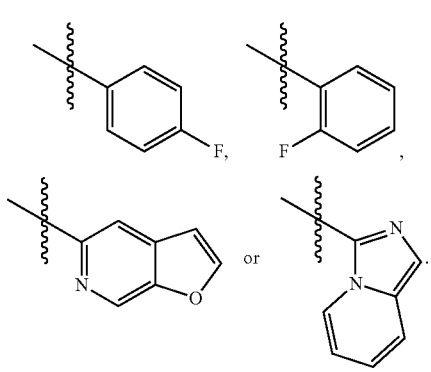

In another embodiment in combination with any of the above or below embodiments, each of $R^1$, $R^2$, $R^3$ in the compound according to Formula (I) are hydrogen.

In another embodiment in combination with any of the above or below embodiments, the compound according to Formula (I) is selected from

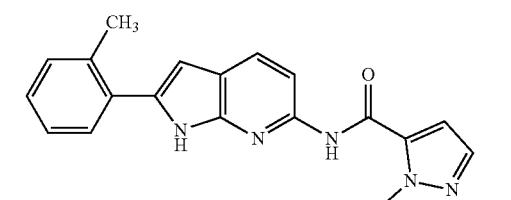

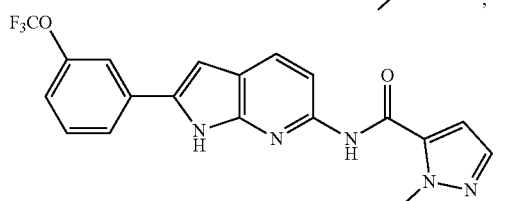

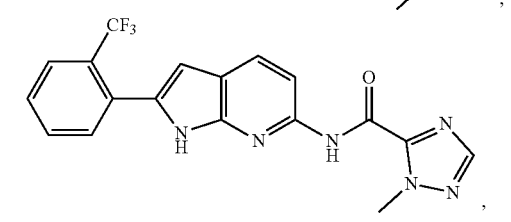

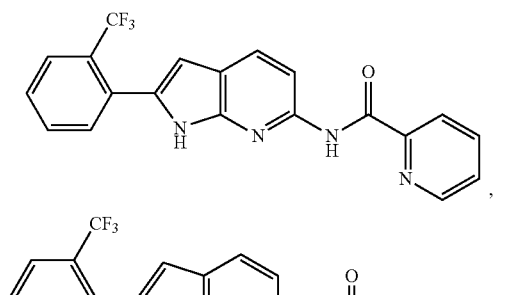

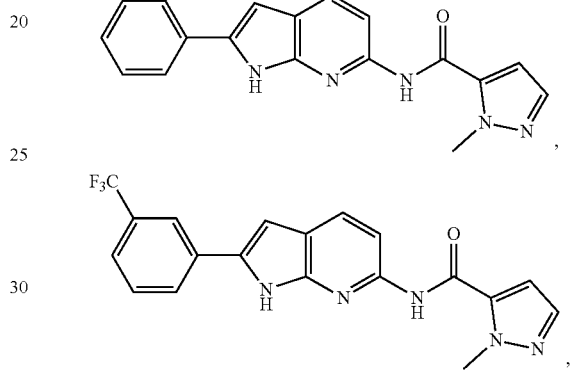

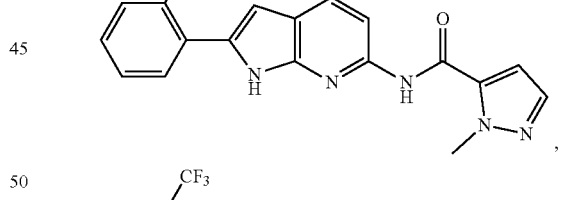

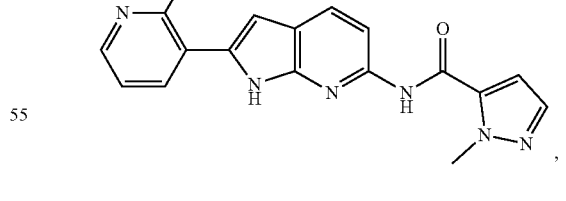

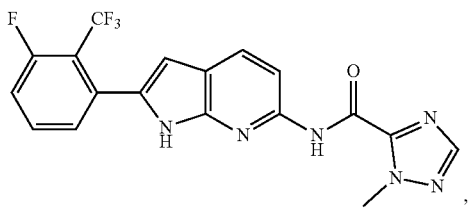

-continued
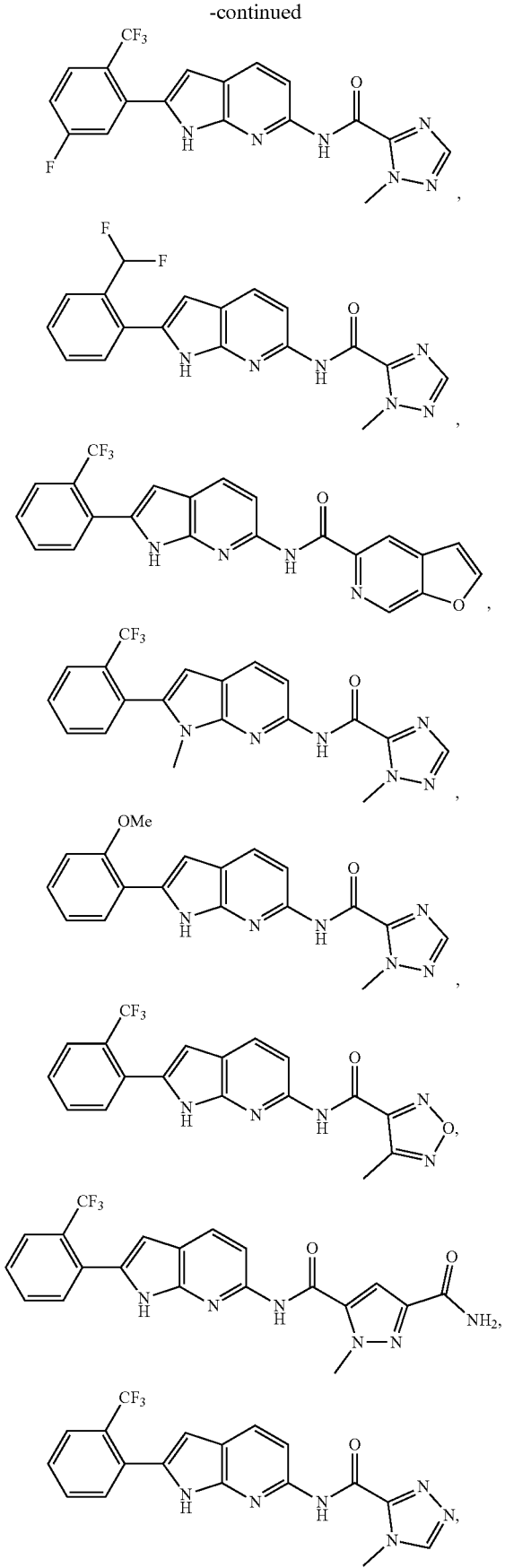
-continued
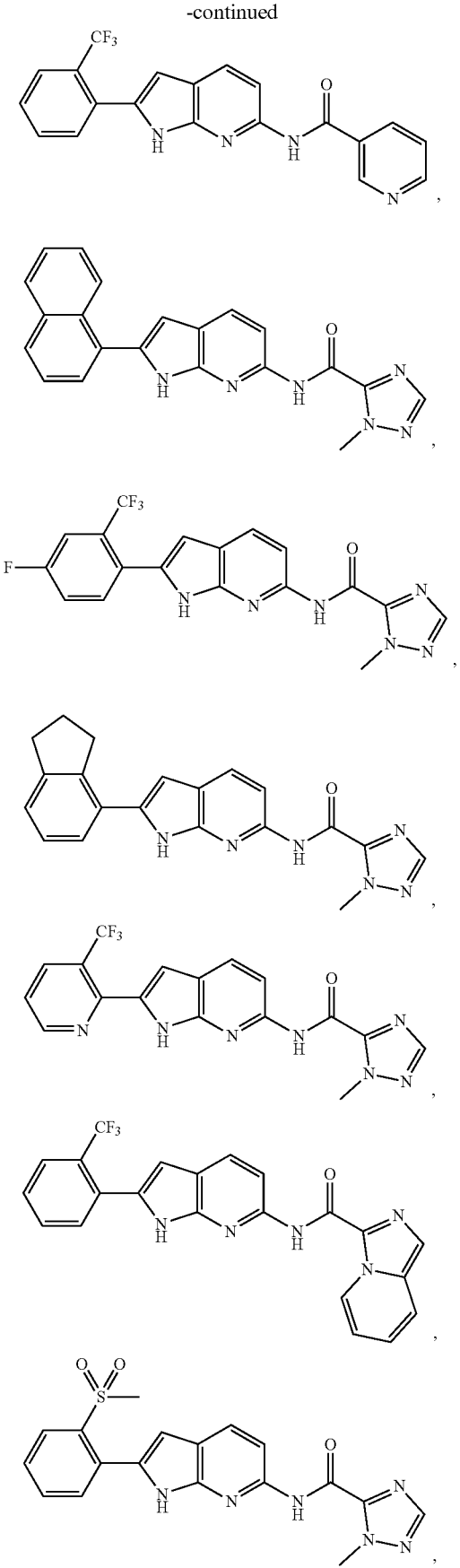

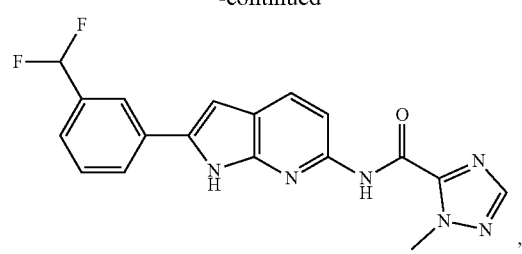
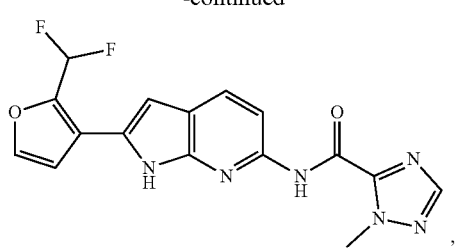
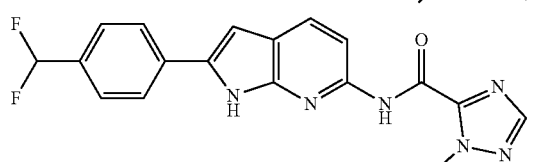
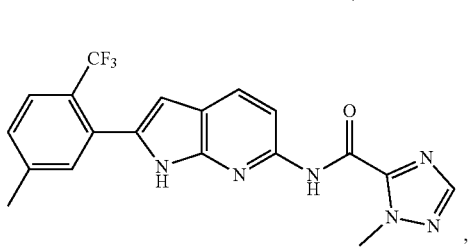
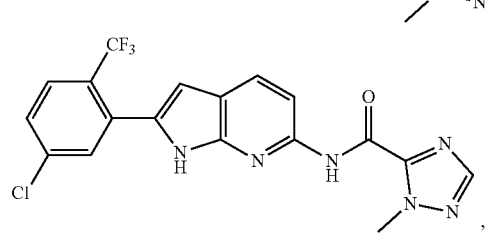
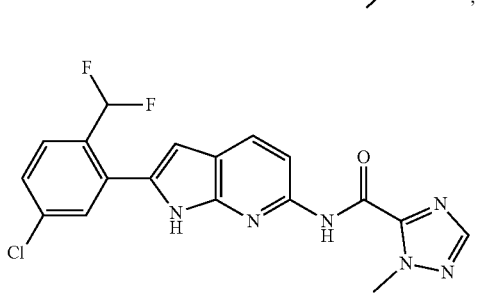
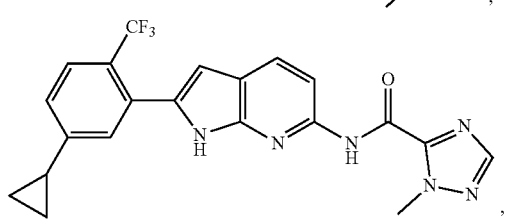
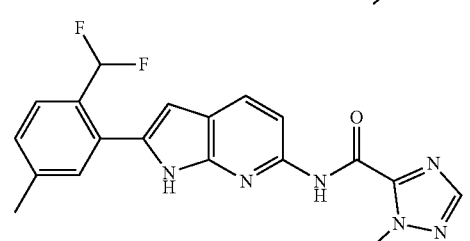
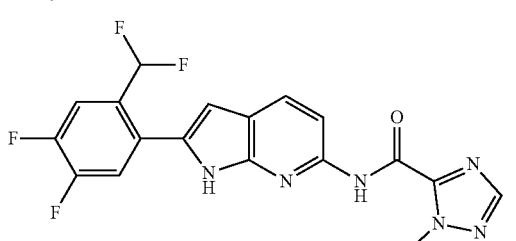
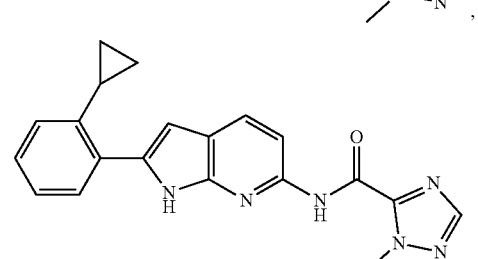
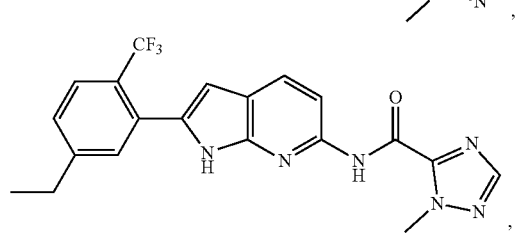
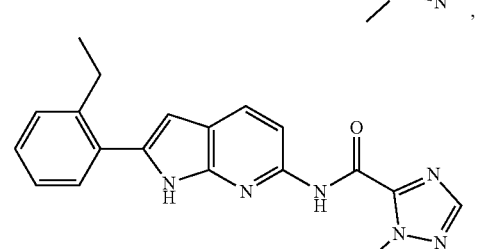
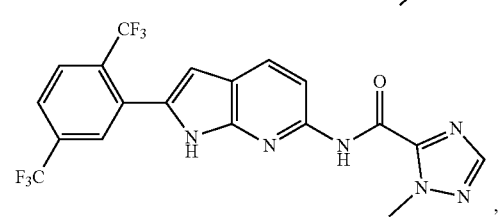
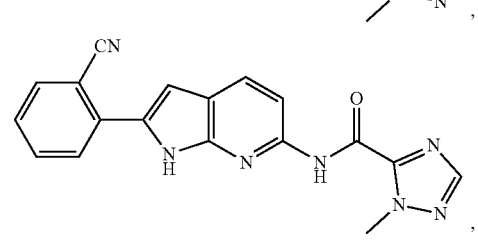
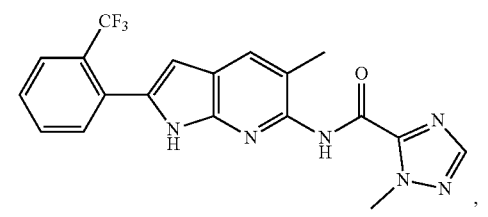

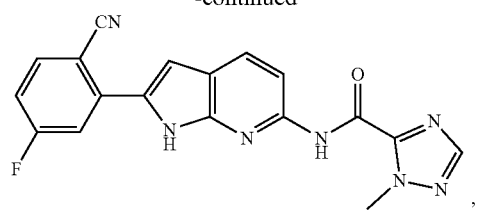
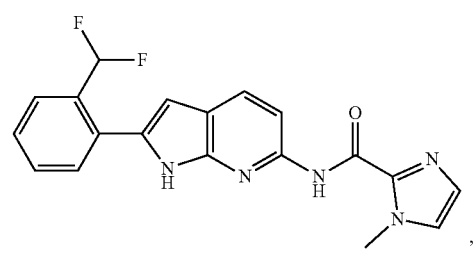
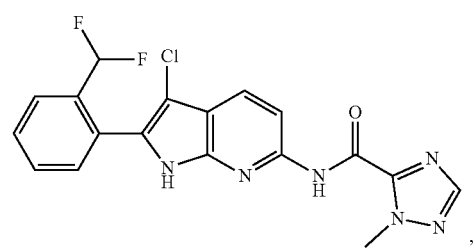
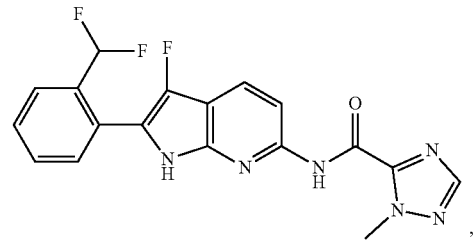
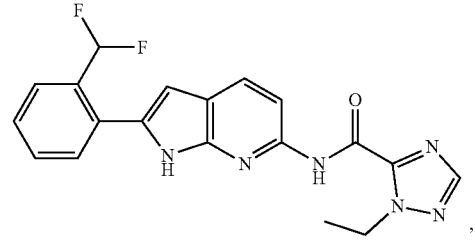
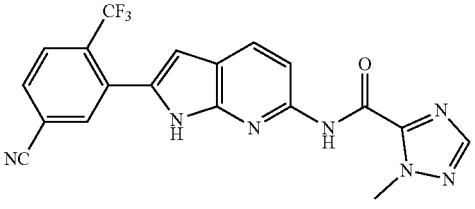
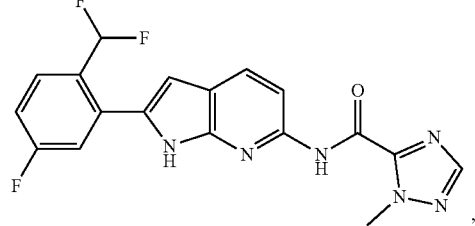
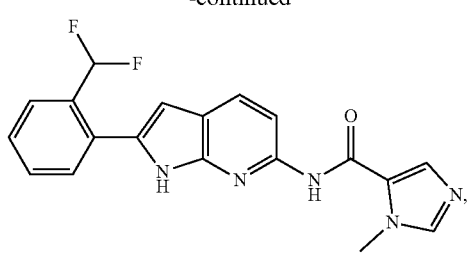
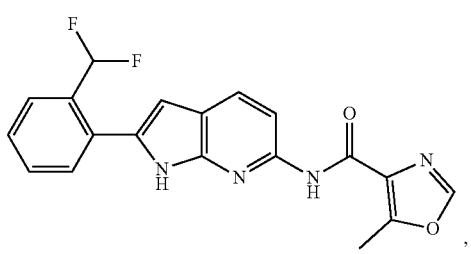
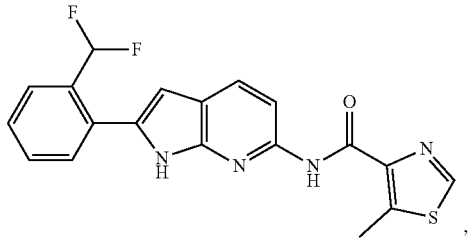
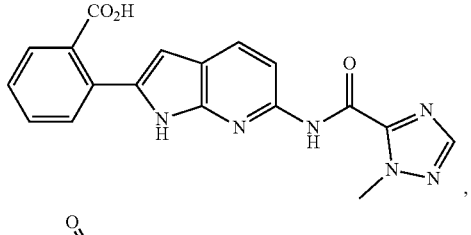
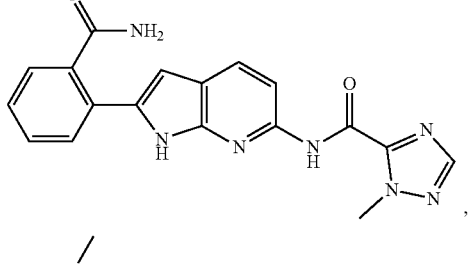
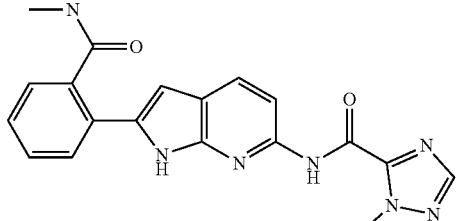
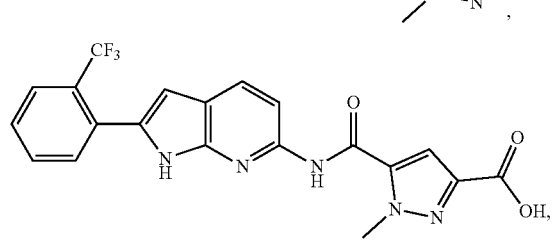

-continued
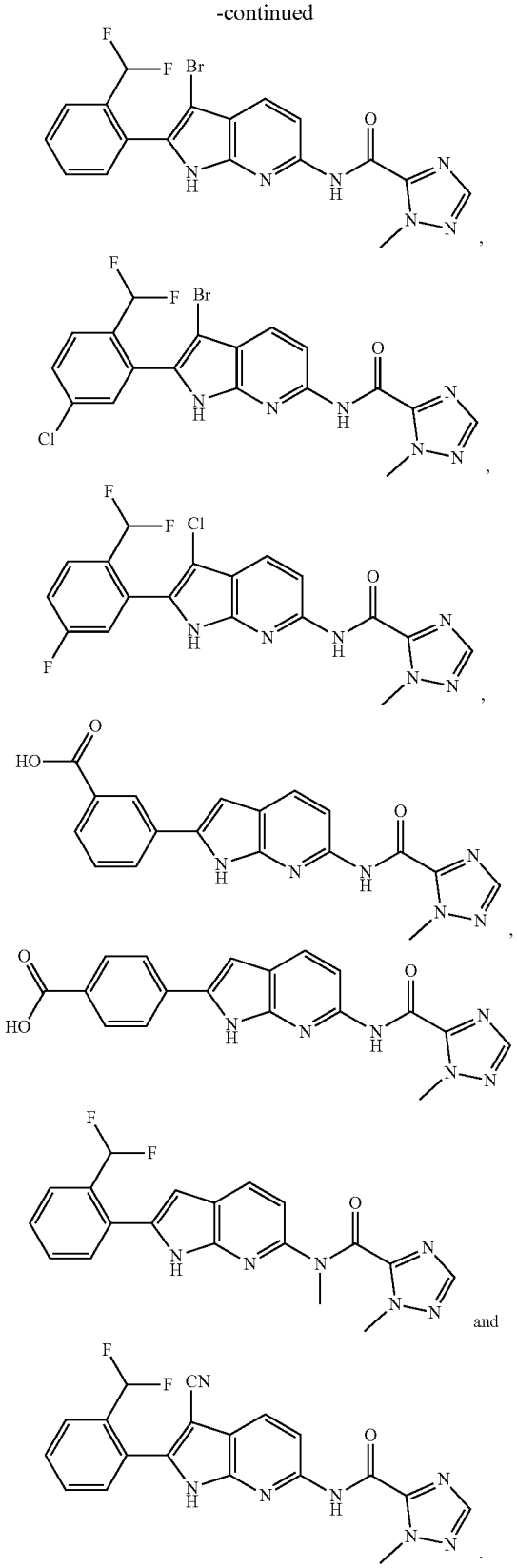
In a further embodiment in combination with any of the above and below embodiments, the compound according to formula (I) is selected from
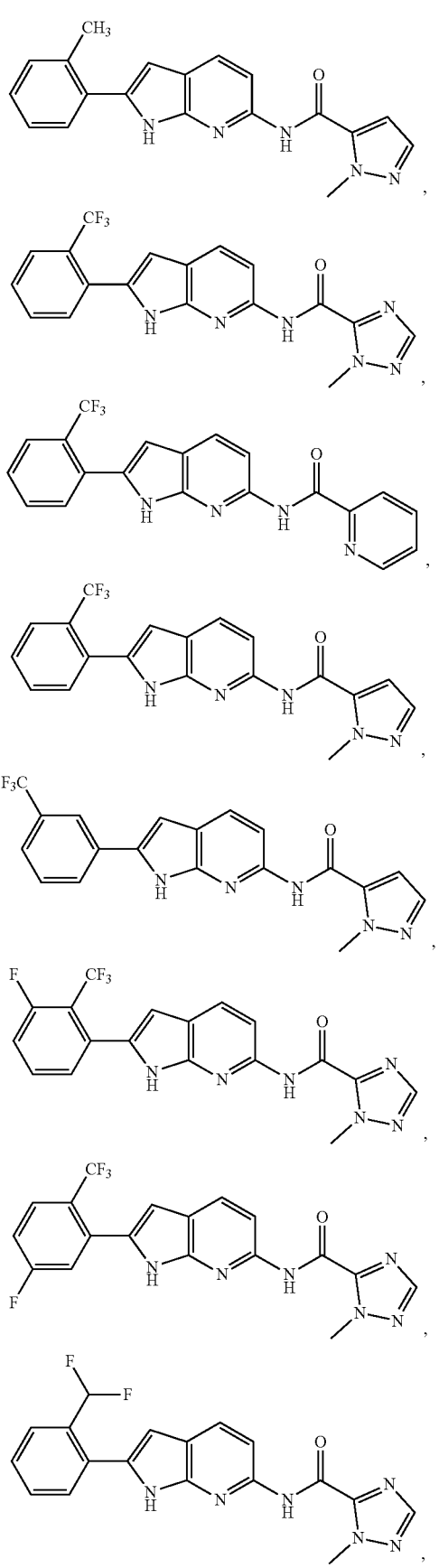

-continued
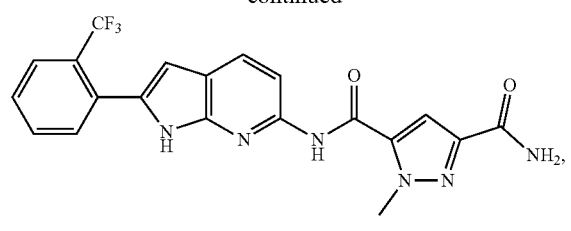
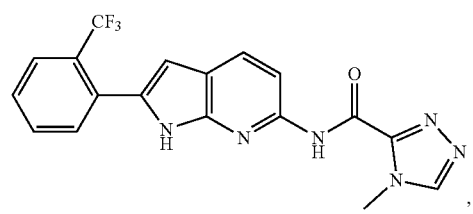
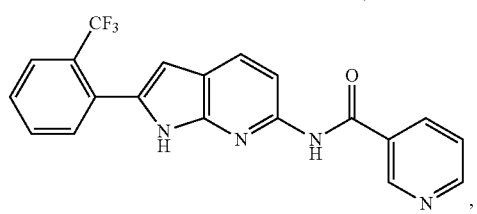
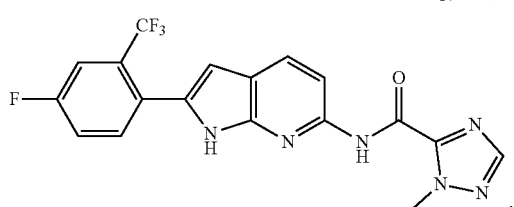
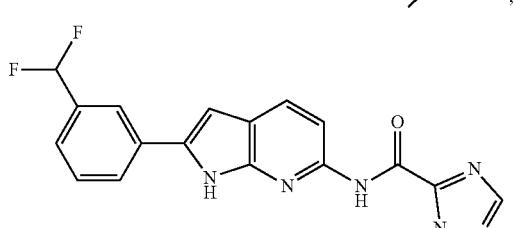
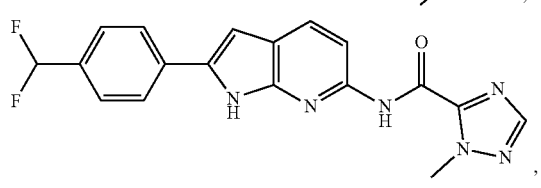
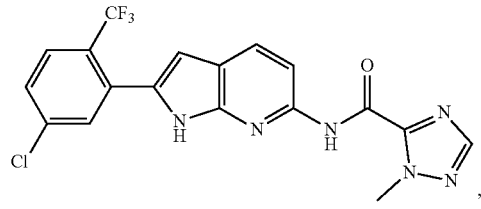
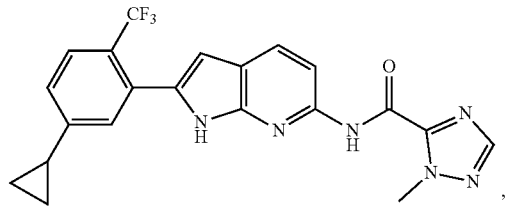
-continued
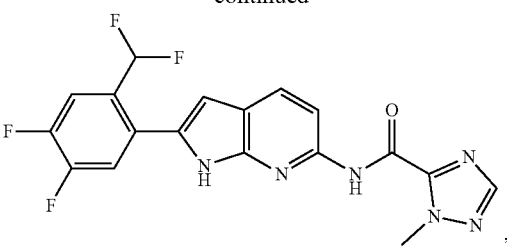
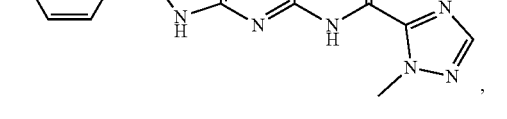
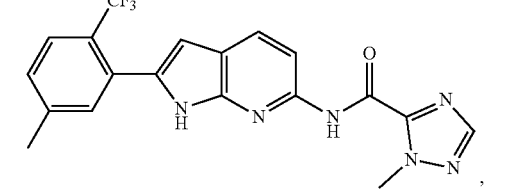
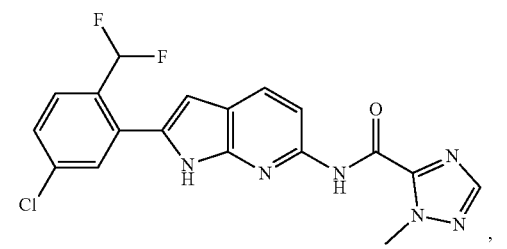
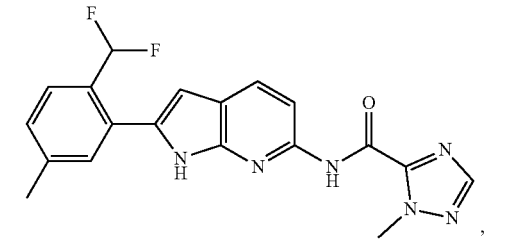

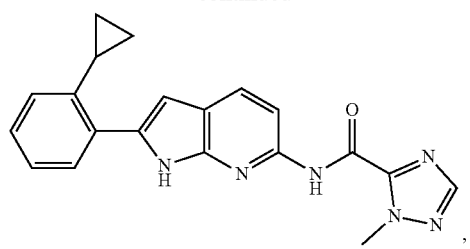
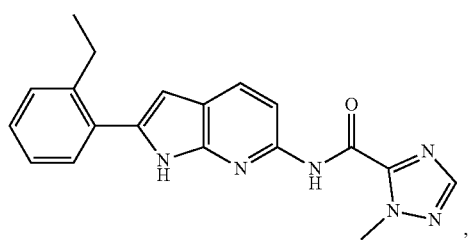
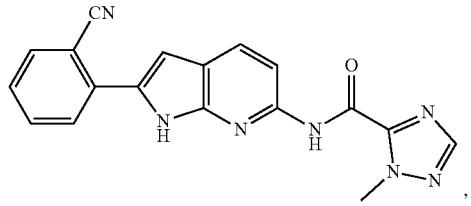
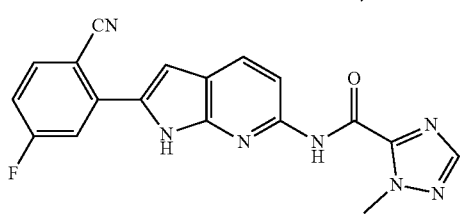
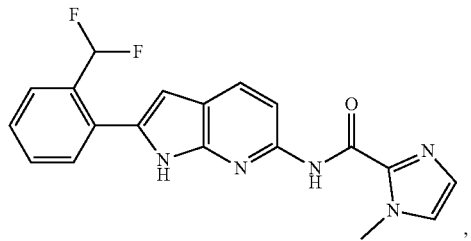
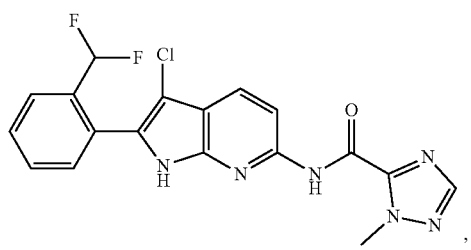
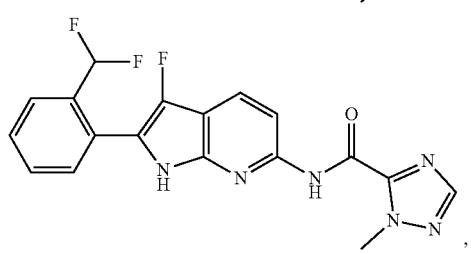
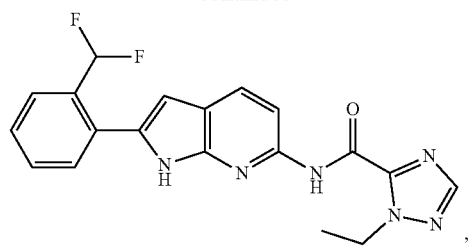
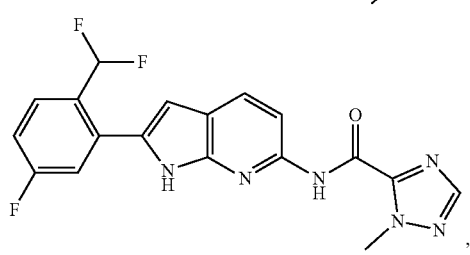
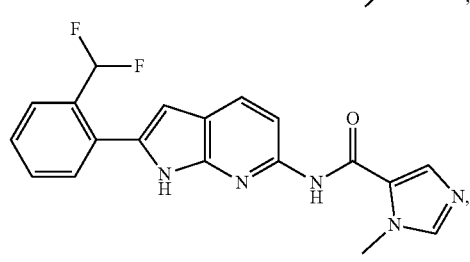
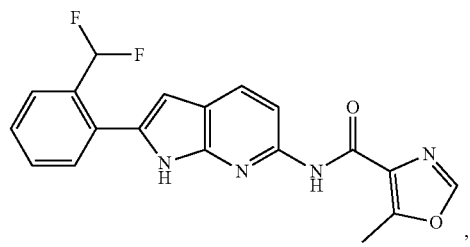
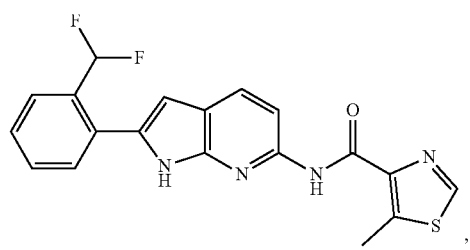
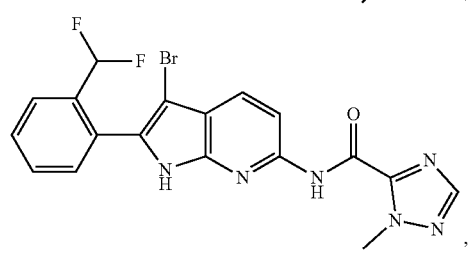

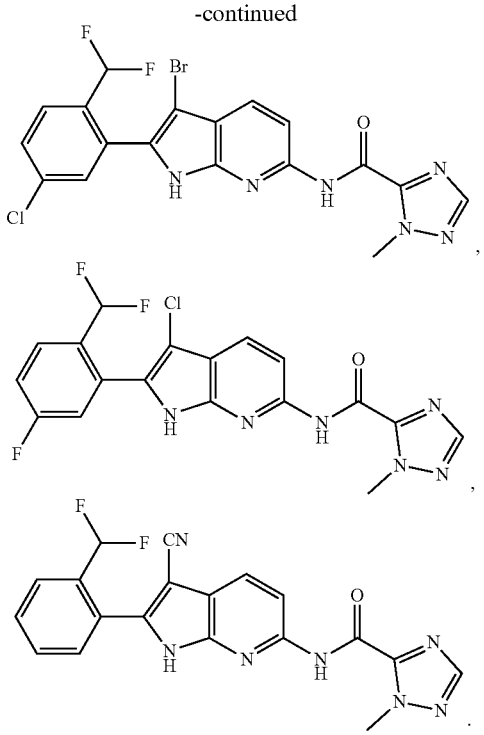

In another embodiment, the present invention is directed to a pharmaceutical composition comprising the compound according to formula (I) and a physiologically acceptable excipient.

In another embodiment, the present invention is directed to the compound according to formula (I) for use as a medicament.

In another embodiment, the present invention is directed to the compound according to formula (I) or a pharmaceutical composition containing same and a physiologically acceptable excipient for use in the prophylaxis and/or treatment of a disease or condition mediated by aryl hydrocarbon receptor (AhR).

In another embodiment in combination with any of the above or below embodiments, the disease or condition mediated by aryl hydrocarbon receptor (AhR) is cancer.

In another embodiment in combination with any of the above or below embodiments, the compound according to formula (I) is administered with one or more therapeutic agents for cancer selected from the group consisting of PD-1 agent, PD-L1 agent, CTLA-4 agent, IDO1 inhibitor, chemotherapeutic agent, anticancer vaccine, and cytokine therapy, or wherein the compound is administered under irradiation therapy.

The compounds of the present invention share a common chemical structure according to formula (I) in claim 1.

In a preferred embodiment in combination with any of the above or below embodiments, the present invention is directed to an enantiomer, diastereomer or pharmaceutically acceptable salt of a compound according to Formula (I).

In a preferred embodiment in combination with any of the above or below embodiments, A in the compound according to Formula (I) is a 6-membered aryl or a 5- to 6-membered monocyclic heteroaryl containing 1 to 4 heteroatoms independently selected from N, O and S, wherein the aryl and heteroaryl are unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a further preferred embodiment in combination with any of the above or below embodiments, A in the compound according to Formula (I) is a 6-membered aryl substituted with 1 or 2 substituents independently selected from OH, CN, halogen, $C_{1-6}$-alkyl, and $C_{3-6}$-cycloalkyl, wherein the alkyl and cycloalkyl may be substituted with 1 to 3 substituents independently selected from halogen and $C_{1-6}$-alkyl.

In an equally preferred embodiment in combination with any of the above or below embodiments, A in the compound according to Formula (I) is 10-membered aryl such as a naphthalene group which is unsubstituted or substituted with 1 to 7 substituents independently selected from the group consisting of halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, NR$^a$C(O)—$C_{1-6}$-alkyl, S(O)$_2$N(R$^a$)$_2$. NR$^a$S(O)$_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo.

In another equally preferred embodiment in combination with any of the above or below embodiments, A in the compound according to Formula (I) is a 6- or 10-membered aryl, more preferable a phenyl group, which is fused with a 5- to 7-membered saturated or partially unsaturated carbocyclic ring or heterocyclic ring containing 1 to 3 heteroatoms independently selected from O, N and S, wherein the carbocyclic or heterocyclic ring is unsubstituted or substituted with 1 to 5 substituents independently selected from the group consisting of halogen, $C_{1-6}$-alkyl and halo-$C_{1-6}$-alkyl.

In a further equally preferred embodiment in combination with any of the above or below embodiments, A in the compound according to Formula (I) is a 5- or 6-membered heteroaryl containing 1 to 3 heteroatoms independently selected form N, O and S, which is fused with a 5- to 7-membered saturated or partially unsaturated carbocyclic ring or heterocyclic ring containing 1 to 3 heteroatoms independently selected from O, N and S, wherein the carbocyclic or heterocyclic ring is unsubstituted or substituted with 1 to 5 substituents independently selected from the group consisting of halogen, $C_{1-6}$-alkyl and halo-$C_{1-6}$-alkyl.

In a preferred embodiment in combination with any of the above or below embodiments, A in the compound according to Formula (I) is a 6-membered aryl or a 5- to 6-membered monocyclic heteroaryl containing 1 to 3 heteroatoms independently selected from N, O and S, wherein the aryl and heteroaryl are unsubstituted or substituted with 1 or 2 substituents independently selected from halogen, $C_{1-6}$-alkyl, and halo-$C_{1-6}$-alkyl.

In a preferred embodiment in combination with any of the above or below embodiments, A in the compound according to Formula (I) is a 6-membered monocyclic heteroaryl containing 1 to 3 nitrogen atoms, which is substituted with 1 or 2 substituents independently selected from OH, CN, halogen, $C_{1-6}$-alkyl, O—$C_{1-6}$-alkyl and $C_{3-6}$-cycloalkyl, wherein the alkyl and cycloalkyl is unsubstituted or substituted with 1 to 3 substituents independently selected from halogen and $C_{1-6}$-alkyl.

In a preferred embodiment in combination with any of the above or below embodiments, A in the compound according to Formula (I) is a 5- to 6-membered monocyclic heteroaryl containing 1 to 4 heteroatoms independently selected from N, O and S, which is substituted with 1 or 2 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, A in the compound according to Formula (I) is

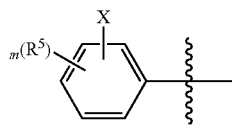

wherein

X is $CH_3$, $CH_2CH_3$, $CHF_2$, $OCF_3$, $OCH_3$ or $CF_3$;

$R^5$ is H, CN or halogen; and m is 0 to 4.

In a preferred embodiment in combination with any of the above or below embodiments, A in the compound according to Formula (I) is

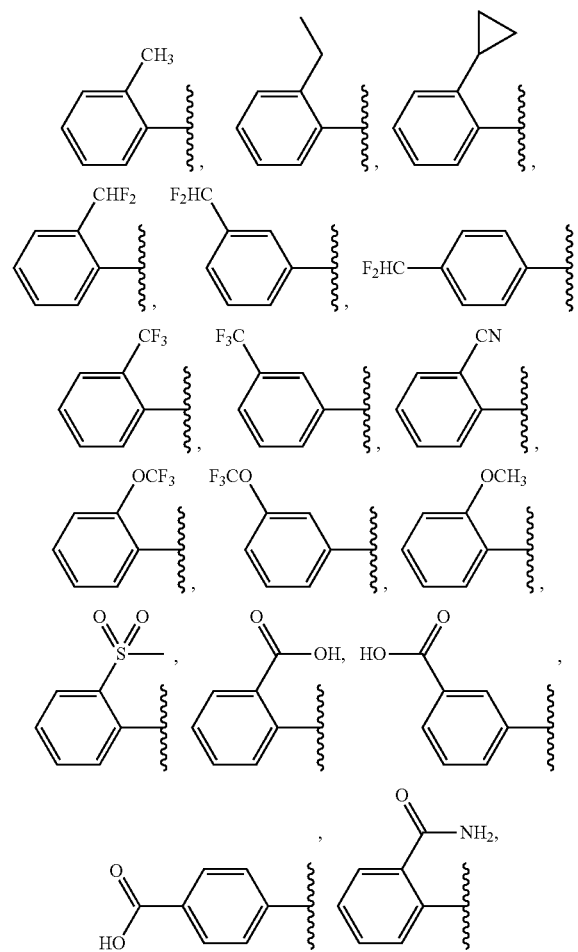

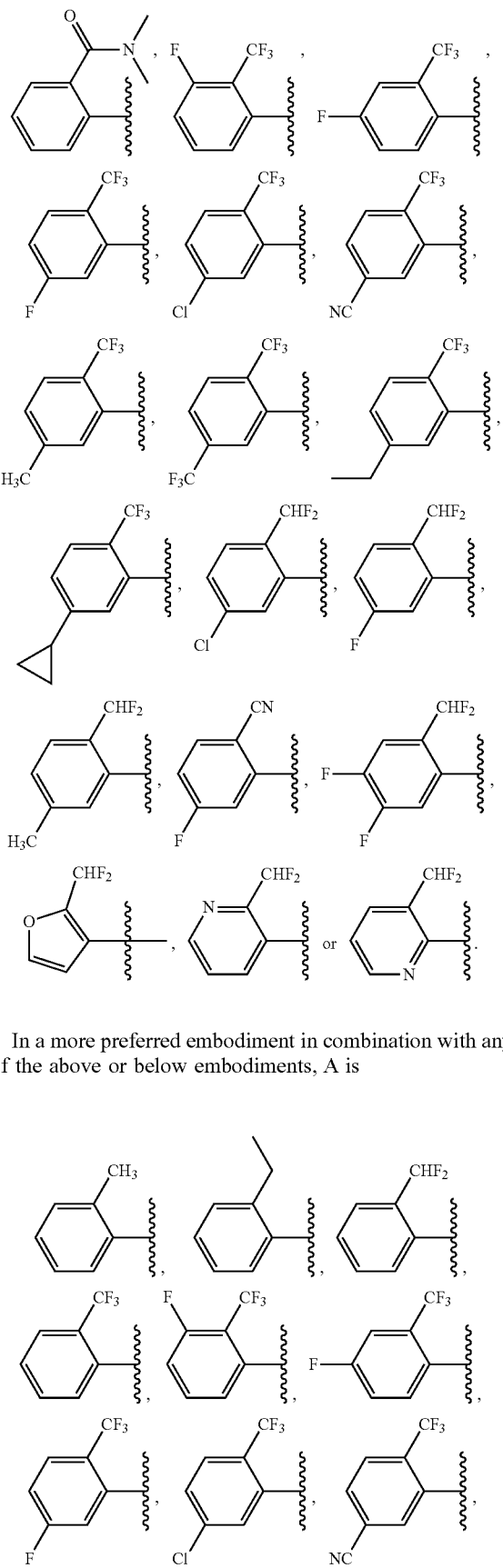

In a more preferred embodiment in combination with any of the above or below embodiments, A is

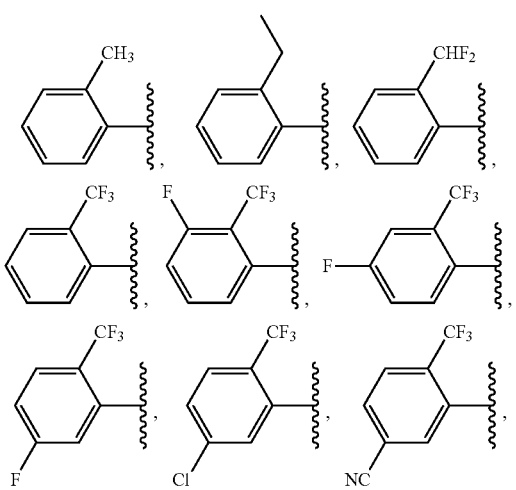

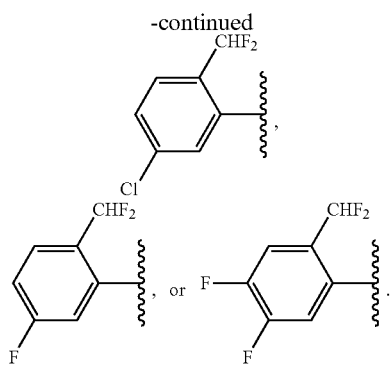

In a preferred embodiment in combination with any of the above or below embodiments, B in the compound according to Formula (I) is a 5- to 10-membered mono- or bicyclic heteroaryl containing 1 to 4 heteroatoms independently selected from N, O and S, which is unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, B in the compound according to Formula (I) is a 5- to 6-membered monocyclic heteroaryl containing 1 to 3 heteroatoms independently selected from N, O and S, which is unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, B in the compound according to Formula (I) is a 5- to 6-membered monocyclic heteroaryl which is unsubstituted or substituted with 1 to 3 substituents independently selected from OH, CN, halogen, $C_{1-6}$-alkyl, and $C_{1-6}$-cycloalkyl, wherein the alkyl and cycloalkyl are unsubstituted or substituted with 1 to 3 substituents independently selected from halogen and $C_{1-6}$-alkyl, wherein the heteroaryl has 1 to 3 heteroatoms independently selected from N, O and S, preferably N and O, and most preferably N.

In a preferred embodiment in combination with any of the above or below embodiments, B in the compound according to Formula (I) is a 5- to 6-membered monocyclic heteroaryl containing 1 to 3 heteroatoms independently selected from N, O and S, which is unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl, wherein the heteroaryl has 1 to 3 N atoms, preferably 2 or 3 N atoms.

In a preferred embodiment in combination with any of the above or below embodiments, B in the compound according to Formula (I) is a 5-membered heteroaryl containing 1 to 3 heteroatoms independently selected from N, O and S, which is unsubstituted or substituted with 1 or 2 substituents independently selected from $C_{1-6}$-alkyl, halo-$C_{1-6}$-alkyl and $C_{3-6}$-cycloalkyl.

In a further preferred embodiment in combination with any of the above or below embodiments, B in the compound according to Formula (I) is

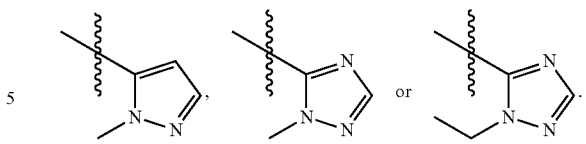

In a preferred embodiment in combination with any of the above or below embodiments, B in the compound according to Formula (I) is 9- or 10-membered bicyclic heteroaryl which is unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl, wherein the heteroaryl has 1 to 3 N atoms, preferably 2 or 3 N atoms.

In a preferred embodiment in combination with any of the above or below embodiments, $R^1$, $R^2$, and $R^3$ in the compound according to Formula (I) are each independently selected from hydrogen, halogen, $C_{1-3}$-alkyl, OH, and CN.

In a preferred embodiment in combination with any of the above or below embodiments, one of $R^1$, $R^2$, and $R^3$ in the compound according to Formula (I) is $C_{1-3}$-alkyl, halogen, or CN, and the other two are hydrogen.

In a preferred embodiment in combination with any of the above or below embodiments, $R^1$, $R^2$, and $R^3$ in the compound according to Formula (I) are hydrogen.

In the context of the present invention "$C_{1-6}$-alkyl" means a saturated alkyl chain having 1 to 6 carbon atoms which may be straight chained or branched. Examples thereof include methyl, ethyl, propyl, isopropyl, n-butyl, isobutyl, tert-butyl, n-pentyl, isopentyl, neopentyl, and hexyl.

The term "O—$C_{1-6}$-alkyl" means that the alkyl chain is connected via an oxygen atom with the remainder of the molecule.

The term "halo-$C_{1-10}$-alkyl" means that one or more hydrogen atoms in the alkyl chain are replaced by a halogen. A preferred example thereof is $CF_3$.

A $C_{3-6}$-cycloalkyl group means a saturated or partially unsaturated mono- or bicyclic ring system comprising 3 to 6 carbon atoms. Examples include cyclopropyl, cyclobutyl, cyclopentyl, and cyclohexyl.

A 5-10-membered mono- or bicyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl, pyrazolo[1,5-a]pyrimidinyl and dibenzo[b,d]furanyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

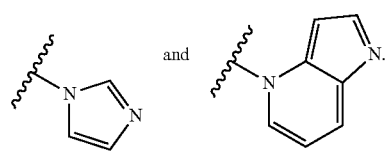 [SMILES: *n1ccnc1 ; *n1cccc2nccc1-2]

Moreover, where not explicitly defined, heteroaryl contains 1 to 4 heteroatoms independently selected from the group consisting of N, O and S.

A 6-10-membered mono- or bicyclic aromatic ring system (within the application also referred to as aryl) means an aromatic carbon cycle such as phenyl or naphthyl.

The term "halogen" comprises the specific halogen atoms fluorine, bromine, chlorine and iodine.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, fluorine and chlorine, such as, but not limited to $^2$H (deuterium, D), $^3$H (tritium), $^{11}$C, $^{13}$C, $^{14}$C, $^{15}$N, $^{18}$F, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds of Formula (I) in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g. a human. See, for example, Foster in Trends Pharmacol. Sci. 1984:5; 524. Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds, wherein the carboxylate in a compound of the present invention is, for example, converted into an alkyl-, aryl-, choline-, amino, acyloxymethylester, linolenoylester.

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials. Another way to obtain pure enantiomers from racemic mixtures would use enantioselective crystallization with chiral counterions.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatine; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring such as cherry or orange flavour.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous, intramuscular and subcutaneous), ocular (ophthalmic), pulmonary (nasal or buccal inhalation), nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing AhR-mediated conditions for which compounds of Formula (I) are indicated, generally satisfactory results are obtained when the compounds are administered at a daily dosage of from about 0.1 mg to about 100 mg per kilogram of mammal body weight, preferably given as a single daily dose or in divided doses two to six times a day, or in sustained release form. For most large mammals, the total daily dosage is from about 1 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Abbreviations

Herein and throughout the application, the following abbreviations may be used.
Ac acetyl
Boc tert-butyloxycarbonyl
br broad
CDI 1,1'-carbonyldiimidazole
d doublet
DAST (diethylamino)sulfur trifluoride
dba dibenzylideneacetone
DBU 1,8-diazabicyclo[5.4.0]undec-7-ene
DCM dichloromethane
DIBAL-H diisobutylaluminum hydride
DIPEA N,N-diisopropylethylamine
DMAP 4-(dimethylamino)pyridine
DMF N,N-dimethylformamide
DMSO dimethyl sulfoxide
dppf 1,1'-bis(diphenylphosphanyl) ferrocene
EDC 1-ethyl-3-(3-dimethylaminopropyl)carbodiimide
Et ethyl
Et$_2$O diethyl ether
EtOAc ethyl acetate
HATU O-(7-azabenzotriazol-1-yl)-N,N,N',N'-tetramethyluronium hexafluorophosphate
HPLC high performance liquid chromatography
m multiplet
MCPBA 3-chloroperoxybenzoic acid
Me methyl
Ms methanesulfonyl
NBS N-bromosuccinimide
NCS N-chlorosuccinimide
NIS N-iodosuccinimide
PE petroleum ether
rt room temperature
s singlet
SEM 2-(trimethylsilyl)ethoxymethyl
t triplet
TFA trifluoroacetic acid
TEA triethylamine
THF tetrahydrofurane
tBuXPhos 2-di-tert-butylphosphino-2',4',6'-triisopropylbiphenyl

GENERAL SCHEMES

The compounds of the present invention can be prepared by a combination of methods known in the art including the procedures described in scheme 1 below. The following reaction schemes are only meant to represent examples of the invention and are in no way meant to be a limit of the invention.

Scheme 1 describes one route of preparation for the compounds of the present invention. A substituted or unsubstituted 6-chloro-3-iodopyridin-2-amine A-1 is converted to the corresponding bis methylsulfonamide A-2 with sulfonylchloride in the presence of triethylamine. Treatment of A-2 with NaOH affords the corresponding mono methylsulfonamide A-3 which is converted to azaindole A-4 via Pd/Cu(I) catalysed coupling/cyclisation reaction with an appropriately substituted alkyne. Boc-protection to intermediate A-5 followed by Buchwald amidation affords the corresponding amide A-6. Intermediate A-6 is converted to compounds of structure A-7 by deprotection with for example TFA.

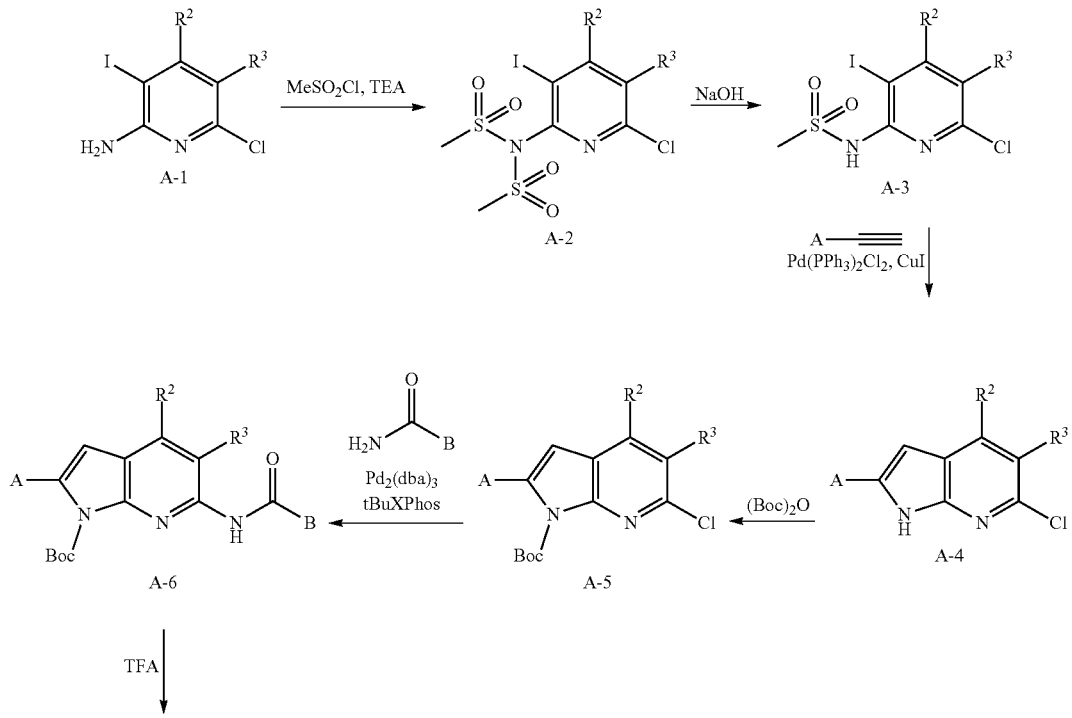

Scheme 1

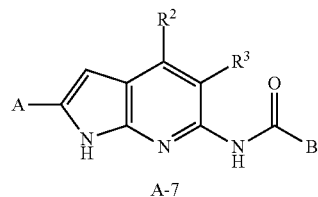

A-7

Scheme 2 describes an alternative route of preparation for the compounds of the present invention. A substituted or unsubstituted 6-chloro-1H-pyrrolo[2,3-b]pyridine B-1 is converted to the corresponding 2-(trimethylsilyl)ethoxymethyl protected intermediate B-2 through treatment with NaH and ((chloromethoxy) methyl)trimethylsilane. Intermediate B-2 can be iodinated by treatment with n-BuLi at −78° C. followed by addition of iodine to give iodide B-3. Suzuki coupling of B-3 with a boronic acid or ester affords intermediates of structure B-4. Buchwald amidation with an amide gives intermediates of structure B-5 which can be deprotected with e.g. BF$_3$.Et$_2$O to afford compounds of structure B-6. Additionally compounds of structure B-6 can be converted into compounds of structure B-8 in a sequence of amide hydrolysis with NaOH followed by amide coupling with a carboxylic acid.

Intermediate 1:
1-Ethynyl-3-fluoro-2-(trifluoromethyl)benzene (Int 1)

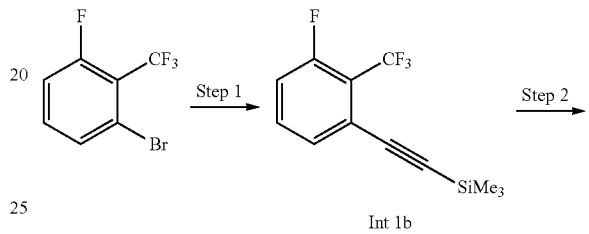

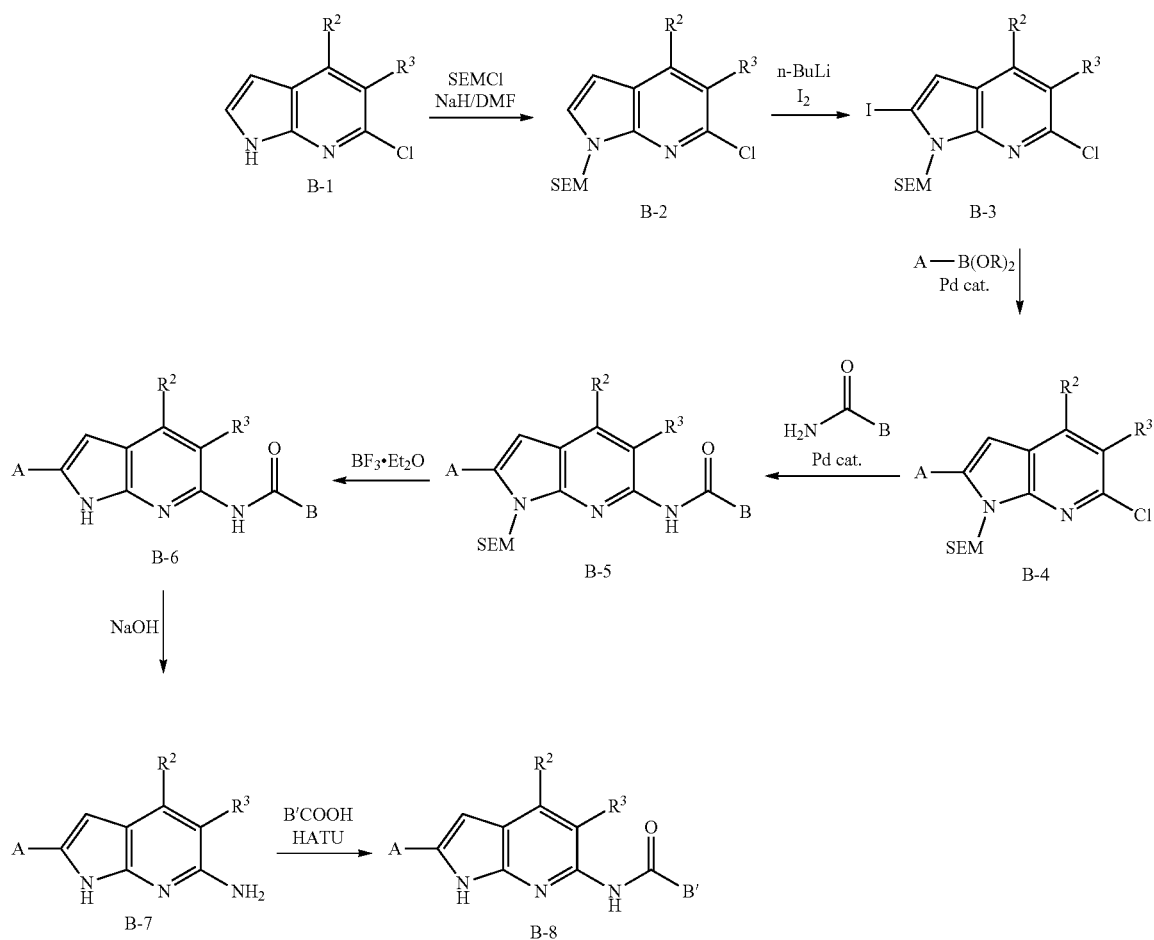

Scheme 2

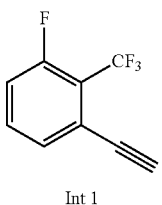

Int 1

Step 1: ((3-Fluoro-2-(trifluoromethyl)phenyl)ethynyl)trimethylsilane (Int 1b)

A mixture of Pd(PPh$_3$)$_4$ (95 mg, 0.083 mmol), CuI (32 mg, 0.165 mmol), 1-bromo-3-fluoro-2-(trifluoromethyl) benzene (Int 1a) (1.00 g, 4.13 mmol) and ethynyl-trimethylsilane (1.42 g, 14.5 mmol) in TEA (10 mL) was stirred under N$_2$ at 70° C. overnight. The mixture was concentrated to dryness, EtOAc (20 mL) was added and the mixture was filtered through Celite®. The filtrate was concentrated to dryness and the residue was purified by column chromatography (hexane) to give the title compound as a yellow oil.

Step 2: 1-Ethynyl-3-fluoro-2-(trifluoromethyl)benzene (Int 1)

To a mixture of ((3-fluoro-2-(trifluoromethyl)phenyl) ethynyl)trimethylsilane (Int 1b) (0.881 g, 3.39 mmol) in THF (15 mL) was added TBAF (5 mL, 1N in THF) and the mixture was stirred at rt overnight. Water was added and the mixture was extracted with EtOAc (3×30 mL). The combined organic layers were dried over anhydrous MgSO$_4$, filtered and concentrated to dryness. The residue was purified by column chromatography (gradient 5-100% EtOAc in PE) to give the title compound as a yellow oil.

Intermediate 1/1: 3-Ethynyl-2-(trifluoromethyl)pyridine (Int 1/1)

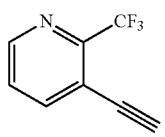

The title compound was prepared similar as described for Intermediate 1 using in Step 1 3-bromo-2-(trifluoromethyl) pyridine in place of 1-bromo-3-fluoro-2-(trifluoromethyl) benzene.

Intermediate 1/2: 1-Ethynyl-2-(trifluoromethoxy)benzene (Int 1/2)

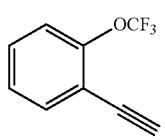

The title compound was prepared similar as described for Intermediate 1 using in Step 1 1-bromo-2-(trifluoromethoxy)benzene in place of 1-bromo-3-fluoro-2-(trifluoromethyl) benzene.

Intermediate 1/3: 1-Ethynyl-3-(trifluoromethoxy)benzene (Int 1/3)

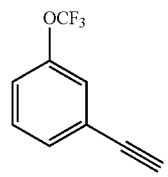

The title compound was prepared similar as described for Intermediate 1 using in Step 1 1-bromo-3-(trifluoromethoxy)benzene in place of 1-bromo-3-fluoro-2-(trifluoromethyl) benzene.

Intermediate 1/4: 2-Ethynyl-4-fluoro-1-(trifluoromethyl)benzene (Int 1/4)

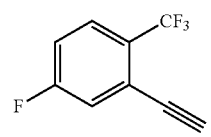

The title compound was prepared similar as described for Intermediate 1 using in Step 1 2-bromo-4-fluoro-1-(trifluoromethyl)benzene in place of 1-bromo-3-fluoro-2-(trifluoromethyl)benzene.

Intermediate 1/5: 1-Ethynylnaphthalene (Int 1/5)

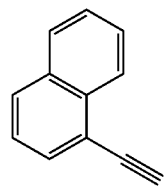

The title compound was prepared similar as described for Intermediate 1 using in Step 1 1-iodonaphthalene in place of 1-bromo-3-fluoro-2-(trifluoromethyl)benzene.

Intermediate 1/6: 1-Ethynyl-4-fluoro-2-(trifluoromethyl)benzene (Int 1/6)

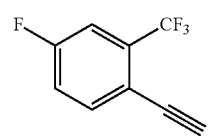

The title compound was prepared similar as described for Intermediate 1 using in Step 1 1-bromo-4-fluoro-2-(trifluoromethyl)benzene in place of 1-bromo-3-fluoro-2-(trifluoromethyl)benzene.

Intermediate 1/7:
1-(Difluoromethyl)-2-ethynylbenzene (Int 1/7)

The title compound was prepared similar as described for Intermediate 1 using in Step 1 1-bromo-2-(difluoromethyl)benzene in place of 1-bromo-3-fluoro-2-(trifluoromethyl)benzene.

Intermediate 1/8: 4-Ethynyl-2,3-dihydro-1H-indene (Int 1/8)

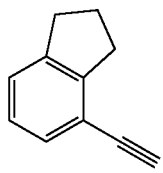

The title compound was prepared similar as described for Intermediate 1 using in Step 1 4-bromo-2,3-dihydro-1H-indene in place of 1-bromo-3-fluoro-2-(trifluoromethyl)benzene.

Intermediate 1/9:
2-Ethynyl-3-(trifluoromethyl)pyridine (Int 1/9)

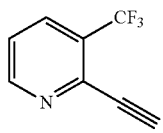

The title compound was prepared similar as described for Intermediate 1 using in Step 1 2-bromo-3-(trifluoromethyl)pyridine in place of 1-bromo-3-fluoro-2-(trifluoromethyl)benzene.

Intermediate 1/10:
1-Ethynyl-2-(methylsulfonyl)benzene (Int 1/10)

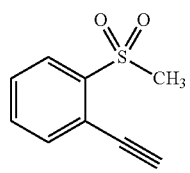

The title compound was prepared similar as described for Intermediate 1 using in Step 1 1-bromo-2-(methylsulfonyl)benzene in place of 1-bromo-3-fluoro-2-(trifluoromethyl)benzene.

Intermediate 1/11: Methyl 2-ethynylbenzoate (Int 1/11)

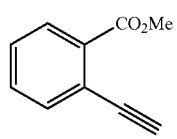

The title compound was prepared similar as described for Intermediate 1 using in Step 1 methyl 2-bromobenzoate in place of 1-bromo-3-fluoro-2-(trifluoromethyl)benzene.

Intermediate 1/12:
1-(Difluoromethyl)-3-ethynylbenzene (Int 1/12)

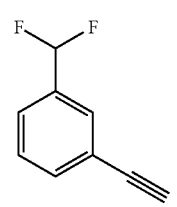

The title compound was prepared similar as described for Intermediate 1 using in Step 1 1-bromo-3-(difluoromethyl)benzene in place of 1-bromo-3-fluoro-2-(trifluoromethyl)benzene.

Intermediate 1/13:
1-(Difluoromethyl)-4-ethynylbenzene (Int 1/13)

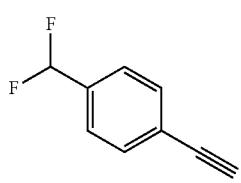

The title compound was prepared similar as described for Intermediate 1 using in Step 1 1-bromo-4-(difluoromethyl)benzene in place of 1-bromo-3-fluoro-2-(trifluoromethyl)benzene.

Intermediate 1/14:
4-Chloro-2-ethynyl-1-(trifluoromethyl)benzene (Int 1/14)

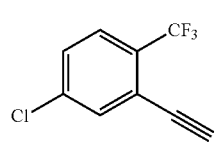

The title compound was prepared similar as described for Intermediate 1 using in Step 1 2-bromo-4-chloro-1-(trifluoromethyl)benzene in place of 1-bromo-3-fluoro-2-(trifluoromethyl)benzene.

Intermediate 1/15:
2-Ethynyl-1,4-bis(trifluoromethyl)benzene (Int 1/15)

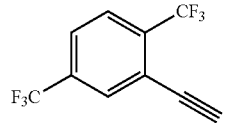

The title compound was prepared similar as described for Intermediate 1 using in Step 1 2-iodo-1,4-bis(trifluoromethyl)benzene in place of 1-bromo-3-fluoro-2-(trifluoromethyl) benzene.

Intermediate 1/16: 3-Ethynylfuran-2-carbaldehyde (Int 1/16)

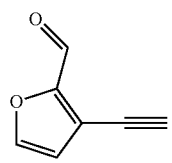

The title compound was prepared similar as described for Intermediate 1 using in Step 1 3-bromofuran-2-carbaldehyde in place of 1-bromo-3-fluoro-2-(trifluoromethyl) benzene.

Intermediate 1/17:
2-Ethynyl-4-methyl-1-(trifluoromethyl)benzene (Int 1/17)

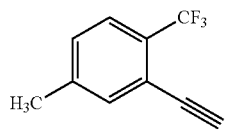

The title compound was prepared similar as described for Intermediate 1 using in Step 1 2-bromo-4-methyl-1-(trifluoromethyl)benzene in place of 1-bromo-3-fluoro-2-(trifluoromethyl)benzene.

Intermediate 1/18:
4-Chloro-1-(difluoromethyl)-2-ethynylbenzene (Int 1/18)

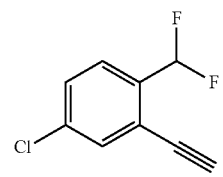

The title compound was prepared similar as described for Intermediate 1 using in Step 1 2-bromo-4-chloro-1-(difluoromethyl)benzene in place of 1-bromo-3-fluoro-2-(trifluoromethyl)benzene.

Intermediate 1/19:
1-(Difluoromethyl)-2-ethynyl-4-methylbenzene (Int 1/19)

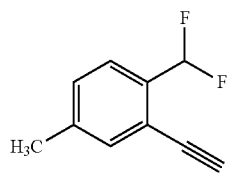

The title compound was prepared similar as described for Intermediate 1 using in Step 1 2-bromo-1-(difluoromethyl)-4-methylbenzene in place of 1-bromo-3-fluoro-2-(trifluoromethyl)benzene.

Intermediate 2: tert-Butyl 6-chloro-2-(o-tolyl)-1H-pyrrolo[2,3-b]pyridine-1-carboxylate (Int 2)

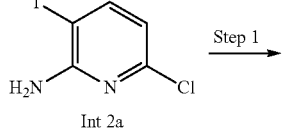

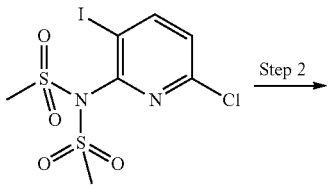

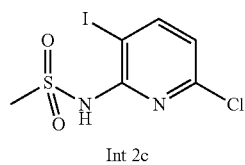

Step 1: N-(6-Chloro-3-iodopyridin-2-yl)-N-(methylsulfonyl)methanesulfonamide (Int 2b)

Methanesulfonyl chloride (5.5 mL, 70.9 mmol) was added dropwise to a solution of 6-chloro-3-iodopyridin-2-amine (Int 2a) (5.0 g, 19.7 mmol) in pyridine (50 mL) at 0°

C. The mixture was allowed to warm to rt and stirred overnight. The mixture was concentrated to dryness and the residue was purified by column chromatography (gradient 5%-100% EtOAc in DCM) to give the title compound as a yellow solid.

Step 2: N-(6-Chloro-3-iodopyridin-2-yl)methanesulfonamide (Int 2c)

N-(6-Chloro-3-iodopyridin-2-yl)-N-(methylsulfonyl)methanesulfonamide (Int 2b) (5.3 g, 12.9 mmol) was dissolved in a mixture of aqueous NaOH (10 w/w %, 32.5 mL) and tetrahydrofuran (32.5 mL). The mixture was stirred at rt for 16 h. The mixture was concentrated, water was added and the pH was adjusted to pH 4 using aqueous citric acid. The precipitated solid was filtered and the residue was purified by column chromatography (gradient 5-100% EtOAc in DCM) to give the title compound as a yellow solid.

Step 3: 6-Chloro-2-(o-tolyl)-1H-pyrrolo[2,3-b]pyridine (Int 2d)

A mixture of N-(6-chloro-3-iodopyridin-2-yl)methanesulfonamide (Int 2c) (2.33 g, 7.02 mmol), 1-ethynyl-2-methylbenzene (1.22 g, 10.5 mmol), bis(triphenylphosphine) palladium(II) dichloride (246 mg, 0.35 mmol), copper(I) iodide (39 mg, 0.35 mmol) and triethylamine (3.19 g, 31.6 mmol) in DMF (25 mL) was stirred under nitrogen at 100° C. for 2 h. DBU (2.5 mL) was added and the mixture was stirred at 100° C. overnight. The mixture was cooled to rt, diluted with aqueous NH₄Cl solution and extracted with EtOAc. The combined organic layers were dried over anhydrous MgSO₄ and concentrated to dryness. The residue was purified by column chromatography (gradient 5-10% EtOAc in PE) to give the title compound as a yellow solid.

Step 4: tert-Butyl 6-chloro-2-(o-tolyl)-1H-pyrrolo[2,3-b]pyridine-1-carboxylate (Int 2)

To a mixture of 6-chloro-2-(o-tolyl)-1H-pyrrolo[2,3-b]pyridine (Int 2d) (651 mg, 2.69 mmol) in DCM (10 mL) was added di-tert-butyl dicarbonate (645 mg, 2.96 mmol) dissolved in DCM (10 mL), followed by DMAP (33 mg, 0.27 mmol). The mixture was stirred at rt for 2 h. The mixture was absorbed onto silica and purified by column chromatography (DCM/EtOAc 9:1) to give the title compound as a yellow solid.

Intermediate 2/1: tert-Butyl 6-chloro-2-(2-(trifluoromethyl)phenyl)-1H-pyrrolo[2,3-b]pyridine-1-carboxylate (Int 2/1)

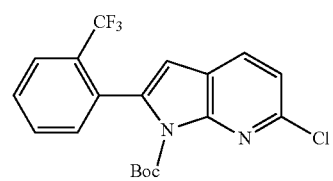 [SMILES: CC(C)(C)OC(=O)n1c(-c2ccccc2C(F)(F)F)cc2ccc(Cl)nc21]

The title compound was prepared similar as described for Intermediate 2 using in step 3 1-ethynyl-2-(trifluoromethyl)benzene in place of 1-ethynyl-2-methylbenzene.

Intermediate 2/2: tert-Butyl 6-chloro-2-(3-(trifluoromethyl)phenyl)-1H-pyrrolo[2,3-b]pyridine-1-carboxylate (Int 2/2)

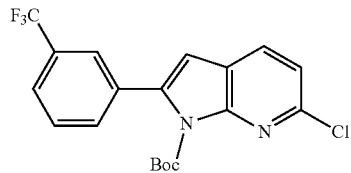 [SMILES: CC(C)(C)OC(=O)n1c(-c2cccc(C(F)(F)F)c2)cc2ccc(Cl)nc21]

The title compound was prepared similar as described for Intermediate 2 using in step 3 1-ethynyl-3-(trifluoromethyl)benzene in place of 1-ethynyl-2-methylbenzene.

Intermediate 2/3: tert-Butyl 6-chloro-2-(2-(trifluoromethyl)pyridin-3-yl)-1H-pyrrolo[2,3-b]pyridine-1-carboxylate (Int 2/3)

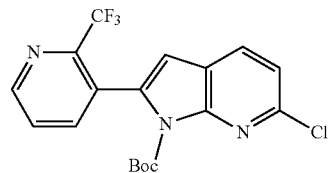 [SMILES: CC(C)(C)OC(=O)n1c(-c2cccnc2C(F)(F)F)cc2ccc(Cl)nc21]

The title compound was prepared similar as described for Intermediate 2 using in step 3 3-ethynyl-2-(trifluoromethyl)pyridine (Int 1/1) in place of 1-ethynyl-2-methylbenzene.

Intermediate 2/4: tert-Butyl 6-chloro-2-(2-(trifluoromethoxy)phenyl)-1H-pyrrolo[2,3-b]pyridine-1-carboxylate (Int 2/4)

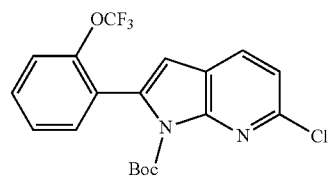 [SMILES: CC(C)(C)OC(=O)n1c(-c2ccccc2OC(F)(F)F)cc2ccc(Cl)nc21]

The title compound was prepared similar as described for Intermediate 2 using in step 3 1-ethynyl-2-(trifluoromethoxy)benzene (Int 1/2) in place of 1-ethynyl-2-methylbenzene.

Intermediate 2/5: tert-Butyl 6-chloro-2-(3-(trifluoromethoxy)phenyl)-1H-pyrrolo[2,3-b]pyridine-1-carboxylate (Int 2/5)

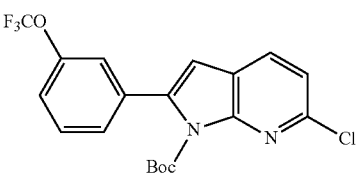 [SMILES: CC(C)(C)OC(=O)n1c(-c2cccc(OC(F)(F)F)c2)cc2ccc(Cl)nc21]

The title compound was prepared similar as described for Intermediate 2 using in step 3 1-ethynyl-3-(trifluoromethoxy)benzene (Int 1/3) in place of 1-ethynyl-2-methylbenzene.

Intermediate 2/6: tert-Butyl 6-chloro-2-(3-fluoro-2-(trifluoromethyl)phenyl)-1H-pyrrolo[2,3-b]pyridine-1-carboxylate (Int 2/6)

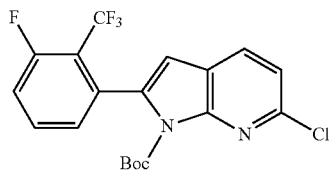 [SMILES: CC(C)(C)OC(=O)n1c(-c2cccc(F)c2C(F)(F)F)cc2ccc(Cl)nc21]

The title compound was prepared similar as described for Intermediate 2 using in step 3 1-ethynyl-3-fluoro-2-(trifluoromethyl)benzene (Int 1) in place of 1-ethynyl-2-methylbenzene.

Intermediate 2/7: tert-Butyl 6-chloro-2-(5-fluoro-2-(trifluoromethyl)phenyl)-1H-pyrrolo[2,3-b]pyridine-1-carboxylate (Int 2/7)

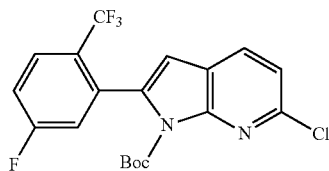 [SMILES: CC(C)(C)OC(=O)n1c(-c2cc(F)ccc2C(F)(F)F)cc2ccc(Cl)nc21]

The title compound was prepared similar as described for Intermediate 2 using in step 3 2-ethynyl-4-fluoro-1-(trifluoromethyl)benzene (Int 1/4) in place of 1-ethynyl-2-methylbenzene.

Intermediate 2/8: tert-Butyl 6-chloro-2-(naphthalen-1-yl)-1H-pyrrolo[2,3-b]pyridine-1-carboxylate (Int 2/8)

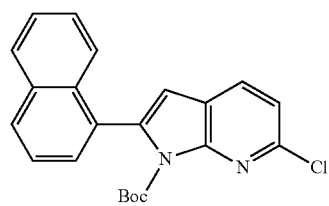 [SMILES: CC(C)(C)OC(=O)n1c(-c2cccc3ccccc23)cc2ccc(Cl)nc21]

The title compound was prepared similar as described for Intermediate 2 using in step 3 1-ethynylnaphthalene (Int 1/5) in place of 1-ethynyl-2-methylbenzene.

Intermediate 2/9: tert-Butyl 6-chloro-2-(4-fluoro-2-(trifluoromethyl)phenyl)-1H-pyrrolo[2,3-b]pyridine-1-carboxylate (Int 2/9)

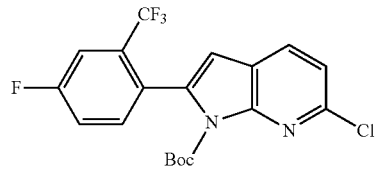 [SMILES: CC(C)(C)OC(=O)n1c(-c2ccc(F)cc2C(F)(F)F)cc2ccc(Cl)nc21]

The title compound was prepared similar as described for Intermediate 2 using in step 3 1-ethynyl-4-fluoro-2-(trifluoromethyl)benzene (Int 1/6) in place of 1-ethynyl-2-methylbenzene.

Intermediate 2/10: tert-Butyl 6-chloro-2-(2-(difluoromethyl)phenyl)-1H-pyrrolo[2,3-b]pyridine-1-carboxylate (Int 2/10)

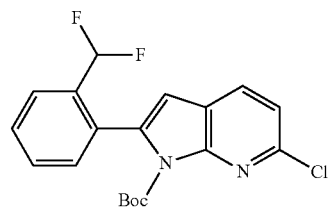 [SMILES: CC(C)(C)OC(=O)n1c(-c2ccccc2C(F)F)cc2ccc(Cl)nc21]

The title compound was prepared similar as described for Intermediate 2 using in step 3 1-(difluoromethyl)-2-ethynylbenzene (Int 1/7) in place of 1-ethynyl-2-methylbenzene.

Intermediate 2/11: tert-Butyl 6-chloro-2-(2,3-dihydro-1H-inden-4-yl)-1H-pyrrolo[2,3-b]pyridine-1-carboxylate (Int 2/11)

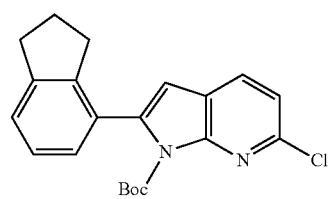 [SMILES: CC(C)(C)OC(=O)n1c(-c2cccc3c2CCC3)cc2ccc(Cl)nc21]

The title compound was prepared similar as described for Intermediate 2 using in step 3 4-ethynyl-2,3-dihydro-1H-indene (Int 1/8) in place of 1-ethynyl-2-methylbenzene.

Intermediate 2/12: tert-Butyl 6-chloro-2-(3-(trifluoromethyl)pyridin-2-yl)-1H-pyrrolo[2,3-b]pyridine-1-carboxylate (Int 2/12)

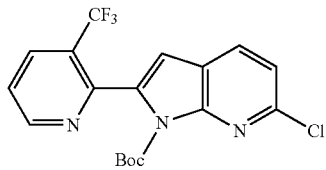 [SMILES: CC(C)(C)OC(=O)n1c(-c2ncccc2C(F)(F)F)cc2ccc(Cl)nc21]

The title compound was prepared similar as described for Intermediate 2 using in step 3 2-ethynyl-3-(trifluoromethyl)pyridine (Int 1/9) in place of 1-ethynyl-2-methylbenzene.

Intermediate 2/13: tert-Butyl 6-chloro-2-(2-methoxyphenyl)-1H-pyrrolo[2,3-b]pyridine-1-carboxylate (Int 2/13)

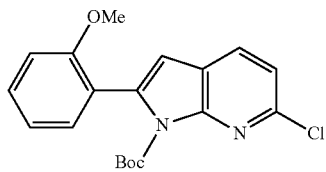 [SMILES: COc1ccccc1-c1cc2ccc(Cl)nc2n1C(=O)OC(C)(C)C]

The title compound was prepared similar as described for Intermediate 2 using in step 3 1-ethynyl-2-methoxybenzene in place of 1-ethynyl-2-methylbenzene.

Intermediate 2/14: tert-Butyl 6-chloro-2-(2-(methylsulfonyl)phenyl)-1H-pyrrolo[2,3-b]pyridine-1-carboxylate (Int 2/14)

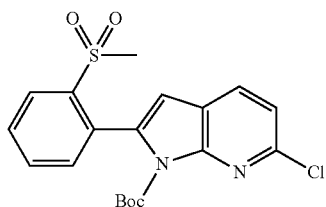 [SMILES: CC(C)(C)OC(=O)n1c(-c2ccccc2S(C)(=O)=O)cc2ccc(Cl)nc21]

The title compound was prepared similar as described for Intermediate 2 using in step 3 1-ethynyl-2-(methylsulfonyl)benzene (Int 1/10) in place of 1-ethynyl-2-methylbenzene.

Intermediate 2/15: tert-Butyl 6-chloro-2-(3-(difluoromethyl)phenyl)-1H-pyrrolo[2,3-b]pyridine-1-carboxylate (Int 2/15)

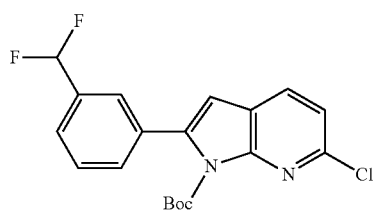 [SMILES: CC(C)(C)OC(=O)n1c(-c2cccc(C(F)F)c2)cc2ccc(Cl)nc21]

The title compound was prepared similar as described for Intermediate 2 using in step 3 1-(difluoromethyl)-3-ethynylbenzene (Int 1/12) in place of 1-ethynyl-2-methylbenzene.

Intermediate 2/16: tert-Butyl 6-chloro-2-(4-(difluoromethyl)phenyl)-1H-pyrrolo[2,3-b]pyridine-1-carboxylate (Int 2/16)

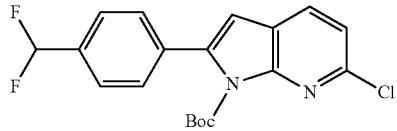 [SMILES: CC(C)(C)OC(=O)n1c(-c2ccc(C(F)F)cc2)cc2ccc(Cl)nc21]

The title compound was prepared similar as described for Intermediate 2 using in step 3 1-(difluoromethyl)-4-ethynylbenzene (Int 1/13) in place of 1-ethynyl-2-methylbenzene.

Intermediate 2/17: tert-Butyl 6-chloro-2-(5-chloro-2-(trifluoromethyl)phenyl)-1H-pyrrolo[2,3-b]pyridine-1-carboxylate (Int 2/17)

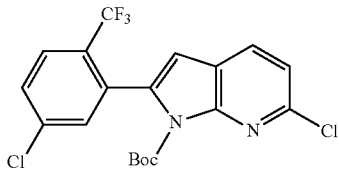 [SMILES: CC(C)(C)OC(=O)n1c(-c2cc(Cl)ccc2C(F)(F)F)cc2ccc(Cl)nc21]

The title compound was prepared similar as described for Intermediate 2 using in step 3 4-chloro-2-ethynyl-1-(trifluoromethyl)benzene (Int 1/14) in place of 1-ethynyl-2-methylbenzene.

Intermediate 2/18: tert-Butyl 2-(2,5-bis(trifluoromethyl)phenyl)-6-chloro-1H-pyrrolo[2,3-b]pyridine-1-carboxylate (Int 2/18)

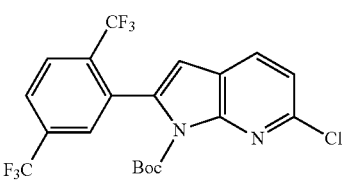

The title compound was prepared similar as described for Intermediate 2 using in step 3 2-ethynyl-1,4-bis(trifluoromethyl)benzene (Int 1/15) in place of 1-ethynyl-2-methylbenzene.

Intermediate 2/19: tert-Butyl 6-chloro-2-(5-methyl-2-(trifluoromethyl)phenyl)-1H-pyrrolo[2,3-b]pyridine-1-carboxylate (Int 2/19)

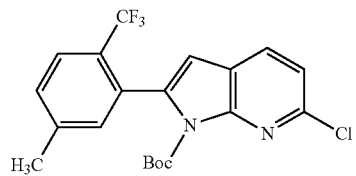

The title compound was prepared similar as described for Intermediate 2 using in step 3 2-ethynyl-4-methyl-1-(trifluoromethyl)benzene (Int 1/17) in place of 1-ethynyl-2-methylbenzene.

Intermediate 2/20: tert-Butyl 6-chloro-2-(5-chloro-2-(difluoromethyl)phenyl)-1H-pyrrolo[2,3-b]pyridine-1-carboxylate (Int 2/20)

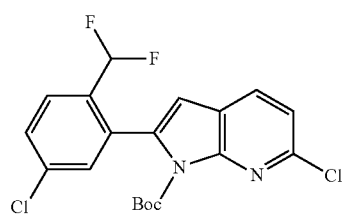 [SMILES: CC(C)(C)OC(=O)n1c(-c2cc(Cl)ccc2C(F)F)cc2ccc(Cl)nc21]

The title compound was prepared similar as described for Intermediate 2 using in step 3 4-chloro-1-(difluoromethyl)-2-ethynylbenzene (Int 1/18) in place of 1-ethynyl-2-methylbenzene.

Intermediate 2/21: tert-Butyl 6-chloro-2-(2-(difluoromethyl)-5-methylphenyl)-1H-pyrrolo[2,3-b]pyridine-1-carboxylate (Int 2/21)

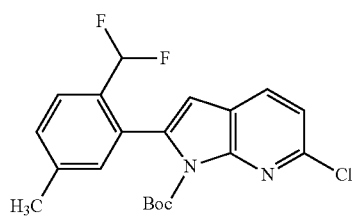

The title compound was prepared similar as described for Intermediate 2 using in step 3 1-(difluoromethyl)-2-ethynyl-4-methylbenzene (Int 1/19) in place of 1-ethynyl-2-methylbenzene.

Intermediate 3: 1-Methyl-1H-1,2,4-triazole-5-carboxamide (Int 3)

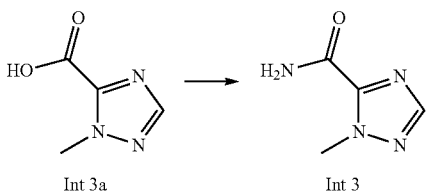

A mixture of 1-methyl-1H-1,2,4-triazole-5-carboxylic acid (7.0 g, 55.1 mmol) in SOCl$_2$ (20 mL) was heated to 70° C. for 2 h. The mixture was concentrated to dryness. The residue was dissolved in NH$_3$/MeOH (7M, 40 mL) and stirred at rt overnight. The precipitated solid was filtered off, extracted with Et$_2$O and dried under reduced pressure to give the title compound.

Intermediate 3/1: Furo[2,3-c]pyridine-5-carboxamide (Int 3/1)

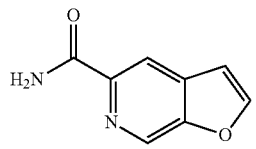 [SMILES: NC(=O)c1cc2ccoc2cn1]

The title compound was prepared similar as described for Intermediate 3 using furo[2,3-c]pyridine-5-carboxylic acid in place of 1-methyl-1H-1,2,4-triazole-5-carboxylic acid.

Intermediate 3/2: 4-Methyl-1,2,5-oxadiazole-3-carboxamide (Int 3/2)

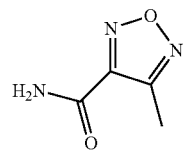

The title compound was prepared similar as described for Intermediate 3 using 4-methyl-1,2,5-oxadiazole-3-carboxylic acid in place of 1-methyl-1H-1,2,4-triazole-5-carboxylic acid.

Intermediate 3/3: Methyl 5-carbamoyl-1-methyl-1H-pyrazole-3-carboxylate (Int 3/3)

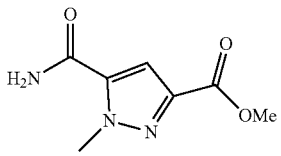

The title compound was prepared similar as described for Intermediate 3 using 3-(methoxycarbonyl)-1-methyl-1H-pyrazole-5-carboxylic acid in place of 1-methyl-1H-1,2,4-triazole-5-carboxylic acid.

Intermediate 4:
4-Methyl-4H-1,2,4-triazole-3-carboxamide (Int 4)

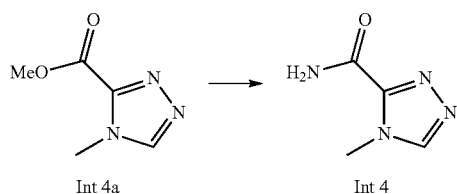

A mixture of methyl 4-methyl-4H-1,2,4-triazole-3-carboxylate (Int 4a) (900 mg, 6.38 mmol) in NH$_3$/MeOH (7M, 15 mL) was stirred overnight at 65° C. in a sealed tube. The mixture was concentrated to half of its volume. A precipitate formed, which was filtered off, extracted with Et$_2$O and dried under reduced pressure to give the title compound.

Intermediate 5: 6-Chloro-1-methyl-2-(2-(trifluoromethyl)phenyl)-1H-pyrrolo[2,3-b]pyridine (Int 5)

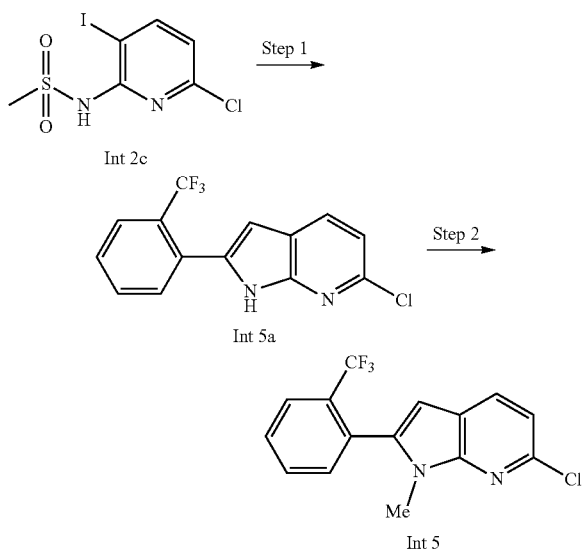

Step 1: 6-Chloro-2-(2-(trifluoromethyl)phenyl)-1H-pyrrolo[2,3-b]pyridine (Int 5a)

The title compound was prepared similar as described for Intermediate 2d, using in step 3 1-ethynyl-2-(trifluoromethyl)benzene in place of 1-ethynyl-2-methylbenzene.

Step 2: 6-Chloro-1-methyl-2-(2-(trifluoromethyl)phenyl)-1H-pyrrolo[2,3-b]pyridine (Int 5)

A mixture of 6-chloro-2-(2-(trifluoromethyl)phenyl)-1H-pyrrolo[2,3-b]pyridine (Int 5a) (500 mg, 1.69 mmol), potassium carbonate (350 mg, 2.54 mmol) and MeI (288 mg, 2.03 mmol) in THF (15 mL) was stirred at rt overnight. The mixture was concentrated to dryness and the residue was purified by reverse phase chromatography (c18, gradient 25-55% acetonitrile/10 mM aqueous NH$_4$HCO$_3$) to give the title compound as a white solid.

Intermediate 6: Methyl 2-(6-chloro-1-(methylsulfonyl)-1H-pyrrolo[2,3-b]pyridin-2-yl)benzoate (Int 6)

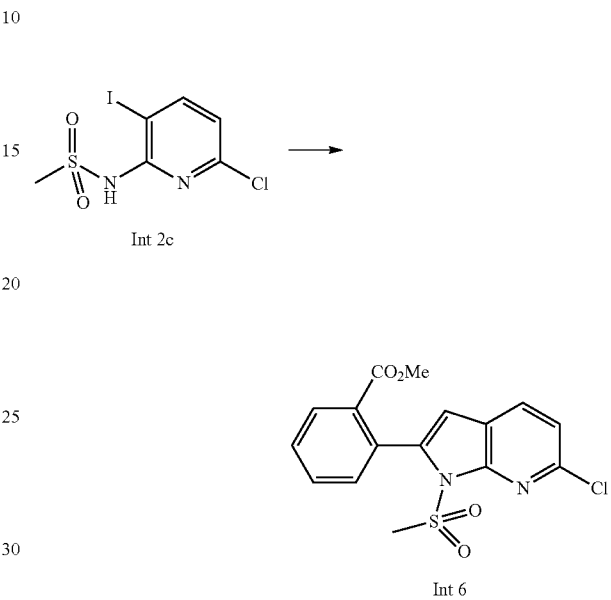

A mixture of N-(6-chloro-3-iodopyridin-2-yl)methanesulfonamide (1.00 g, 3.01 mmol) (Int 2c), methyl 2-ethynylbenzoate (510 mg, 3.19 mmol), bis(triphenylphosphine)palladium(II) dichloride (114 mg, 0.16 mmol), copper(I) iodide (30 mg, 0.16 mmol) and TEA (1.45 g, 14.38 mmol) in DMF (15 mL) was stirred under nitrogen at 100° C. for 3 h. The mixture was diluted with aqueous NH4Cl solution and extracted with EtOAc. The combined organic layers were dried over anhydrous MgSO4, filtered and concentrated to dryness. The residue was purified by silica gel chromatography (gradient 5-100% EtOAc in PE) to give the title compound as a yellow solid.

Intermediate 7:
1-Ethyl-11H-1,2,4-triazole-5-carboxamide (Int 7)

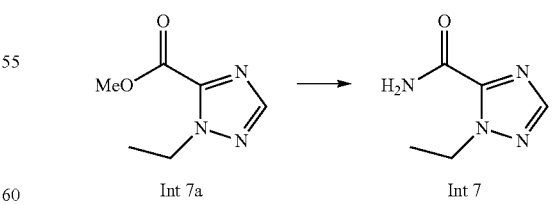

A mixture of methyl 1-ethyl-1H-1,2,4-triazole-5-carboxylate (Int 7a) (700 mg, 4.167 mmol) in aqueous NH$_3$ (25%, 10 mL) was stirred at rt overnight. The formed precipitate was filtered, washed with water and dried to afford the desired title compound as a white solid.

Intermediate 8: tert-Butyl 6-chloro-2-(2-(difluoromethyl)furan-3-yl)-1H-pyrrolo[2,3-b]pyridine-1-carboxylate (Int 8)

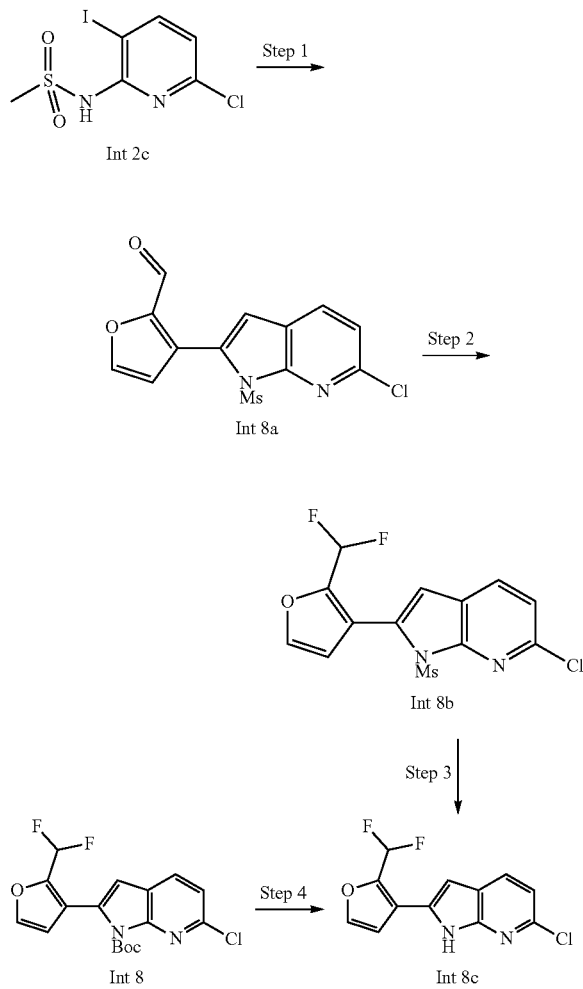

Step 1: 3-(6-Chloro-1-(methylsulfonyl)-1H-pyrrolo[2,3-b]pyridin-2-yl)furan-2-carbaldehyde (Int 8a)

A mixture of N-(6-chloro-3-iodopyridin-2-yl)methanesulfonamide (Int 2c) (692 mg, 2.08 mmol), 3-ethynylfuran-2-carbaldehyde (Int 1/16) (300 mg, 2.50 mmol), bis(triphenylphosphine) palladium (II) dichloride (73 mg, 0.10 mmol), copper (I) iodide (20 mg, 0.10 mmol) and TEA (947 mg, 9.37 mmol) in DMF (20 mL) was stirred at 80° C. for 3 h. The mixture was cooled to rt and diluted with aqueous NH₄Cl. The mixture was extracted with EtOAc and the combined organic layers were dried over anhydrous MgSO₄, filtered and concentrated to dryness. The residue was purified by silica gel chromatography (EtOAc/PE=1:10) to give the title compound as a yellow solid.

Step 2: 6-Chloro-2-(2-(difluoromethyl)furan-3-yl)-1-(methylsulfonyl)-1H-pyrrolo[2,3-b]pyridine (Int 8b)

DAST (411 mg, 4.62 mmol) was added to a mixture of 3-(6-chloro-1-(methylsulfonyl)-1H-pyrrolo[2,3-b]pyridin-2-yl)furan-2-carbaldehyde (Int 8a) (300 mg, 0.92 mmol) in dichloromethane (10 mL) at 0° C. and the mixture was stirred at rt for 12 h. The mixture was poured into saturated aqueous NaHCO₃ and extracted with EtOAc. The combined organic layers were concentrated to dryness to give the title compound as a yellow solid.

Step 3: 6-Chloro-2-(2-(difluoromethyl)furan-3-yl)-1H-pyrrolo[2,3-b]pyridine (Int 8c)

To a mixture of 6-chloro-2-(2-(difluoromethyl)furan-3-yl)-1-(methylsulfonyl)-1H-pyrrolo[2,3-b]pyridine (Int 8b) (165 mg, 0.48 mmol) in DMF (1.5 mL), was added DBU (1 mL) and the mixture was stirred at 70° C. overnight. The mixture was diluted with aqueous NH₄Cl and extracted with EtOAc. The combined organic layers were dried over anhydrous MgSO₄, filtered and concentrated to dryness. The residue was purified by silica gel chromatography (EtOAc/PE=1:8) to give the title compound as yellow solid.

Step 4: tert-Butyl 6-chloro-2-(2-(difluoromethyl)furan-3-yl)-1H-pyrrolo[2,3-b]pyridine-1-carboxylate (Int 8)

6-Chloro-2-(2-(difluoromethyl)furan-3-yl)-1H-pyrrolo[2,3-b]pyridine (Int 8c) (120 mg, 0.45 mmol) was suspended in DCM (2 mL). Boc₂O (345 mg, 1.58 mmol) dissolved in DCM (1 mL) was added, followed by DMAP (10 mg). After evolution of carbon dioxide had ceased the mixture was absorbed onto silica and purified by column chromatography (EtOAc/DCM=1:10) to give the title compound as a white solid.

Intermediate 9: 2-(2-(Difluoromethyl)-5-fluorophenyl)-4,4,5,5-tetramethyl-1,3,2-dioxaborolane (Int 9)

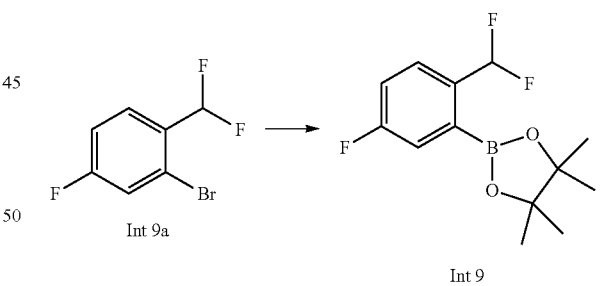

A mixture of 2-bromo-1-(difluoromethyl)-4-fluorobenzene (73 g, 0.287 mol), 4,4,4',4',5,5,5',5'-octamethyl-2,2'-bi(1,3,2-dioxaborolane) (88 g, 0.345 mol), Pd(dppf)Cl₂ (10.4 g, 0.014 mol) and KOAc (95.8 g, 0.978 mol) in 1,4-dioxane (700 mL) and DMSO (30 mL) was stirred at 85° C. under N₂ overnight. The mixture was quenched with water (250 mL) and extracted with EtOAc (3×500 mL). The combined organic layers were washed with brine, dried over anhydrous Na₂SO₄, filtered and concentrated to dryness.

The residue was purified by flash chromatography column on silica gel eluting with PE to give the title compound as a yellow oil.

Intermediate 20: 6-Chloro-2-(2-cyclopropylphenyl)-1-((2-(trimethylsilyl)ethoxy)methyl)-1H-pyrrolo[2,3-b]pyridin (Int 20)

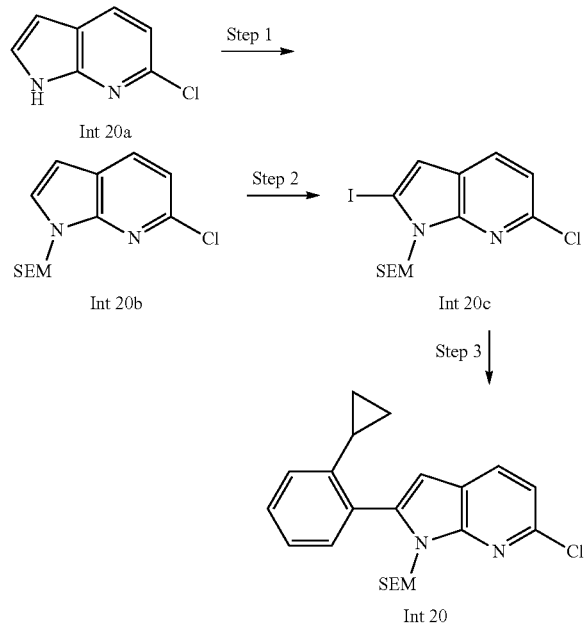

Step 1: 6-Chloro-1-((2-(trimethylsilyl)ethoxy)methyl)-1H-pyrrolo[2,3-b]pyridine (Int 20b)

To a solution of 6-chloro-1H-pyrrolo[2,3-b]pyridine (20.0 g, 131 mmol) in DMF (30 mL) was added NaH (7.88 g, 197 mmol) at 0° C. The mixture was stirred at rt for 1 h. SEMCl (32.8 g, 197 mmol) was added and the mixture was stirred at rt overnight. The mixture was diluted with water (500 mL) and extracted with DCM (3×300 mL). The combined organic layers were dried over anhydrous $Na_2SO_4$, filtered and concentrated to dryness. The residue was purified by column chromatography (PE/EA=20:1) to give the title compound as a yellow oil.

Step 2: 6-Chloro-2-iodo-1-((2-(trimethylsilyl)ethoxy)methyl)-1H-pyrrolo[2,3-b]pyridine (Int 20c)

To a solution of 6-chloro-1-((2-(trimethylsilyl)ethoxy)methyl)-1H-pyrrolo[2,3-b]pyridine (Int 20b) (20.0 g, 0.071 mol) in THF (300 mL) was added n-BuLi (42.4 mL, 2.5 M in hexane, 0.106 mol) at −78° C. and the mixture was stirred at the same temperature for 1 h. Then $I_2$ (23.3 g, 0.092 mol) in THF (40 mL) was added at −30° C. The mixture was stirred at rt overnight. Water (500 mL) was added and the mixture was extracted with DCM (3×600 mL). The combined organic layers were dried over anhydrous $Na_2SO_4$, filtered and concentrated to dryness. The residue was purified by column chromatography on silica gel (PE/E=100:1) to give the title compound as a brown solid.

Step 3: 6-Chloro-2-(2-cyclopropylphenyl)-1-((2-(trimethylsilyl)ethoxy)methyl)-1H-pyrrolo[2,3-b]pyridine (Int 20)

A mixture of 6-chloro-2-iodo-1-((2-(trimethylsilyl)ethoxy)methyl)-1H-pyrrolo[2,3-b]pyridine (Int 20c) (450 mg, 1.1 mmol), 2-(2-cyclopropylphenyl)-4,4,5,5-tetramethyl-1,3,2-dioxaborolane (350 mg, 1.43 mmol), Pd(dppf)$Cl_2$ (80 mg, 0.11 mmol) and $K_2CO_3$ (304 mg, 2.2 mmol) in 1,4-dioxane (6 mL) was stirred at 85° C. overnight under $N_2$. Water (50 mL) was added and the mixture was extracted with EtOAc (3×50 mL). The combined organic layers were dried over $Na_2SO_4$, filtered and concentrated to dryness. The residue was purified by column chromatography on silica gel (PE/EA=100:1) to give the title compound as a yellow oil.

Intermediates 20/1 to 20/8

The following Intermediates were prepared similar as described for Intermediate 20 using the appropriate Suzuki coupling building blocks.

| Int. # | Suzuki coupling building block | Structure |
|---|---|---|
| Int 20/1 | ![] | ![] |
| Int 20/2 | ![] | ![] |

-continued

| Int. # | Suzuki coupling building block | Structure |
|---|---|---|
| Int 20/3 | 2-(pinacol boronate)-4-fluorobenzonitrile | 2-(2-cyano-5-fluorophenyl)-6-chloro-1-SEM-7-azaindole |
| Int 20/4 | 2-(difluoromethyl)phenyl boronic acid pinacol ester | 2-(2-(difluoromethyl)phenyl)-6-chloro-1-SEM-7-azaindole |
| Int 20/5 | methyl 3-boronobenzoate | methyl 3-(6-chloro-1-SEM-7-azaindol-2-yl)benzoate |
| Int 20/6 | methyl 4-boronobenzoate | methyl 4-(6-chloro-1-SEM-7-azaindol-2-yl)benzoate |
| Int 20/7 | 5-cyano-2-(trifluoromethyl)phenyl boronic acid pinacol ester | 2-(5-cyano-2-(trifluoromethyl)phenyl)-6-chloro-1-SEM-7-azaindole |
| Int 20/8 Int 9 | 2-(difluoromethyl)-5-fluorophenyl boronic acid pinacol ester | 2-(2-(difluoromethyl)-5-fluorophenyl)-6-chloro-1-SEM-7-azaindole |

Intermediate 21: 3,6-Dichloro-2-(2-(difluoromethyl) phenyl)-1-((2-(trimethylsilyl) ethoxy)methyl)-1H-pyrrolo[2,3-b]pyridine (Int 21)

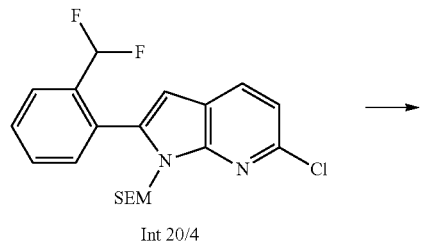

Int 20/4

→

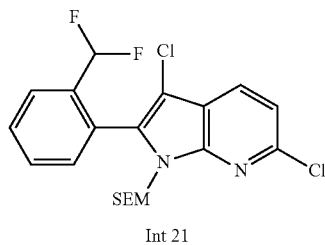

Int 21

To a solution of 6-chloro-2-(2-(difluoromethyl)phenyl)-1-((2-(trimethylsilyl)ethoxy) methyl)-1H-pyrrolo[2,3-b]pyridine (Int 20/4) (205 mg, 0.46 mmol) in DMF (2 mL) NCS (81 mg, 0.61 mmol) was added. The mixture was stirred at 80° C. overnight. The mixture was concentrated to dryness and the residue was purified by column chromatography (gradient MeCN/H$_2$O=5% to 95%) to afford the title compound as a white solid.

Intermediate 22: 6-Chloro-2-(2-(difluoromethyl) phenyl)-3-fluoro-1-((2-(trimethylsilyl) ethoxy) methyl)-1H-pyrrolo[2,3-b]pyridine (Int 22)

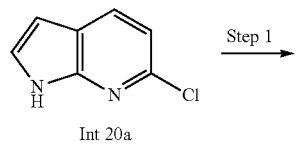

Int 20a

Step 1 →

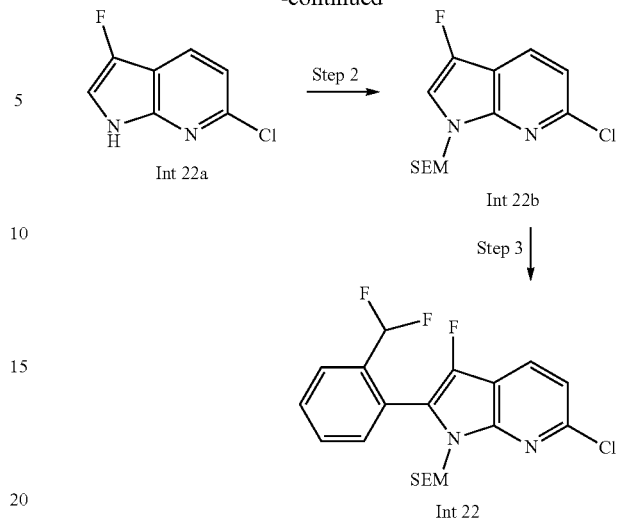

Step 1: 6-Chloro-3-fluoro-1H-pyrrolo[2,3-b]pyridine (Int 22a)

To a solution of 6-chloro-1H-pyrrolo[2,3-b]pyridine (Int 20a) (2.0 g, 13.16 mmol) in DMF (8 mL) and acetonitrile (20 mL) was added Selectfluor (6.96 g, 19.66 mmol) at rt under N$_2$ atmosphere. The mixture was stirred at rt overnight. The mixture was diluted with H$_2$O (20 mL) and extracted with EtOAc (3×20 mL). The combined organic layers were dried over anhydrous Na$_2$SO$_4$, filtered and concentrated to dryness. The residue was purified by silica gel column chromatography (PE/EtOAc=49:1) to afford the title compound as a white solid.

Step 2: 6-Chloro-3-fluoro-1-((2-(trimethylsilyl) ethoxy)methyl)-1H-pyrrolo[2,3-b]pyridine (Int 22b)

To a solution of 6-chloro-3-fluoro-1H-pyrrolo[2,3-b]pyridine (Int 22a) (300 mg, 1.77 mmol) in DMF (3 mL) was added NaH (142 mg, 3.53 mmol) at 0° C. After stirring at the same temperature for 30 min SEMCl (442 mg, 2.65 mmol) was added and the mixture was stirred at rt overnight. The mixture was concentrated to dryness and the residue was purified by column chromatography on silica gel (PE/EtOAc=49:1) to afford the title compound as a yellow oil.

Step 3: 6-Chloro-2-(2-(difluoromethyl)phenyl)-3-fluoro-1-((2-(trimethylsilyl)ethoxy) methyl)-1H-pyrrolo[2,3-b]pyridine (Int 22)

To a solution of 6-chloro-3-fluoro-1-((2-(trimethylsilyl) ethoxy)methyl)-1H-pyrrolo[2,3-b]pyridine (Int 22b) (160 mg, 0.533 mmol), 1-bromo-2-(difluoromethyl)benzene (133 mg, 0.64 mmol) and PPh$_3$ (8 mg, 0.03 mmol) in DMF (2 mL) was added Pd(OAc)$_2$ (16 mg, 0.07 mmol) and KOAc (105 mg, 1.07 mmol). The mixture was stirred at 125° C. overnight under N$_2$ atmosphere. The mixture was filtered and the residue was extracted with EtOAc (20 mL). The filtrate was concentrated to dryness and the residue was purified by column chromatography on silica gel (PE/EtOAc=49:1) to afford the title compound as a yellow oil.

Intermediate 23: tert-Butyl 6-chloro-2-(5-cyclopropyl-2-(trifluoromethyl)phenyl)-1H-pyrrolo[2,3-b]pyridine-1-carboxylate (Int 23)

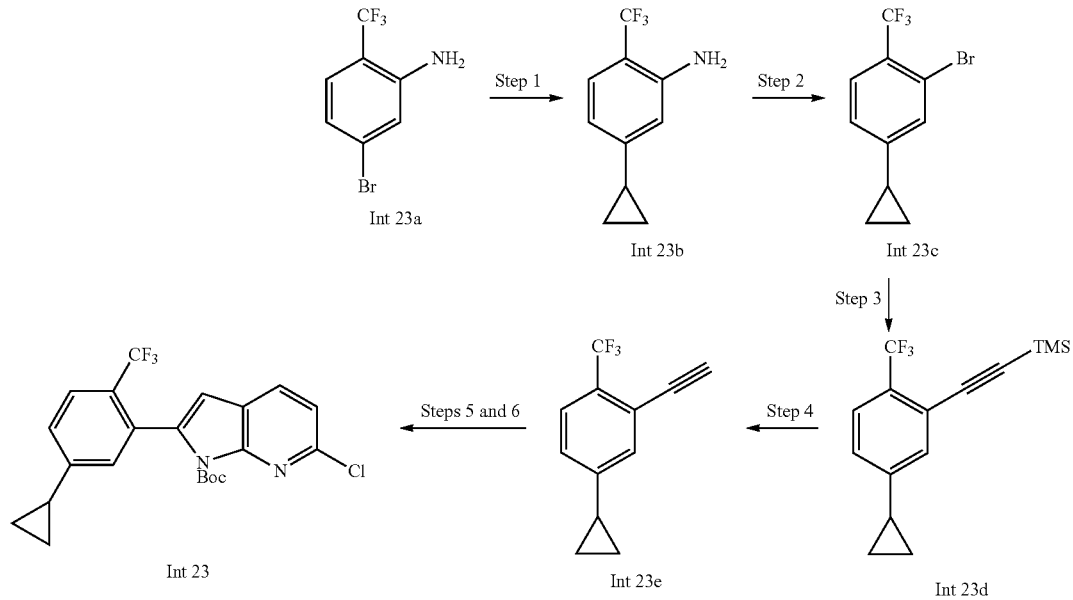

Step 1: 5-Cyclopropyl-2-(trifluoromethyl)aniline (Int 23b)

Pd(dppf)Cl$_2$ (613 mg, 0.84 mmol) was added to a mixture of 5-bromo-2-(trifluoromethyl)aniline (Int 23a) (2.00 g, 8.37 mmol), cyclopropylboronic acid (929 mg, 12.56 mmol) and Na$_2$CO$_3$ (1.77 g, 16.70 mmol) in dioxane (25 mL) and the mixture was stirred at 90° C. overnight. The mixture was concentrated to dryness and the residue was purified by column chromatography (0-2% EtOAc in PE) to give the title compound as yellow oil.

Step 2: 2-Bromo-4-cyclopropyl-1-(trifluoromethyl)benzene (Int 23c)

tert-Butyl nitrite (1.69 g, 16.41 mmol) was quickly added to a solution of 5-cyclopropyl-2-(trifluoromethyl)aniline (Int 23b) (1.10 g, 5.47 mmol) in CH$_3$CN (50 mL) and the mixture was stirred at rt under N$_2$ for 2 min. CuBr$_2$ (3.02 g, 13.66 mmol) was added and the mixture was stirred at rt under N$_2$ for 3 h. Water (20 mL) was added and the mixture was extracted with EtOAc (2×50 mL). The combined organic layers were concentrated to dryness and the residue was purified by column chromatography (0-2% DCM in PE) to give the title compound as colorless oil.

Step 3: ((5-Cyclopropyl-2-(trifluoromethyl)phenyl)ethynyl)trimethylsilane (Int 23d)

To a mixture of Pd(PPh$_3$)$_4$ (307 mg, 0.26 mmol) and CuI (101 mg, 0.53 mmol) in TEA (20 mL) was added 2-bromo-4-cyclopropyl-1-(trifluoromethyl)benzene (Int 23c) (1.40 g, 5.28 mmol) and ethynyl trimethylsilane (1.82 g, 18.57 mmol). The mixture was stirred at 70° C. overnight. The mixture was concentrated and EtOAc (80 mL) was added. The mixture was filtered through Celite®. The filtrate was concentrated to dryness and the residue was purified by column chromatography (PE) to give the title compound as colorless oil.

Step 4: 4-Cyclopropyl-2-ethynyl-1-(trifluoromethyl)benzene (Int 23e)

To a solution of ((5-cyclopropyl-2-(trifluoromethyl)phenyl)ethynyl)trimethylsilane (Int 23d) in MeOH (5 mL) was added K$_2$CO$_3$ (582 mg, 4.22 mmol) and the mixture was stirred at rt for 0.5 h. The mixture was poured into ice-water and extracted with diethyl ether (2×30 mL). The combined organic layers were dried over anhydrous MgSO$_4$, filtered and concentrated to dryness to afford the title compound.

Steps 5-6: tert-Butyl 6-chloro-2-(5-cyclopropyl-2-(trifluoromethyl)phenyl)-1H-pyrrolo[2,3-b]pyridine-1-carboxylate (Int 23)

The title compound was prepared similar as described for Intermediate 2 steps 3 and 4 using in step 34-cyclopropyl-1-ethynyl-2-(trifluoromethyl)benzene (Int 23e) in place of 1-ethynyl-2-methylbenzene.

Intermediate 23/1: tert-Butyl 6-chloro-2-(5-ethyl-2-(trifluoromethyl)phenyl)-1H-pyrrolo[2,3-b]pyridine-1-carboxylate (Int 23/1)

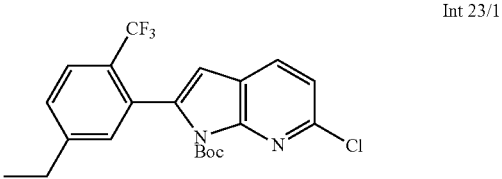 [SMILES: CCc1ccc(C(F)(F)F)c(-c2cc3ccc(Cl)nc3n2C(=O)OC(C)(C)C)c1]

The title compound was prepared similar as described for Intermediate 23 using in step 1 ethylboronic acid in place of cyclopropylboronic acid.

Intermediate 24: tert-Butyl 6-chloro-2-(2-(difluoromethyl)-4,5-difluorophenyl)-1H-pyrrolo[2,3-b]pyridine-1-carboxylate (Int 24)

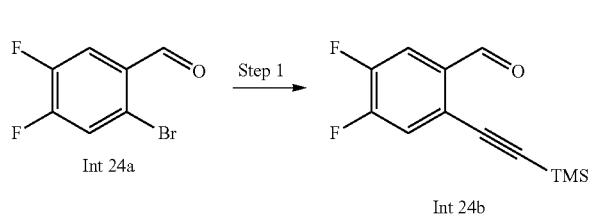

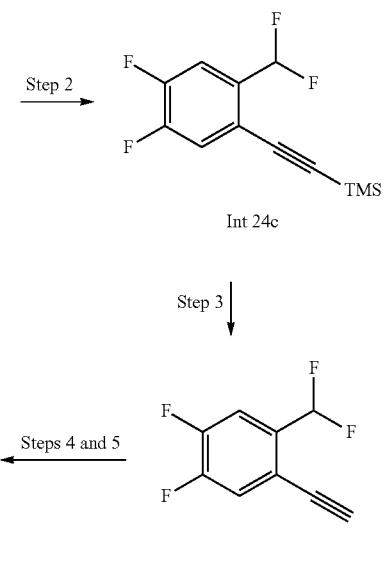

Step 1: 4,5-Difluoro-2-((trimethylsilyl)ethynyl)benzaldehyde (Int 24b)

A mixture of Pd(PPh$_3$)$_4$ (260 mg, 0.23 mmol), CuI (43 mg, 0.23 mmol), 2-bromo-4,5-difluorobenzaldehyde (1.00 g, 4.50 mmol) and ethynyl trimethylsilane (1.55 g, 15.80 mmol) in TEA (10 mL) was stirred at 70° C. overnight. The mixture was concentrated to dryness. EtOAc (20 mL) was added and the mixture was filtered through a pad of Celite®. The mixture was concentrated to dryness and the residue was purified by column chromatography (gradient 5-30% EtOAc in PE) to give the title compound as a yellow oil.

Step 2: ((2-(Difluoromethyl)-4,5-difluorophenyl)ethynyl)trimethylsilane (Int 24c)

To a solution of 4,5-difluoro-2-((trimethylsilyl)ethynyl)benzaldehyde (Int 24b) (1.67 g, 7.00 mmol) in DCM (10 mL) was added DAST (2.25 g, 14.00 mmol) at 0° C. and the mixture was stirred at rt for 4 h. The mixture was poured into ice-water and extracted with DCM (2×30 mL). The combined organic layers were dried over anhydrous MgSO$_4$, filtered and concentrated to dryness. The residue was purified by column chromatography (gradient 5-30% EtOAc in PE) to give the title compound as a yellow oil.

Step 3: 1-(Difluoromethyl)-2-ethynyl-4,5-difluorobenzene (Int 24d)

To a solution of ((2-(difluoromethyl)-4,5-difluorophenyl)ethynyl)trimethylsilane (Int 24c) (1.30 g, 5.00 mmol) in MeOH (2 mL) was added K$_2$CO$_3$ (1.38 g, 10.00 mmol) and the mixture was stirred at rt for 0.5 h. The mixture was poured into ice-water and extracted with diethyl ether (2×10 mL). The combined organic layers were dried over anhydrous MgSO$_4$, filtered and concentrated to dryness to give the title compound.

Steps 4-5: tert-Butyl 6-chloro-2-(2-(difluoromethyl)-4,5-difluorophenyl)-1H-pyrrolo[2,3-b]pyridine-1-carboxylate (Int 24)

The title compound was prepared similar as described for Intermediate 2 steps 3 and 4 using in step 3 1-(difluoromethyl)-2-ethynyl-4,5-difluorobenzene (Int 24d) in place of 1-ethynyl-2-methylbenzene.

Intermediate 25: tert-Butyl 6-chloro-5-methyl-2-(2-(trifluoromethyl)phenyl)-1H-pyrrolo[2,3-b]pyridine-1-carboxylate (Int 25)

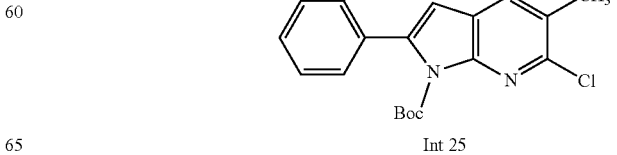

Step 1: 6-Chloro-3-iodo-5-methylpyridin-2-amine (Int 25b)

NIS (5.30 g, 23.56 mmol) was added to a stirred mixture of 6-chloro-5-methylpyridin-2-amine (Int 25a) (2.50 g, 17.60 mmol) in THF (30 mL) and stirring was continued at 0° C. for 30 min. The mixture was then heated at 50° C. for 24 h with additional NIS (5.30 g, 23.56 mmol) being added. The mixture was allowed to cool to rt and concentrated to dryness. Water (30 mL) was added and the mixture was extracted with ethyl acetate (3×40 mL). The combined organic layers were dried over anhydrous MgSO$_4$, filtered and concentrated to dryness. The residue was purified by silica gel chromatography (gradient 0-50% EtOAc in PE) to give the title compound as a white solid.

Steps 2-5: tert-Butyl 6-chloro-5-methyl-2-(2-(trifluoromethyl)phenyl)-1H-pyrrolo[2,3-b]pyridine-1-carboxylate (Int 25)

The title compound was prepared similar as described for Intermediate 2, Steps 1 to 4 using in Step 1 6-chloro-3-iodo-5-methylpyridin-2-amine (Int 25b) in place of 6-chloro-3-iodopyridin-2-amine and in Step 3 1-ethynyl-2-(trifluoromethyl)benzene in place of 1-ethynyl-2-methylbenzene.

Example 1: 1-Methyl-N-(2-(o-tolyl)-1H-pyrrolo[2,3-b]pyridin-6-yl)-1H-pyrazole-5-carboxamide (1)

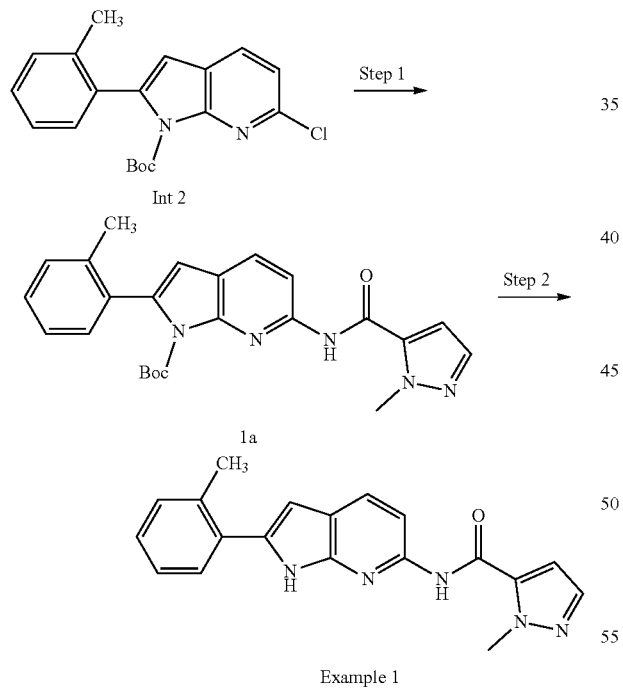

Example 1

Step 1: tert-Butyl 6-(1-methyl-1H-pyrazole-5-carboxamido)-2-(o-tolyl)-1H-pyrrolo[2,3-b]pyridine-1-carboxylate (1a)

Pd$_2$(dba)$_3$ (460 mg, 0.50 mmol) was added to a mixture of tert-butyl 6-chloro-2-(o-tolyl)-1H-pyrrolo[2,3-b]pyridine-1-carboxylate (Int 2) (340 mg, 0.99 mmol), potassium phosphate (693 mg, 3.28 mmol), 1-methyl-1H-pyrazole-5-carboxamide (250 mg, 2.0 mmol) and tBuXPhos (300 mg, 0.70 mmol) in a mixture of t-BuOH (6.0 mL) and water (0.2 mL). The mixture was heated at 90° C. for 3 h under microwave irradiation. The mixture was filtered and the residue washed with DCM (20 ml). The filtrate was concentrated to dryness and the residue was purified by column chromatography (gradient 5-100% EtOAc in PE) to give the title compound as a yellow solid.

Step 2: 1-Methyl-N-(2-(o-tolyl)-1H-pyrrolo[2,3-b]pyridin-6-yl)-1H-pyrazole-5-carboxamide (1)

To a mixture of tert-butyl 6-(1-methyl-1H-pyrazole-5-carboxamido)-2-(o-tolyl)-1H-pyrrolo[2,3-b]pyridine-1-carboxylate (1a) (314 mg, 0.73 mmol) in DCM (10 mL) was added TFA (2 mL) and the mixture was stirred at rt overnight. The mixture was diluted with aqueous NaHCO$_3$ solution. The aqueous layer was extracted with DCM. The combined organic layers were dried over anhydrous Mg$_2$SO$_4$, filtered and concentrated to dryness. The residue was purified by column chromatography (gradient 5-100% EtOAc in PE) to give the title compound as a white solid. $^1$H NMR (400 MHz, DMSO-d$_6$): δ ppm 8.85 (s, 1H), 8.27 (s, 1H), 8.11 (d, J=8.4 Hz, 1H), 7.99 (d, J=8.4 Hz, 1H), 7.50 (d, J=2.0 Hz, 1H), 7.49-7.45 (m, 1H), 7.33-7.27 (m, 3H), 6.63 (d, J=2.0 Hz, 1H), 6.56 (d, J=2.0 Hz, 1H), 4.26 (s, 3H), 2.51 (s, 3H). (ESI): m/z 332.2 [M+H]$^+$.

Example 1/1: 1-Methyl-N-(2-(2-(trifluoromethyl)phenyl)-1H-pyrrolo[2,3-b]pyridin-6-yl)-1H-pyrazole-5-carboxamide (1/1)

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 1). $^1$H NMR (500 MHz, DMSO-de): δ ppm 11.82 (s, 1H), 10.65 (s, 1H), 8.03 (d, J=6.8 Hz, 1H), 7.91 (d, J=8.0 Hz, 1H), 7.85 (d, J=8.5 Hz, 1H), 7.81-7.78 (m, 1H), 7.71-7.66 (m, 2H), 7.53 (d, J=2.5 Hz, 1H), 7.26 (d, J=2.0 Hz, 1H), 6.55 (s, 1H), 4.12 (s, 3H). (ESI): m/z 385.9 [M+H]$^+$.

Example 1/2: 1-Methyl-N-(2-(3-(trifluoromethyl)phenyl)-1H-pyrrolo[2,3-b]pyridin-6-yl)-1H-pyrazole-5-carboxamide (1/2)

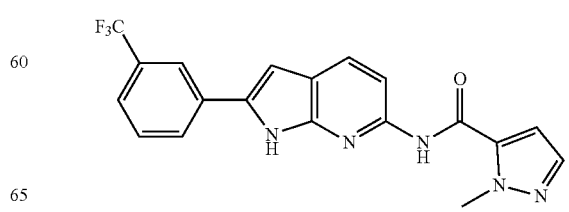

The title compound was prepared similar as described for Example 1 using in step 1 tert-butyl 6-chloro-2-(3-(trifluoromethyl)phenyl)-1H-pyrrolo[2,3-b]pyridine-1-carboxylate (Int 2/2) in place of tert-butyl 6-chloro-2-(o-tolyl)-1H-pyrrolo[2,3-b]pyridine-1-carboxylate (Int 2). $^1$H NMR (500 MHz, DMSO-d$_6$): δ ppm 12.13 (s, 1H), 10.58 (s, 1H), 8.31 (s, 1H), 8.24-8.22 (m, 1H), 8.01 (d, J=8.5 Hz, 1H), 7.80 (d, J=8.5 Hz, 1H), 7.70-7.67 (m, 2H), 7.54 (s, 1H), 7.23 (d, J=2.0 Hz, 1H), 7.13 (d, J=2.0 Hz, 1H), 4.12 (s, 3H). (ESI): m/z 385.9 [M+H]$^+$.

Example 1/3: 1-Methyl-N-(2-(2-(trifluoromethyl)pyridin-3-yl)-1H-pyrrolo[2,3-b]pyridin-6-yl)-1H-pyrazole-5-carboxamide (1/3)

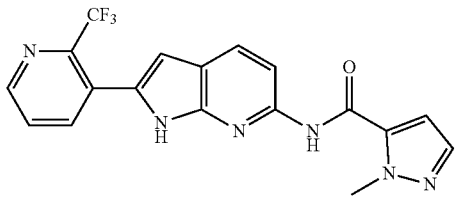 [SMILES: Cn1nccc1C(=O)Nc1ccc2cc(-c3cccnc3C(F)(F)F)[nH]c2n1]

The title compound was prepared similar as described for Example 1 using in step 1 tert-butyl 6-chloro-2-(2-(trifluoromethyl)pyridin-3-yl)-1H-pyrrolo[2,3-b]pyridine-1-carboxylate (Int 2/3) in place of tert-butyl 6-chloro-2-(o-tolyl)-1H-pyrrolo[2,3-b]pyridine-1-carboxylate (Int 2). $^1$H NMR (500 MHz, DMSO-d$_6$): δ ppm 11.91 (s, 1H), 10.67 (s, 1H), 8.82-8.81 (m, 1H), 8.20 (d, J=8.0 Hz, 1H), 8.06 (d, J=8.5 Hz, 1H), 7.89-7.85 (m, 2H), 7.53 (d, J=2.0 Hz, 1H), 7.26 (d, J=2.0 Hz, 1H), 6.63 (s, 1H), 4.12 (s, 3H). (ESI): m/z 386.9 [M+H]$^+$.

Example 1/4: 1-Methyl-N-(2-(2-(trifluoromethoxy)phenyl)-1H-pyrrolo[2,3-b]pyridin-6-yl)-1H-pyrazole-5-carboxamide (1/4)

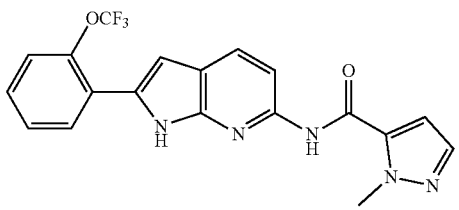 [SMILES: Cn1nccc1C(=O)Nc1ccc2cc(-c3ccccc3OC(F)(F)F)[nH]c2n1]

The title compound was prepared similar as described for Example 1 using in step 1 tert-butyl 6-chloro-2-(2-(trifluoromethoxy)phenyl)-1H-pyrrolo[2,3-b]pyridine-1-carboxylate (Int 2/4) in place of tert-butyl 6-chloro-2-(o-tolyl)-1H-pyrrolo[2,3-b]pyridine-1-carboxylate (Int 2). $^1$H NMR (500 MHz, DMSO-d$_6$): δ ppm 11.89 (s, 1H), 10.60 (s, 1H), 8.06 (d, J=8.5 Hz, 1H), 7.96-7.94 (m, 1H), 7.81 (d, J=8.5 Hz, 1H), 7.55-7.51 (m, 4H), 7.25 (s, 1H), 6.83 (d, J=2.0 Hz, 1H), 4.12 (s, 3H). (ESI): m/z 401.9 [M+H]$^+$.

Example 1/5: 1-Methyl-N-(2-(3-(trifluoromethoxy)phenyl)-1H-pyrrolo[2,3-b]pyridin-6-yl)-1H-pyrazole-5-carboxamide (1/5)

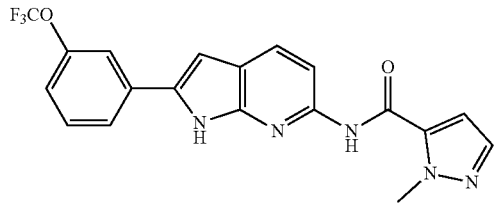 [SMILES: Cn1nccc1C(=O)Nc1ccc2cc(-c3cccc(OC(F)(F)F)c3)[nH]c2n1]

The title compound was prepared similar as described for Example 1 using in step 1 tert-butyl 6-chloro-2-(3-(trifluoromethoxy)phenyl)-1H-pyrrolo[2,3-b]pyridine-1-carboxylate (Int 2/5) in place of tert-butyl 6-chloro-2-(o-tolyl)-1H-pyrrolo[2,3-b]pyridine-1-carboxylate (Int 2). $^1$H NMR (500 MHz, DMSO-d$_6$): δ ppm 12.05 (s, 1H), 10.55 (s, 1H), 8.01-7.94 (m, 3H), 7.79 (d, J=8.5 Hz, 1H), 7.59 (dd J$_1$=J$_2$=8.0 Hz, 1H), 7.54 (s, 1H), 7.31 (d, J=8.5 Hz, 1H), 7.23 (s, 1H), 7.07 (s, 1H), 4.12 (s, 3H). (ESI): m/z 401.9 [M+H]$^+$.

Example 1/6: 1-Methyl-N-(2-(2-(trifluoromethyl)phenyl)-1H-pyrrolo[2,3-b]pyridin-6-yl)-1H-1,2,4-triazole-5-carboxamide (1/6)

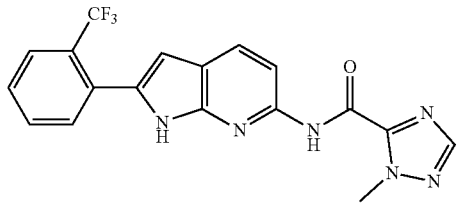

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.03 (s, 1H), 10.10 (s, 1H), 8.18 (s, 1H), 8.09 (d, J=8.5 Hz, 1H), 7.91-7.89 (m, 2H), 7.81-7.78 (m, 1H), 7.71-7.66 (m, 2H), 6.57 (s, 1H), 4.22 (s, 3H). (ESI): m/z 386.9 [M+H]$^+$.

Example 1/7: N-(2-(2-(Trifluoromethyl)phenyl)-1H-pyrrolo[2,3-b]pyridin-6-yl) picolinamide (1/7)

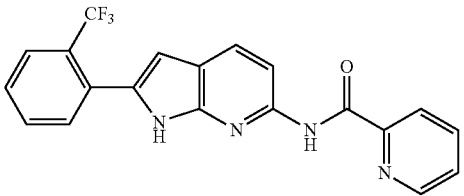 [SMILES: O=C(Nc1ccc2cc(-c3ccccc3C(F)(F)F)[nH]c2n1)c1ccccn1]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and picolinamide in place of 1-methyl-1H-pyrazole-5-carboxamide. ¹H NMR (500 MHz, DMSO-d₆): δ ppm 11.95 (s, 1H), 10.43 (s, 1H), 8.78 (d, J=4.0 Hz, 1H), 8.24 (d, J=8.0 Hz, 1H), 8.15-8.09 (m, 3H), 7.91 (d, J=7.5 Hz, 1H), 7.82-7-79 (m, 1H), 7.75-7.66 (m, 3H), 6.57 (s, 1H). (ESI): m/z 382.9 [M+H]⁺.

Example 1/8: 2-Fluoro-N-(2-(2-(trifluoromethyl)phenyl)-1H-pyrrolo[2,3-b]pyridin-6-yl)benzamide (1/8)

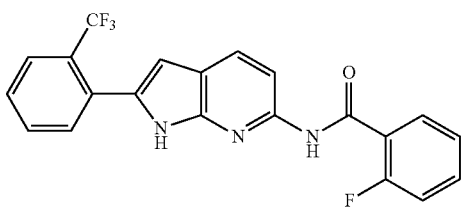 [SMILES: O=C(Nc1ccc2cc(-c3ccccc3C(F)(F)F)[nH]c2n1)c1ccccc1F]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and 2-fluorobenzamide in place of 1-methyl-1H-pyrazole-5-carboxamide. ¹H NMR (500 MHz, DMSO-d₆): δ ppm 11.89 (s, 1H), 10.60 (s, 1H), 8.05 (d, J=8.5 Hz, 1H), 7.97 (d, J=8.5 Hz, 1H), 7.90 (d, J=7.5 Hz, 1H), 7.79-7.67 (m, 4H), 7.60-7.57 (m, 1H), 7.36-7.32 (m, 2H), 6.54 (s, 1H). (ESI): m/z 399.9 [M+H]⁺.

Example 1/9: 4-Fluoro-N-(2-(2-(trifluoromethyl)phenyl)-1H-pyrrolo[2,3-b]pyridin-6-yl)benzamide (1/9)

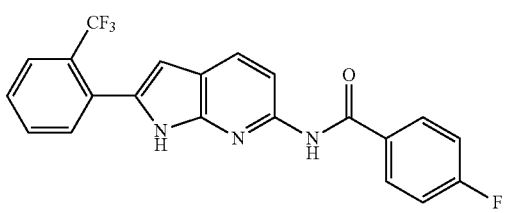 [SMILES: O=C(Nc1ccc2cc(-c3ccccc3C(F)(F)F)[nH]c2n1)c1ccc(F)cc1]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and 4-fluorobenzamide in place of 1-methyl-1H-pyrazole-5-carboxamide. ¹H NMR (500 MHz, DMSO-d₆): δ ppm 11.82 (s, 1H), 10.68 (s, 1H), 8.14-8.11 (m, 2H), 8.03 (d, J=8.5 Hz, 1H), 7.91-7.89 (m, 2H), 7.80-7.79 (m, 1H), 7.72-7.66 (m, 2H), 7.58 (s, 1H), 7.37-7.34 (m, 2H), 6.54 (s, 1H). (ESI): m/z 399.9 [M+H]⁺.

Example 1/10: N-(2-(2-(Trifluoromethyl)phenyl)-1H-pyrrolo[2,3-b]pyridin-6-yl) nicotinamide (1/10)

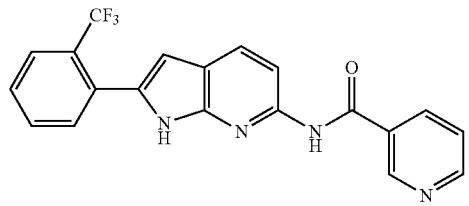 [SMILES: O=C(Nc1ccc2cc(-c3ccccc3C(F)(F)F)[nH]c2n1)c1cccnc1]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and nicotinamide in place of 1-methyl-1H-pyrazole-5-carboxamide. ¹H NMR (400 MHz, DMSO-d₆): δ ppm 11.85 (s, 1H), 10.92 (s, 1H), 9.16 (s, 1H), 8.77-8.75 (m, 1H), 8.38-8.35 (m, 1H), 8.05 (d, J=8.8 Hz, 1H), 7.95-7.90 (m, 2H), 7.82-7.79 (m, 1H), 7.72-7.57 (m, 2H), 7.56-7.54 (m, 1H), 6.55 (s, 1H). (ESI): m/z 382.9 [M+H]⁺.

Example 1/11: N-(2-(3-Fluoro-2-(trifluoromethyl)phenyl)-1H-pyrrolo[2,3-b]pyridin-6-yl)-1-methyl-1H-1,2,4-triazole-5-carboxamide (1/11)

The title compound was prepared similar as described for Example 1 using in step 1 tert-butyl 6-chloro-2-(3-fluoro-2-(trifluoromethyl)phenyl)-1H-pyrrolo[2,3-b]pyridine-1-carboxylate (Int 2/6) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. ¹H NMR (400 MHz, DMSO-d₆): δ ppm 12.09 (s, 1H), 10.11 (s, 1H), 8.18 (s, 1H), 8.09 (d, J=10.5 Hz, 1H), 7.90 (d, J=8.4 Hz, 1H), 7.86-7.80 (m, 1H), 7.64-7.59 (m, 1H), 7.49 (d, J=7.6 Hz, 1H), 6.54 (s, 1H), 4.22 (s, 3H). (ESI): m/z 405.1 [M+H]⁺.

Example 1/12: N-(2-(5-Fluoro-2-(trifluoromethyl)phenyl)-1H-pyrrolo[2,3-b]pyridin-6-yl)-1-methyl-1H-1,2,4-triazole-5-carboxamide (1/12)

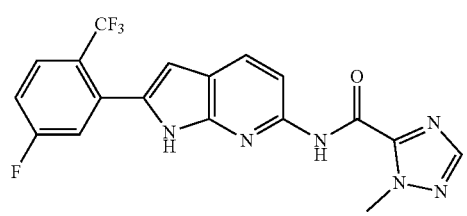 [SMILES: Cn1ncnc1C(=O)Nc1ccc2cc(-c3cc(F)ccc3C(F)(F)F)[nH]c2n1]

The title compound was prepared similar as described for Example 1 using in step 1 tert-butyl 6-chloro-2-(5-fluoro-2-(trifluoromethyl)phenyl)-1H-pyrrolo[2,3-b]pyridine-1-carboxylate (Int 2/7) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. ¹H NMR (500 MHz, DMSO-d₆): δ ppm 12.08 (s, 1H), 10.12 (s, 1H), 8.18 (s, 1H), 8.12 (d, J=8.0 Hz, 1H), 8.00-7.97 (m, 1H), 7.91 (d, J=8.5 Hz, 1H), 7.62-7.60 (m, 1H), 7.55-7.51 (m, 1H), 6.65 (s, 1H), 4.22 (s, 3H). (ESI): m/z 405.1 [M+H]⁺.

Example 1/13: 1-Methyl-N-(2-(naphthalen-1-yl)-1H-pyrrolo[2,3-b]pyridin-6-yl)-1H-1,2,4-triazole-5-carboxamide (1/13)

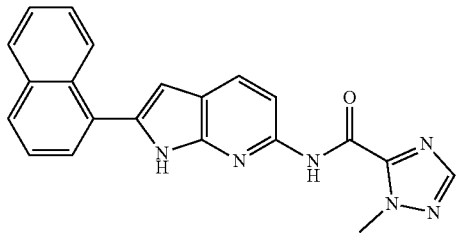 [SMILES: Cn1ncnc1C(=O)Nc1ccc2cc(-c3cccc4ccccc34)[nH]c2n1]

The title compound was prepared similar as described for Example 1 using in step 1 tert-butyl 6-chloro-2-(naphthalen-1-yl)-1H-pyrrolo[2,3-b]pyridine-1-carboxylate (Int 2/8) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide. ¹H NMR (400 MHz, DMSO-d₆): δ ppm 12.14 (s, 1H), 10.07 (s, 1H), 8.30-8.27 (m, 1H), 8.19 (s, 1H), 8.12 (d, J=8.4 Hz, 1H), 8.05-8.00 (m, 2H), 7.94-7.92 (m, 1H), 7.74-7.73 (m, 1H), 7.66-7.59 (m, 3H), 6.76 (s, 1H), 4.24 (s, 3H). (ESI): m/z 369.1 [M+H]⁺.

Example 1/14: N-(2-(4-Fluoro-2-(trifluoromethyl)phenyl)-1H-pyrrolo[2,3-b]pyridin-6-yl)-1-methyl-1H-1,2,4-triazole-5-carboxamide (1/14)

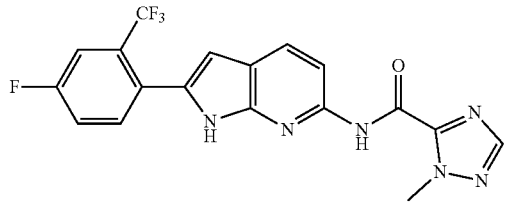 [SMILES: Cn1ncnc1C(=O)Nc1ccc2cc(-c3ccc(F)cc3C(F)(F)F)[nH]c2n1]

The title compound was prepared similar as described for Example 1 using in step 1 tert-butyl 6-chloro-2-(4-fluoro-2-(trifluoromethyl)phenyl)-1H-pyrrolo[2,3-b]pyridine-1-carboxylate (Int 2/9) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide. ¹H NMR (500 MHz, DMSO-d): 5 ppm 12.03 (s, 1H), 10.09 (s, 1H), 8.18 (s, 1H), 8.09 (d, J=8.5 Hz, 1H), 7.89 (d, J=8.5 Hz, 1H), 7.83-7.67 (m, 3H), 6.56 (s, 1H), 4.22 (s, 3H). (ESI): m/z 405.1 [M+H]⁺.

Example 1/15: N-(2-(2-(Difluoromethyl)phenyl)-1H-pyrrolo[2,3-b]pyridin-6-yl)-1-methyl-1H-1,2,4-triazole-5-carboxamide (1/15)

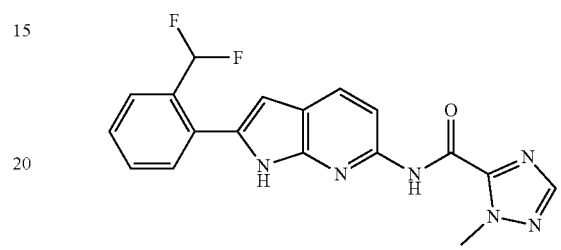

The title compound was prepared similar as described for Example 1 using in step 1 tert-butyl 6-chloro-2-(2-(difluoromethyl)phenyl)-1H-pyrrolo[2,3-b]pyridine-1-carboxylate (Int 2/10) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide. ¹H NMR (500 MHz, DMSO-d₆): δ ppm 12.11 (s, 1H), 10.08 (s, 1H), 8.18 (s, 1H), 8.12 (d, J=8.0 Hz, 1H), 7.91 (d, J=8.5 Hz, 1H), 7.81 (d, J=8.0 Hz, 1H), 7.73-7.67 (m, 2H), 7.62-7.59 (m, 1H), 7.15 (t, J=54.5 Hz, 1H), 6.60 (s, 1H), 4.22 (s, 3H). 369.2 (ESI): m/z [M+H]⁺.

Example 1/16: N-(2-(2,3-Dihydro-1H-inden-4-yl)-1H-pyrrolo[2,3-b]pyridin-6-yl)-1-methyl-1H-1,2,4-triazole-5-carboxamide (1/16)

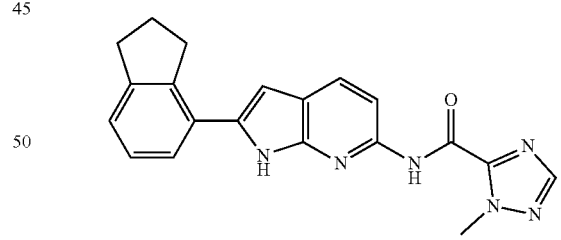

The title compound was prepared similar as described for Example 1 using in step 1 tert-butyl 6-chloro-2-(2,3-dihydro-1H-inden-4-yl)-1H-pyrrolo[2,3-b]pyridine-1-carboxylate (Int 2/11) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide. ¹H NMR (500 MHz, DMSO-d₆): δ ppm 11.92 (s, 1H), 10.01 (s, 1H), 8.18 (s, 1H), 8.05 (d, J=8.5 Hz, 1H), 7.87 (d, J=8.5 Hz, 1H), 7.61-7.59 (m, 1H), 7.28-7.25 (m, 2H), 6.69 (s, 1H), 4.23 (s, 3H), 3.15-3.12 (m, 2H), 2.96-2.93 (m, 2H), 2.10-2.04 (m, 2H). (ESI): m/z 359.2 [M+H]⁺.

Example 1/17: 1-Methyl-N-(2-(3-(trifluoromethyl) pyridin-2-yl)-1H-pyrrolo[2,3-b]pyridin-6-yl)-1H-1,2,4-triazole-5-carboxamide (1/17)

The title compound was prepared similar as described for Example 1 using in step 1 tert-butyl 6-chloro-2-(3-(trifluoromethyl)pyridin-2-yl)-1H-pyrrolo[2,3-b]pyridine-1-carboxylate (Int 2/12) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide. $^1$H NMR (500 MHz, DMSO-$d_6$): δ ppm 12.18 (s, 1H), 10.07 (s, 1H), 8.97 (s, J=2.8 Hz), 1H), 8.36-8.34 (m, 1H), 8.19-8.17 (m, 2H), 7.93 (d, J=8.0 Hz, 1H), 7.64 (dd, J$_1$=5.0 Hz, J$_2$=8.0 Hz, 1H), 6.93 (s, 1H), 4.23 (s, 3H). (ESI): m/z 388.1 [M+H]$^+$.

Example 1/18: N-(2-(2-Methoxyphenyl)-1H-pyrrolo[2,3-b]pyridin-6-yl)-1-methyl-11H-1,2,4-triazole-5-carboxamide (1/18)

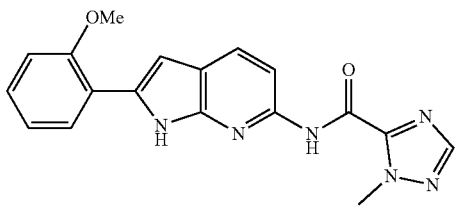 [SMILES: COc1ccccc1-c1cc2ccc(NC(=O)c3ncnn3C)nc2[nH]1]

The title compound was prepared similar as described for Example 1 using in step 1 tert-butyl 6-chloro-2-(2-methoxyphenyl)-1H-pyrrolo[2,3-b]pyridine-1-carboxylate (Int 2/13) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide. $^1$H NMR (500 MHz, DMSO-$d_6$): δ ppm 11.75 (s, 1H), 9.99 (s, 1H), 8.18 (s, 1H), 8.03 (d, J=8.5 Hz), 7.86-7.84 (m, 2H), 7.37-7.34 (m, 1H), 7.17 (d, J=8.5 Hz, 1H), 7.08-7.05 (m, 1H), 6.98 (s, 1H), 4.23 (s, 3H), 3.94 (s, 3H). (ESI): m/z 349.1 [M+H]$^+$.

Example 1/19: N-(2-(2-(Trifluoromethyl)phenyl)-1H-pyrrolo[2,3-b]pyridin-6-yl)furo[2,3-c]pyridine-5-carboxamide (1/19)

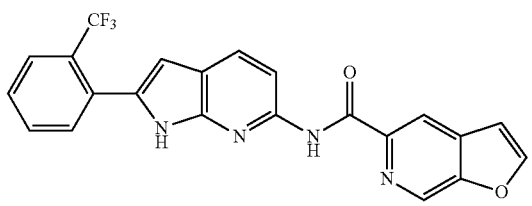 [SMILES: O=C(Nc1ccc2cc(-c3ccccc3C(F)(F)F)[nH]c2n1)c1cc2ccoc2cn1]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and furo[2,3-c]pyridine-5-carboxamide (Int 3/1) in place of 1-methyl-1H-pyrazole-5-carboxamide. $^1$H NMR (500 MHz, DMSO-$d_6$): δ ppm 11.93 (s, 1H), 10.51 (s, 1H), 9.13 (s, 1H), 8.62 (s, 1H), 8.43 (d, J=2.0 Hz, 1H), 8.16 (d, J=8.0 Hz, 1H), 8.10 (d, J=7.5 Hz, 1H), 7.91 (d, J=8.0 Hz, 1H), 7.82 (m, 1H), 7.73-7.66 (m, 1H), 7.30 (s, 1H), 6.57 (s, 1H). (ESI): m/z 423.1 [M+H]$^+$.

Example 1/20: 4-Methyl-N-(2-(2-(trifluoromethyl) phenyl)-1H-pyrrolo[2,3-b]pyridin-6-yl)-1,2,5-oxadiazole-3-carboxamide (1/20)

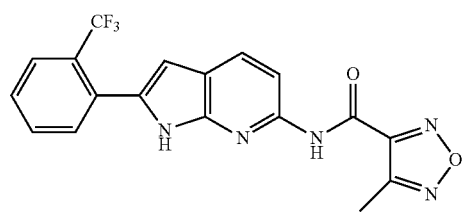 [SMILES: Cc1nonc1C(=O)Nc1ccc2cc(-c3ccccc3C(F)(F)F)[nH]c2n1]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and 4-methyl-1,2,5-oxadiazole-3-carboxamide (Int 3/2) in place of 1-methyl-1H-pyrazole-5-carboxamide. $^1$H NMR (500 MHz, DMSO-$d_6$): δ ppm 11.99 (s, 1H), 11.16 (s, 1H), 8.07 (d, J=8.0 Hz, 1H), 7.91 (d, J=8.0 Hz, 1H), 7.84-7.79 (m, 2H), 7.72-7.66 (m, 2H), 6.57 (s, 1H), 2.56 (s, 3H). (ESI): m/z 388.1 [M+H]$^+$.

Example 1/21: 4-Methyl-N-(2-(2-(trifluoromethyl) phenyl)-1H-pyrrolo[2,3-b]pyridin-6-yl)-4H-1,2,4-triazole-3-carboxamide (1/21)

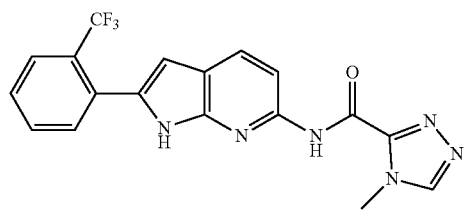 [SMILES: Cn1cnnc1C(=O)Nc1ccc2cc(-c3ccccc3C(F)(F)F)[nH]c2n1]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and 4-methyl-4H-1,2,4-triazole-3-carboxamide (Int 4) in place of 1-methyl-1H-pyrazole-5-carboxamide. $^1$H NMR (500 MHz, DMSO-$d_6$): δ ppm 12.03 (s, 1H), 10.18 (s, 1H), 8.77 (s, 1H), 8.08 (d, J=9.0 Hz, 1H), 7.91-7.86 (m, 2H), 7.81-7.78 (m, 1H), 7.72-7.66 (m, 1H), 6.57 (s, 1H), 3.97 (s, 3H). (ESI): m/z 387.1 [M+H]$^+$.

Example 1/22: N-(2-(2-(trifluoromethyl)phenyl)-1H-pyrrolo[2,3-b]pyridin-6-yl)imidazo[1,5-a]pyridine-3-carboxamide (1/22)

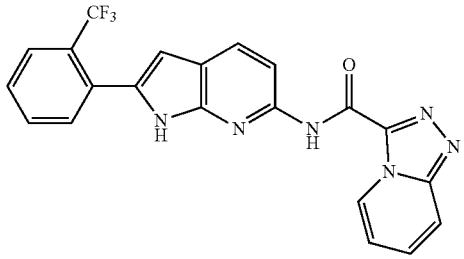 [SMILES: O=C(Nc1ccc2cc(-c3ccccc3C(F)(F)F)[nH]c2n1)c1nnc2ccccn12]

The title compound was prepared similar as described for Example 1 using in step 1 tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and imidazo[1,5-a]pyridine-3-carboxamide in place of 1-methyl-11H-pyrazole-5-carboxamide. $^1$H NMR (500 MHz, DMSO-d): δ ppm 11.97 (s, 1H), 9.80 (s, 1H), 9.46-9.44 (m, 1H), 8.09 (m, 2H), 8.10-8.05 (m, 2H), 7.91-7.89 (m, 2H), 7.82-7.66 (m, 4H), 7.22-7.20 (m, 1H), 7.15-7.21 (m, 1H), 6.57 (s, 1H). (ESI): m/z 422.2 [M+H]$^+$.

Example 1/23: 1-Methyl-N-(2-(2-(methylsulfonyl)phenyl)-1H-pyrrolo[2,3-b]pyridin-6-yl)-1H-1,2,4-triazole-5-carboxamide (1/23)

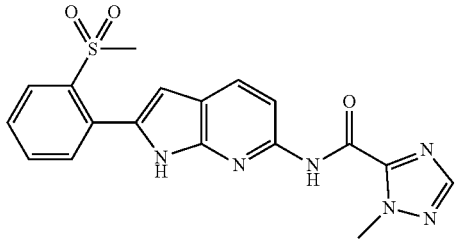 [SMILES: Cn1ncnc1C(=O)Nc1ccc2cc(-c3ccccc3S(C)(=O)=O)[nH]c2n1]

The title compound was prepared similar as described for Example 1 using in step 1 tert-butyl 6-chloro-2-(2-(methylsulfonyl)phenyl)-1H-pyrrolo[2,3-b]pyridine-1-carboxylate (Int 2/14) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 11.98 (s, 1H), 10.11 (s, 1H), 8.18 (s, 1H), 8.16-8.11 (m, 2H), 7.91 (d, J=8.5 Hz, 1H), 7.85-7.82 (m, 1H), 7.76-7.70 (m, 2H), 6.82 (s, 1H), 4.22 (s, 3H), 3.00 (s, 3H). (ESI): m/z 397.0 [M+H]$^+$.

Example 1/24: N-(2-(3-(Difluoromethyl)phenyl)-1H-pyrrolo[2,3-b]pyridin-6-yl)-1-methyl-1H-1,2,4-triazole-5-carboxamide (1/24)

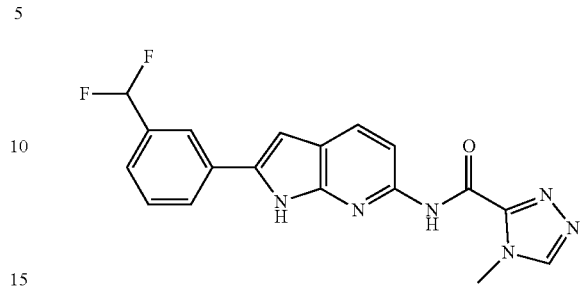

The title compound was prepared similar as described for Example 1 using in step 1 tert-butyl 6-chloro-2-(3-(difluoromethyl)phenyl)-1H-pyrrolo[2,3-b]pyridine-1-carboxylate (Int 2/15) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.26 (s, 1H), 10.07 (s, 1H), 8.19-8.06 (m, 4H), 7.89-7.87 (m, 1H), 7.63-7.53 (m, 2H), 7.20-6.98 (m, 2H), 4.22 (s, 3H). (ESI): m/z 369.1 [M+H]$^+$.

Example 1/25: N-(2-(4-(Difluoromethyl)phenyl)-1H-pyrrolo[2,3-b]pyridin-6-yl)-1-methyl-1H-1,2,4-triazole-5-carboxamide (1/25)

The title compound was prepared similar as described for Example 1 using in step 1 tert-butyl 6-chloro-2-(4-(difluoromethyl)phenyl)-1H-pyrrolo[2,3-b]pyridine-1-carboxylate (Int 2/16) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d): δ ppm 12.25 (s, 1H), 10.07 (s, 1H), 8.19 (s, 1H), 8.08-8.06 (m, 3H), 7.89-7.88 (m, 1H), 7.67-7.65 (m, 2H), 7.19-6.99 (m, 2H), 4.23 (s, 3H). (ESI): m/z 369.1 [M+H]$^+$.

Example 1/26: N-(2-(5-Chloro-2-(trifluoromethyl)phenyl)-1H-pyrrolo[2,3-b]pyridin-6-yl)-1-methyl-11H-1,2,4-triazole-5-carboxamide (1/26)

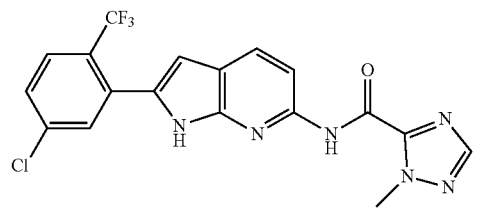 [SMILES: Cn1ncnc1C(=O)Nc1ccc2cc(-c3cc(Cl)ccc3C(F)(F)F)[nH]c2n1]

The title compound was prepared similar as described for Example 1 using in step 1 tert-butyl 6-chloro-2-(5-chloro-2-(trifluoromethyl)phenyl)-1H-pyrrolo[2,3-b]pyridine-1-carboxylate (Int 2/17) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.10 (s, 1H), 10.13 (s, 1H), 8.19 (s, 1H), 8.12 (d, J=8.0 Hz, 1H), 7.94-7.91 (m, 2H), 7.82-7.74 (m, 2H), 6.65 (s, 1H), 4.22 (s, 3H). (ESI): m/z 421.1 [M+H]$^+$.

Example 1/27: N-(2-(5-Cyclopropyl-2-(trifluoromethyl)phenyl)-1H-pyrrolo[2,3-b]pyridin-6-yl)-1-methyl-1H-1,2,4-triazole-5-carboxamide (1/27)

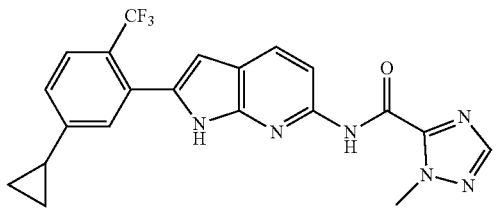 [SMILES: Cn1ncnc1C(=O)Nc1ccc2cc(-c3cc(C4CC4)ccc3C(F)(F)F)[nH]c2n1]

The title compound was prepared similar as described for Example 1 using in step 1 tert-butyl 6-chloro-2-(5-cyclopropyl-2-(trifluoromethyl)phenyl)-1H-pyrrolo[2,3-b]pyridine-1-carboxylate (Int 23) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (400 MHz, DMSO-d): δ ppm 11.99 (s, 1H), 10.08 (s, 1H), 8.18 (s, 1H), 8.09 (d, J=8.5 Hz, 1H), 7.89 (d, J=8.5 Hz, 1H), 7.74 (d, J=8.8 Hz, 1H), 7.35 (d, J=6.0 Hz, 2H), 6.57 (s, 1H), 4.22 (s, 3H), 2.10-2.02 (m, 1H), 1.10-1.04 (m, 2H), 0.89-0.84 (m, 2H). (ESI): m/z 427.1 [M+H]$^+$.

Example 1/28: N-(2-(2-(Difluoromethyl)-4,5-difluorophenyl)-1H-pyrrolo[2,3-b]pyridin-6-yl)-1-methyl-1H-1,2,4-triazole-5-carboxamide (1/28)

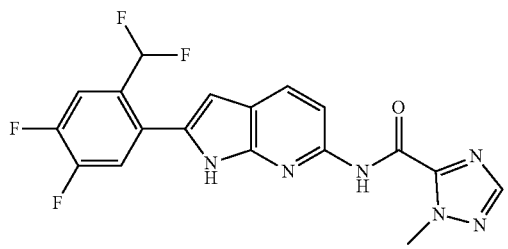 [SMILES: Cn1ncnc1C(=O)Nc1ccc2cc(-c3cc(F)c(F)cc3C(F)F)[nH]c2n1]

The title compound was prepared similar as described for Example 1 using in step 1 tert-butyl 6-chloro-2-(2-(difluoromethyl)-4,5-difluorophenyl)-1H-pyrrolo[2,3-b]pyridine-1-carboxylate (Int 24) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (400 MHz, DMSO-d): δ ppm 12.16 (s, 1H), 10.13 (s, 1H), 8.19 (s, 1H), 8.14 (d, J=8.8 Hz, 1H), 7.93-7.91 (m, 1H), 7.88-7.81 (m, 2H), 7.17 (t, J=54 Hz, 1H), 6.65 (s, 1H), 4.22 (s, 3H). (ESI): m/z 405.1 [M+H]$^+$.

Example 1/29: N-(2-(5-Ethyl-2-(trifluoromethyl)phenyl)-1H-pyrrolo[2,3-b]pyridin-6-yl)-1-methyl-1H-1,2,4-triazole-5-carboxamide (1/29)

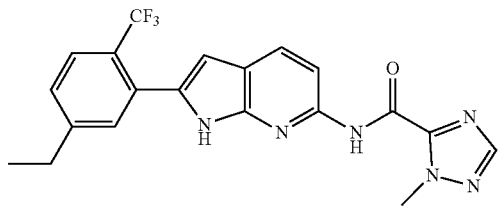 [SMILES: CCc1ccc(C(F)(F)F)c(-c2cc3ccc(NC(=O)c4ncnn4C)nc3[nH]2)c1]

The title compound was prepared similar as described for Example 1 using in step 1 tert-butyl 6-chloro-2-(5-ethyl-2-(trifluoromethyl)phenyl)-1H-pyrrolo[2,3-b]pyridine-1-carboxylate (Int 23/1) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (400 MHz, DMSO-d$_6$): δ ppm 12.00 (s, 1H), 10.09 (s, 1H), 8.18 (s, 1H), 8.09 (d, J=8.4 Hz, 1H), 7.90 (d, J=8.4 Hz, 1H), 7.80 (d, J=8.1 Hz, 1H), 7.62-7.47 (m, 2H), 6.57 (s, 1H), 4.23 (s, 3H), 2.75 (q, J=7.5 Hz, 2H), 1.26 (t, J=7.6 Hz, 3H). (ESI): m/z 415.1 [M+H]$^+$.

Example 1/30: N-(2-(2,5-Bis(trifluoromethyl)phenyl)-1H-pyrrolo[2,3-b]pyridin-6-yl)-1-methyl-1H-1,2,4-triazole-5-carboxamide (1/30)

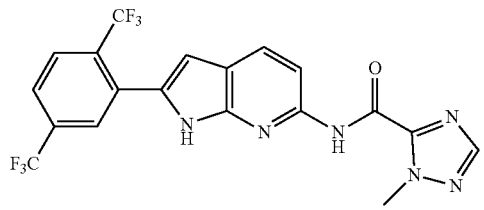 [SMILES: Cn1ncnc1C(=O)Nc1ccc2cc(-c3cc(C(F)(F)F)ccc3C(F)(F)F)[nH]c2n1]

The title compound was prepared similar as described for Example 1 using in step 1 tert-butyl 2-(2,5-bis(trifluoromethyl)phenyl)-6-chloro-1H-pyrrolo[2,3-b]pyridine-1-carboxylate (Int 2/18) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.15 (s, 1H), 10.11 (s, 1H), 8.18 (s, 1H), 8.17-8.12 (m, 2H), 8.08-8.04 (m, 2H), 7.93-7.91 (m, 1H), 6.69 (s, 1H), 4.22 (s, 3H). (ESI): m/z 455.0 [M+H]$^+$.

Example 1/31: 1-Methyl-N-(5-methyl-2-(2-(trifluoromethyl)phenyl)-1H-pyrrolo[2,3-b]pyridin-6-yl)-1H-1,2,4-triazole-5-carboxamide (31)

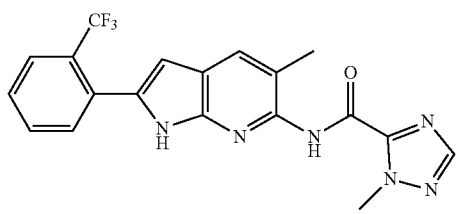 [SMILES: Cc1cc2cc(-c3ccccc3C(F)(F)F)[nH]c2nc1NC(=O)c1ncnn1C]

The title compound was prepared similar as described for Example 1 using in step 1 tert-butyl 6-chloro-5-methyl-2-(2-(trifluoromethyl)phenyl)-1H-pyrrolo[2,3-b]pyridine-1-carboxylate (Int 25) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 11.96 (s, 1H), 10.71 (s, 1H), 8.17 (s, 1H), 7.91-7.90 (m, 2H), 7.82-7.79 (m, 1H), 7.70-7.69 (m, 2H), 6.52 (s, 1H), 4.18 (s, 3H), 2.35 (s, 3H). (ESI): m/z 401.1 [M+H]$^+$.

Example 1/32: N-(2-(2-(Difluoromethyl)furan-3-yl)-1H-pyrrolo[2,3-b]pyridin-6-yl)-1-methyl-1H-1,2,4-triazole-5-carboxamide (1/32)

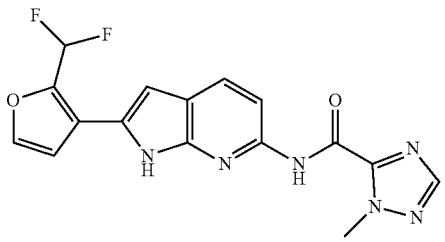 [SMILES: Cn1ncnc1C(=O)Nc1ccc2cc(-c3ccoc3C(F)F)[nH]c2n1]

The title compound was prepared similar as described for Example 1 using in step 1 tert-butyl 6-chloro-2-(2-(difluoromethyl)furan-3-yl)-1H-pyrrolo[2,3-b]pyridine-1-carboxylate (Int 8) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.10 (s, 1H), 10.08 (s, 1H), 8.18 (s, 1H), 8.08-7.88 (m, 3H), 7.37 (t, J=52.0 Hz, 1H), 7.14 (s, 1H), 6.73 (s, 1H), 4.22 (s, 3H). (ESI): m/z 359.1 [M+H]$^+$.

Example 1/33: 1-Methyl-N-(2-(5-methyl-2-(trifluoromethyl)phenyl)-1H-pyrrolo[2,3-b]pyridin-6-yl)-1H-1,2,4-triazole-5-carboxamide (1/33)

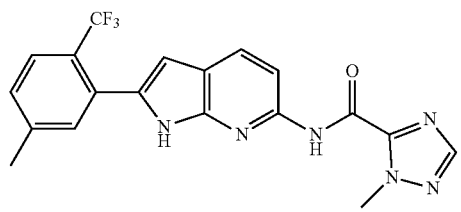 [SMILES: Cc1ccc(C(F)(F)F)c(-c2cc3ccc(NC(=O)c4ncnn4C)nc3[nH]2)c1]

The title compound was prepared similar as described for Example 1 using in step 1 tert-Butyl 6-chloro-2-(5-methyl-2-(trifluoromethyl)phenyl)-1H-pyrrolo[2,3-b]pyridine-1-carboxylate (Int 2/19) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 11.99 (s, 1H), 10.07 (s, 1H), 8.18 (s, 1H), 8.08 (d, J=8.5 Hz), 7.89 (d, J=8.5 Hz, 1H), 7.77 (d, J=8.0 Hz, 1H), 7.54 (s, 1H), 7.47 (d, J=8.0 Hz, 1H), 6.56 (s, 1H), 4.22 (s, 3H), 2.45 (s, 3H). (ESI): m/z 401.0 [M+H]$^+$.

Example 1/34: N-(2-(5-Chloro-2-(difluoromethyl)phenyl)-1H-pyrrolo[2,3-b]pyridin-6-yl)-1-methyl-1H-1,2,4-triazole-5-carboxamide (1/34)

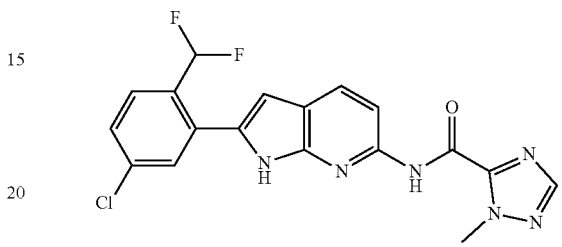

The title compound was prepared similar as described for Example 1 using in step 1 tert-butyl 6-chloro-2-(5-chloro-2-(difluoromethyl)phenyl)-1H-pyrrolo[2,3-b]pyridine-1-carboxylate (Int 2/20) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d): δ ppm 12.18 (s, 1H), 10.13 (s, 1H), 8.19 (s, 1H), 8.14 (d, J=8.5 Hz, 1H), 7.93 (d, J=8.5 Hz, 1H), 7.84-7.81 (m, 2H), 7.67-7.65 (m, 1H), 7.17 (t, J=54.5 Hz, 1H), 6.67 (s, 1H), 4.22 (s, 3H). (ESI): m/z 403.1 [M+H]$^+$.

Example 1/35: N-(2-(2-(Difluoromethyl)-5-methylphenyl)-1H-pyrrolo[2,3-b]pyridin-6-yl)-1-methyl-1H-1,2,4-triazole-5-carboxamide (1/35)

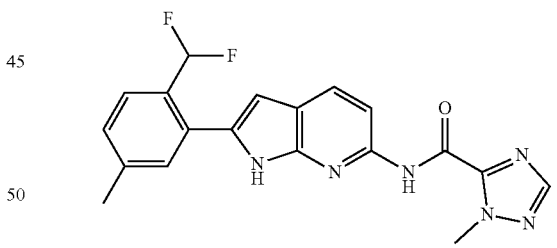

The title compound was prepared similar as described for Example 1 using in step 1 tert-Butyl 6-chloro-2-(2-(difluoromethyl)-5-methylphenyl)-1H-pyrrolo[2,3-b]pyridine-1-carboxylate (Int 2/21) in place of tert-butyl 6-chloro-2-(o-tolyl)-1H-pyrrolo[2,3-b]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.07 (s, 1H), 10.09 (s, 1H), 8.19 (s, 1H), 8.11 (d, J=8.5 Hz, 1H), 7.91 (d, J=8.5 Hz, 1H), 7.69 (d, J=9.0 Hz, 1H), 7.55 (s, 1H), 7.41 (d, J=7.5 Hz, 1H), 7.11 (t, J=55.0 Hz, 1H), 6.57 (s, 1H), 4.22 (s, 3H), 2.43 (s, 3H). (ESI): m/z 383.1 [M+H]$^+$.

Example 2: 1-Methyl-n⁵-(2-(2-(trifluoromethyl)phenyl)-1H-pyrrolo[2,3-b]pyridin-6-yl)-1H-pyrazole-3,5-dicarboxamide (2)

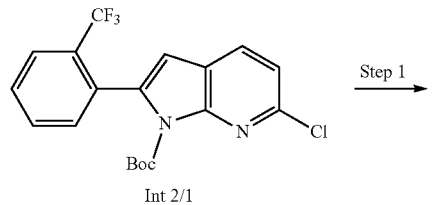

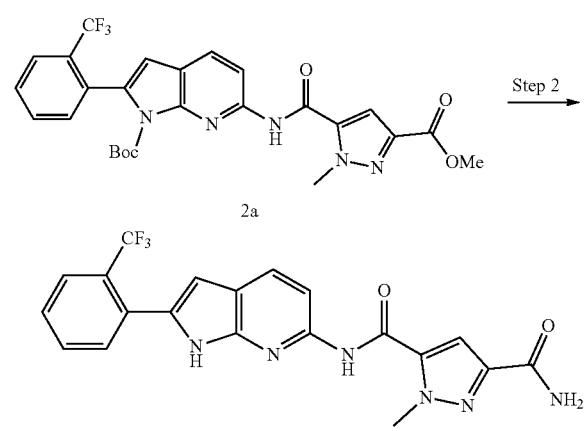

Step 1: tert-Butyl 6-(3-(methoxycarbonyl)-1-methyl-1H-pyrazole-5-carboxamido)-2-(2-(trifluoromethyl)phenyl)-1H-pyrrolo[2,3-b]pyridine-1-carboxylate (2a)

The title compound was prepared similar as described for Example 1, step 1 (1a) using tert-butyl 6-chloro-2-(2-(trifluoromethyl)phenyl)-1H-pyrrolo[2,3-b]pyridine-1-carboxylate (Int 2/1) in place of tert-butyl 6-chloro-2-(o-tolyl)-1H-pyrrolo[2,3-b]pyridine-1-carboxylate (Int 2) and methyl 5-carbamoyl-1-methyl-1H-pyrazole-3-carboxylate (Int 3/3) in place of 1-methyl-1H-pyrazole-5-carboxamide.

Step 2: 1-Methyl-5-((2-(2-(trifluoromethyl)phenyl)-1H-pyrrolo[2,3-b]pyridin-6-yl)carbamoyl)-1H-pyrazole-3-carboxylic acid (2)

A mixture of tert-butyl 6-(3-(methoxycarbonyl)-1-methyl-1H-pyrazole-5-carboxamido)-2-(2-(trifluoromethyl)phenyl)-1H-pyrrolo[2,3-b]pyridine-1-carboxylate (2a) (160 mg, 0.29 mmol) in NH$_3$/MeOH (7M, 15 mL) was stirred at 50° C. overnight. The mixture was concentrated to dryness and the residue was purified by prep-HPLC to give the title compound as a white solid. $^1$H NMR (500 MHz, DMSO-d$_6$): δ ppm 11.88 (s, 1H), 10.80 (s, 1H), 8.04 (d, J=8.5 Hz, 1H), 7.91 (d, J=8.0 Hz, 1H), 7.84-7.79 (m, 2H), 7.72-7.66 (m, 2H), 7.62 (s, 1H), 7.57 (s, 1H), 7.35 (s, 1H), 6.55 (s, 1H), 4.17 (s, 3H). (ESI): m/z 429.1 [M+H]$^+$.

Example 3: 1-Methyl-N-(1-methyl-2-(2-(trifluoromethyl)phenyl)-1H-pyrrolo[2,3-b]pyridin-6-yl)-1H-1,2,4-triazole-5-carboxamide (3)

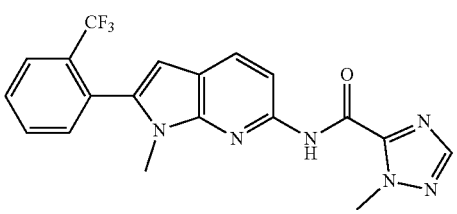 [SMILES: Cn1ncnc1C(=O)Nc1ccc2cc(-c3ccccc3C(F)(F)F)n(C)c2n1]

The title compound was prepared similar as described for Example 1 using in step 1 6-chloro-1-methyl-2-(2-(trifluoromethyl)phenyl)-1H-pyrrolo[2,3-b]pyridine (Int 5) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 10.13 (s, 1H), 8.19 (s, 1H), 8.11 (d, J=8.5 Hz, 1H), 7.96-7.94 (m, 2H), 7.84-7.82 (m, 1H), 7.79-7.77 (m, 1H), 7.67 (d, J=7.5 Hz, 1H), 6.55 (s, 1H), 4.23 (s, 3H), 3.49 (s, 3H). (ESI): m/z 401.1 [M+H]$^+$.

Example 4: N-(2-(2-Cyclopropylphenyl)-1H-pyrrolo[2,3-b]pyridin-6-yl)-1-methyl-1H-1,2,4-triazole-5-carboxamide (4)

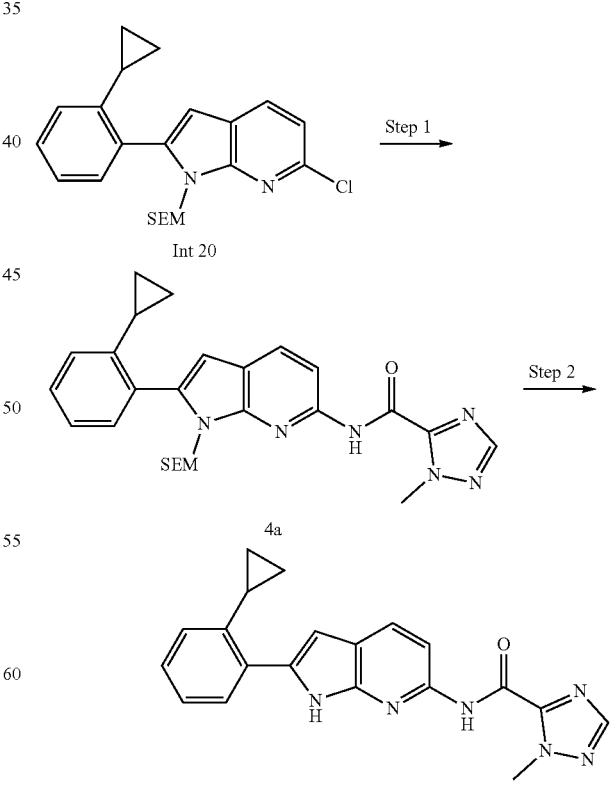

Step 1: N-(2-(2-Cyclopropylphenyl)-1-((2-(trimethylsilyl)ethoxy)methyl)-1H-pyrrolo[2,3-b]pyridin-6-yl)-1-methyl-1H-1,2,4-triazole-5-carboxamide (4a)

A mixture of 6-chloro-2-(2-cyclopropylphenyl)-1-((2-(trimethylsilyl)ethoxy)methyl)-1H-pyrrolo[2,3-b]pyridine (Int 20) (180 g, 0.45 mmol), 1-methyl-1H-1,2,4-triazole-5-carboxamide (Int 3) (127 mg, 1.00 mmol), K$_2$CO$_3$ (138 mg, 1.00 mmol), tBuXPhos (200 mg) and Pd$_2$(dba)$_3$ (200 mg) in DMF (4 mL) was stirred at 135° C. overnight. The mixture was diluted with water (30 mL) and extracted with EtOAc (3×50 mL). The combined organic layers were dried over Na$_2$SO$_4$, filtered and concentrated to dryness. The residue was purified by column chromatography on silica gel (PE/EtOAc=15:1) to give the title compound as a yellow oil.

Step 2: N-(2-(2-Cyclopropylphenyl)-1H-pyrrolo[2,3-b]pyridin-6-yl)-1-methyl-1H-1,2,4-triazole-5-carboxamide (4)

To a mixture of N-(2-(2-cyclopropylphenyl)-1-((2-(trimethylsilyl)ethoxy)methyl)-1H-pyrrolo[2,3-b]pyridin-6-yl)-1-methyl-1H-1,2,4-triazole-5-carboxamide (4a) (120 mg, 0.245 mmol) in DCM (5 mL) was added BF$_3$.Et$_2$O (2 mL) and the mixture was stirred at rt for 1 h. The mixture was diluted water (2 mL) and concentrated. The residue was dissolved in MeOH (5 mL) and the pH was adjusted to pH=11 with 10% aqueous KOH. The mixture was stirred at room temperature for 2 h and extracted with EtOAc (2×100 mL). The combined organic layers were dried over anhydrous Na$_2$SO$_4$ and concentrated to dryness. The residue was purified by column chromatography on silica gel (DCM/MeOH=50:1) to give the title compound as a white solid. $^1$H NMR (DMSO-d$_6$, 400 MHz): δ ppm 11.92 (s, 1H), 10.04 (s, 1H), 8.18 (s, 1H), 8.05 (d, J=8.4 Hz, 1H), 7.87 (d, J=8.4 Hz, 1H), 7.52 (d, J=7.6 Hz, 1H), 7.34-7.26 (m, 2H), 7.08 (d, J=6.8 Hz, 1H), 6.70 (s, 1H), 4.22 (s, 3H), 2.26-2.19 (m, 1H), 0.94-0.92 (m, 2H), 0.72-0.71 (m, 2H). (ESI): m/z 359.0 [M+H]$^+$.

Examples 4/1 to 4/9

The following Examples were prepared similar as described for Example 4 using the appropriate carboxamide building blocks and intermediates.

| # | Int. # | Structure | Analytical data |
|---|---|---|---|
| 4/1 | Int 20/1, Int 3 | 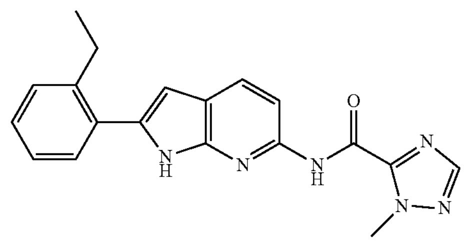 [SMILES: CCc1ccccc1-c1cc2ccc(NC(=O)c3ncnn3C)nc2[nH]1] | $^1$H NMR (400 MHz, CD$_3$OD): δ ppm 8.01 (m, 3H), 7.46-7.44 (m, 1H), 7.36-7.26 (m, 3H), 6.48 (s, 1H), 4.31 (s, 3H), 2.85 (q, J = 7.2 Hz, 2H), 1.16 (t, J = 7.2 Hz, 3H). (ESI): m/z 349.0 [M + H]$^+$. |
| 4/2 | Int 20/2, Int 3 | 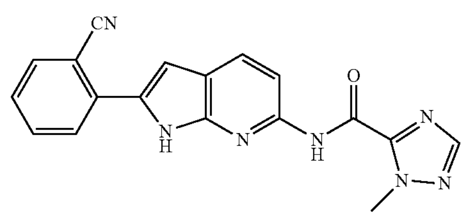 [SMILES: Cn1ncnc1C(=O)Nc1ccc2cc(-c3ccccc3C#N)[nH]c2n1] | $^1$H NMR (400 MHz, DMSO-d$_6$): δ ppm 12.28 (s, 1H), 10.16 (s, 1H), 8.18 (d, J = 11.2 Hz, 2H), 7.99-7.91 (m, 3H), 7.85-7.81 (m, 1H), 7.59-7.55 (m, 1H), 7.13 (s, 1H), 4.23 (s, 3H). (ESI): m/z 344.0 [M + H]$^+$. |
| 4/3 | Int 20/3, Int 3 | 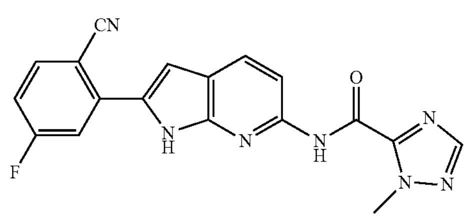 [SMILES: Cn1ncnc1C(=O)Nc1ccc2cc(-c3cc(F)ccc3C#N)[nH]c2n1] | $^1$H NMR (400 MHz, DMSO-d$_6$): δ ppm 12.33 (s, 1H), 10.19 (s, 1H), 8.21-8.19 (m, 2H), 8.11-8.07 (m, 1H), 7.94-7.92 (m, 1H), 7.86-7.83 (m, 1H), 7.47-7.43 (m, 1H), 7.25 (s, 1H), 4.22 (s, 3H). (ESI): m/z 362.1 [M + H]$^+$. |
| 4/4 | Int 20/4, | 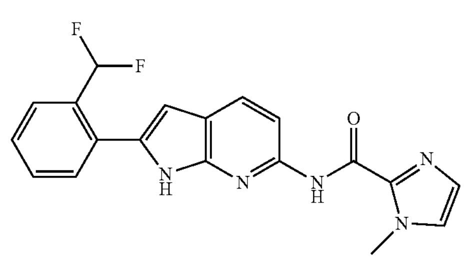 [SMILES: Cn1ccnc1C(=O)Nc1ccc2cc(-c3ccccc3C(F)F)[nH]c2n1] | $^1$H NMR (DMSO-d$_6$, 400 MHz): δ ppm 12.06 (s, 1H), 9.78 (s, 1H), 8.09 (d, J = 8.4 Hz, 1H), 7.99 (d, J = 8.4 Hz, 1H), 7.81 (d, J = 7.6 Hz, 1H), 7.73-7.67 (m, 2H), 7.61-7.58 (m, 1H), 7.52 (s, 1H), 7.15 (t, J = 54.4 Hz, 1H), 7.13 (s, 1H), 6.57 (m, 1H), 4.05 (s, 3H). (ESI): m/z 368.0 [M + H]$^+$. |

| # | Int. # | Structure | Analytical data |
|---|---|---|---|
| 4/5 | Int 21, Int 3 | 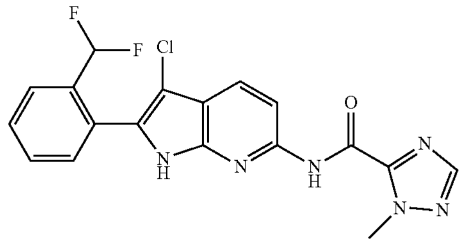 | $^1$H NMR (CDCl$_3$, 400 MHz): δ ppm 9.72 (s, 1H), 8.66 (s, 1H), 8.23 (d, J = 8.8 Hz, 1H), 8.05 (d, J = 8.4 Hz, 1H), 7.93 (s, 1H), 7.85-7.83 (m, 1H), 7.66-7.61 (m, 3H), 6.69 (t, J = 54.6 Hz, 1H), 4.36 (s, 3H). (ESI): m/z 402.9 [M + H]$^+$. |
| 4/6 | Int 22, Int 3 | 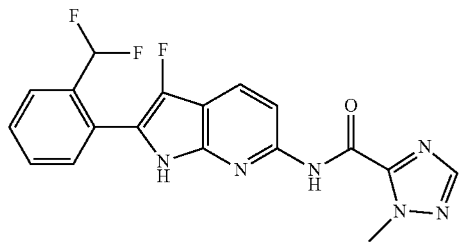 [SMILES: Cn1ncnc1C(=O)Nc1ccc2c(F)c(-c3ccccc3C(F)F)[nH]c2n1] | $^1$H NMR (CDCl$_3$, 300 MHz): δ ppm 9.72 (s, 1H), 8.95 (s, 1H), 8.21 (d, J = 7.5 Hz, 1H), 8.08 (d, J = 8.7 Hz, 1H), 7.91 (s, 1H), 7.83 (d, J = 8.7 Hz, 1H), 7.66-7.52 (m, 3H), 6.83 (t, J = 54.6 Hz, 1H), 4.37 (s, 3H). (ESI): m/z 386.8 [M + H]$^+$. |
| 4/7 | Int 20/4, Int 7 | 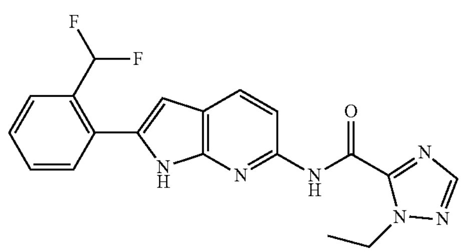 [SMILES: CCn1ncnc1C(=O)Nc1ccc2cc(-c3ccccc3C(F)F)[nH]c2n1] | $^1$H NMR (DMSO-d$_6$, 400 MHz): δ ppm 12.13 (s, 1H), 10.13 (s, 1H), 8.21 (s, 1H), 8.12 (d, J = 8.4 Hz, 1H), 7.92 (d, J = 8.8 Hz, 1H), 7.82 (d, J = 7.2 Hz, 1H), 7.73-7.67 (m, 2H), 7.62-7.58 (m, 1H), 7.16 (t, J = 54.4 Hz, 1H), 6.60 (d, J = 2.0 Hz, 1H), 4.67 (q, J = 6.8 Hz, 2H), 1.44 (t, J = 6.8 Hz, 3H). (ESI): m/z 383.0 [M + H]$^+$. |
| 4/8 | Int 20/7, Int 3 | 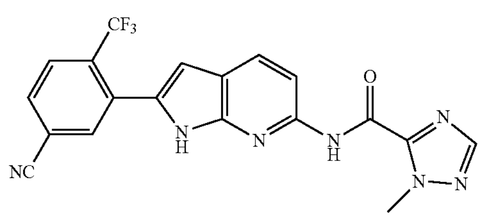 [SMILES: Cn1ncnc1C(=O)Nc1ccc2cc(-c3cc(C#N)ccc3C(F)(F)F)[nH]c2n1] | $^1$H NMR (DMSO-d$_6$, 400 MHz): δ ppm 12.11 (s, 1H), 10.15 (s, 1H), 8.25 (s, 1H), 8.18 (s, 1H), 8.14-8.11 (m, 3H), 7.92 (d, J = 8.4 Hz, 1H), 6.68 (s, 1H), 4.22 (s, 3H). (ESI): m/z 412.1 [M + H]$^+$. |
| 4/9 | Int 20/8, Int 3 | 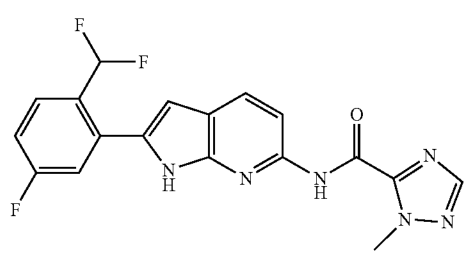 [SMILES: Cn1ncnc1C(=O)Nc1ccc2cc(-c3cc(F)ccc3C(F)F)[nH]c2n1] | $^1$H NMR (DMSO-d$_6$, 400 MHz): δ ppm 12.17 (s, 1H), 10.13 (s, 1H), 8.18-8.13 (m, 2H), 7.93-7.87 (m, 2H), 7.59-7.57 (m, 1H), 7.47-7.42 (m, 1H), 7.15 (t, J = 54.4 Hz, 1H), 6.67 (m, 1H), 4.22 (s, 3H). (ESI): m/z 386.8 [M + H]$^+$. |

Example 5: N-(2-(2-(Difluoromethyl)phenyl)-1H-pyrrolo[2,3-b]pyridin-6-yl)-1-methyl-1H-imidazole-5-carboxamide (5)

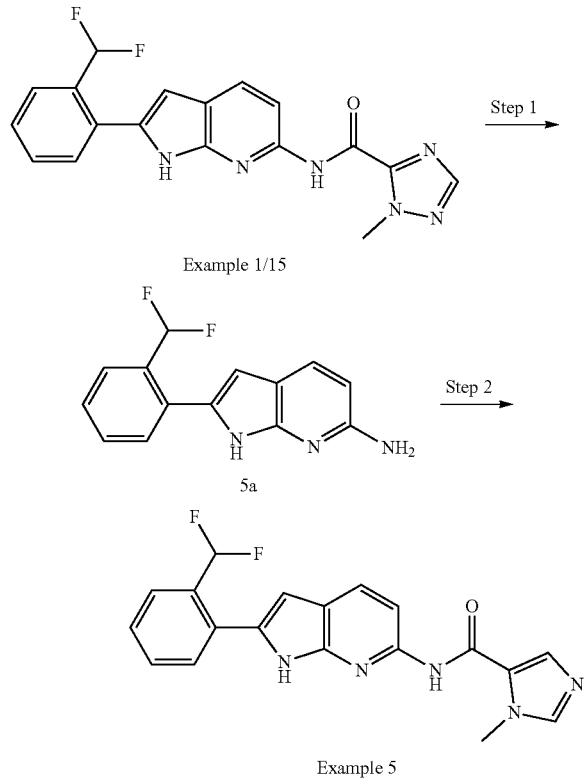

Step 1: 2-(2-(Difluoromethyl)phenyl)-1H-pyrrolo[2,3-b]pyridin-6-amine (5a)

To a mixture of N-(2-(2-(difluoromethyl)phenyl)-1H-pyrrolo[2,3-b]pyridin-6-yl)-1-methyl-1H-1,2,4-triazole-5-carboxamide (Example 1/15) (0.20 g, 0.534 mmol) in MeOH (5 mL) and water (2 mL) was added NaOH (0.217 g, 5.43 mmol) and the mixture was stirred at reflux for 2 h. The mixture was cooled to rt, diluted with water (50 mL) and extracted with EtOAc (2×100 mL). The combined organic layers were dried over anhydrous $Na_2SO_4$, filtered and concentrated to dryness to give the title compound.

Step 2: N-(2-(2-(Difluoromethyl)phenyl)-1H-pyrrolo[2,3-b]pyridin-6-yl)-1-methyl-1H-imidazole-5-carboxamide (5)

To a mixture of 2-(2-(difluoromethyl)phenyl)-1H-pyrrolo[2,3-b]pyridin-6-amine (5a) (0.14 g, 0.54 mmol) and 3-methyl-3H-imidazole-4-carboxylic acid (0.102 g, 0.81 mmol) in DMF (3 mL) was added HATU (0.41 g, 1.08 mmol) and DIPEA (0.140 g, 1.08 mmol). The mixture was stirred at rt for 5 h. The mixture was diluted with water (50 mL) and extracted with EtOAc (3×50 mL). The combined organic layers were dried over $Na_2SO_4$, filtered and concentrated to dryness. The residue was purified by column chromatography on silica gel (DCM/MeOH=10:1) to give the title compound as a white solid. $^1$H NMR (DMSO-$d_6$, 400 MHz): δ ppm 11.87 (s, 1H), 10.50 (s, 1H), 8.04-8.00 (m, 2H), 7.85-7.80 (m, 3H), 7.71-7.69 (m, 2H), 7.62-7.58 (m, 1H), 7.15 (t, J=54.4 Hz, 1H), 6.56 (s, 1H), 3.88 (s, 3H). (ESI): m/z 368.0 [M+H]$^+$.

Examples 5/1 to 5/2

The following Examples were prepared similar as described for Example 5 using the appropriate carboxylic acid building blocks.

| # | Building blocks | Structure | Analytical data |
|---|---|---|---|
| 5/1 | HOOC-(oxazole-methyl) | (structure) | $^1$H NMR (DMSO-$d_6$, 400 MHz): δ ppm 12.05 (s, 1H), 9.40 (s, 1H), 8.50 (s, 1H), 8.09 (d, J = 8.8 Hz, 1H), 8.01 (d, J = 8.4 Hz, 1H), 7.81 (d, J = 7.6 Hz, 1H), 7.72-7.67 (m, 2H), 7.61-7.58 (m, 1H), 7.15 (t, J = 54.4 Hz, 1H), 6.58 (s, 1H), 2.68 (s, 3H). (ESI): m/z 369.0 [M + H]$^+$. |
| 5/2 | HOOC-(thiazole-methyl) | (structure) | $^1$H NMR (DMSO-$d_6$, 400 MHz) δ ppm 12.02 (s, 1H), 9.90 (s, 1H), 9.04 (s, 1H), 8.10-8.05 (m, 2H), 7.81 (d, J = 8.0 Hz, 1H), 7.70-7.69 (m, 2H), 7.61-7.59 (m, 1H), 7.15 (t, J = 54.4 Hz, 1H), 6.57 (s, 1H), 2.86 (s, 3H). (ESI): m/z 384.9 [M + H]$^+$. |

Example 6: 2-(6-(1-Methyl-1H-1,2,4-triazole-5-carboxamido)-1H-pyrrolo[2,3-b]pyridin-2-yl)benzoic acid (6)

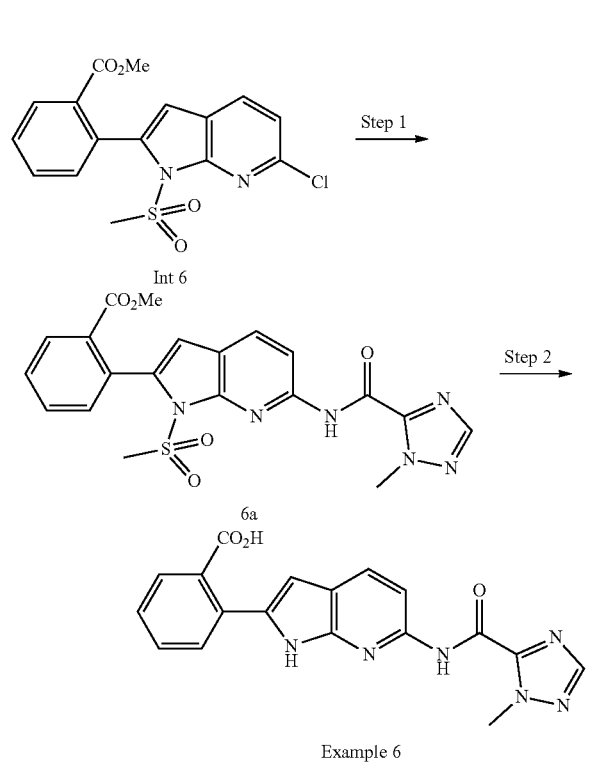

Step 1: Methyl 2-(6-(1-methyl-1H-1,2,4-triazole-5-carboxamido)-1-(methylsulfonyl)-1H-pyrrolo[2,3-b]pyridin-2-yl)benzoate (6a)

The title compound was prepared similar as described for Example 1, step 1 (1a) using methyl 2-(6-chloro-1-(methylsulfonyl)-1H-pyrrolo[2,3-b]pyridin-2-yl)benzoate (Int 6) in place of tert-butyl 6-chloro-2-(o-tolyl)-1H-pyrrolo[2,3-b]pyridine-1-carboxylate (Int 1) and 1-methyl-1H-1,2,4-triazole-5-carboxamide (Int 3) in place of 1-methyl-1H-pyrazole-5-carboxamide.

Step 2: 2-(6-(1-Methyl-1H-1,2,4-triazole-5-carboxamido)-1H-pyrrolo[2,3-b]pyridin-2-yl)benzoic acid (6)

To a mixture of methyl 2-(6-(1-methyl-1H-1,2,4-triazole-5-carboxamido)-1-(methyl sulfonyl)-1H-pyrrolo[2,3-b]pyridin-2-yl)benzoate (6a) (100 mg, 0.22 mmol) in THF (5 mL) NaOH (10% solution in H$_2$O, 5 mL) was added and the mixture was stirred at rt overnight. The pH of the mixture was adjusted to pH=4 with aqueous HCl. The mixture was concentrated to dryness and the residue was purified by preparative HPLC to give the title compound as a white solid. $^1$H NMR (500 MHz, DMSO-d$_6$): δ ppm 12.95 (s, 1H), 11.94 (s, 1H), 10.04 (s, 1H), 8.18 (s, 1H), 8.05-8.03 (m, 1H), 7.88-7.86 (m, 1H), 7.77-7.76 (m, 1H), 7.66-7.60 (m, 2H), 7.52-7.48 (m, 1H), 6.52 (s, 1H), 4.22 (s, 3H). (ESI): m/z 363.1 [M+H]$^+$.

Example 7: N-(2-(2-Carbamoylphenyl)-1H-pyrrolo[2,3-b]pyridin-6-yl)-1-methyl-1H-1,2,4-triazole-5-carboxamide (7)

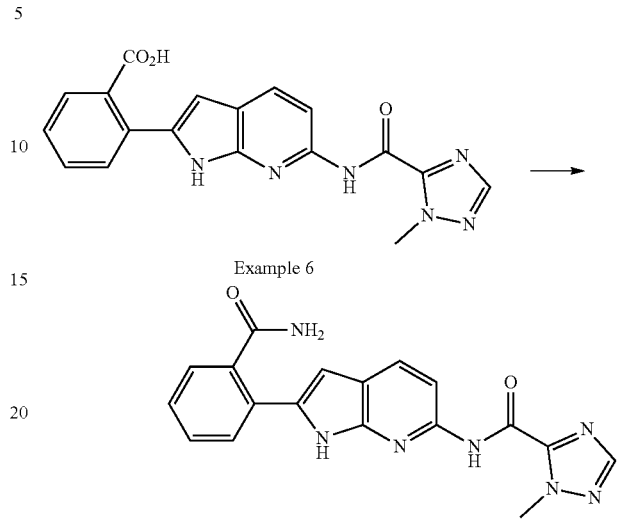

To a mixture of methyl 2-(6-(1-methyl-1H-1,2,4-triazole-5-carboxamido)-1-(methyl sulfonyl)-1H-pyrrolo[2,3-b]pyridin-2-yl)benzoate (Example 6) (80 mg, 0.22 mmol) in DMF (5 mL) HATU (126 mg, 0.33 mmol), DIPEA (30 mg, 0.44 mmol) and NH$_4$Cl (15 mg, 0.26 mmol) were added and the mixture was stirred at rt overnight. The mixture was concentrated to dryness and the residue was purified by preparative HPLC to give the title compound as a white solid. $^1$H NMR (400 MHz, DMSO-d$_6$): δ ppm 11.93 (s, 1H), 10.07 (s, 1H), 8.19 (s, 1H), 8.06-7.85 (m, 3H), 7.75-7.73 (m, 1H), 7.56-7.50 (m, 2H), 7.44-7.41 (m, 2H), 6.74 (s, 1H), 4.22 (s, 3H). (ESI): m/z 362.1 [M+H]$^+$.

Example 8: N-(2-(2-(Dimethylcarbamoyl)phenyl)-1H-pyrrolo[2,3-b]pyridin-6-yl)-1-methyl-1H-1,2,4-triazole-5-carboxamide (8)

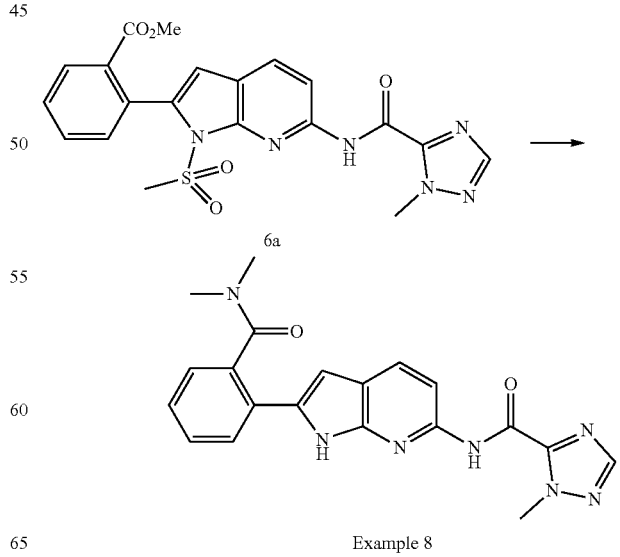

To a mixture of methyl 2-(6-(1-methyl-1H-1,2,4-triazole-5-carboxamido)-1-(methyl sulfonyl)-1H-pyrrolo[2,3-b]pyridin-2-yl)benzoate (6a) (100 mg, 0.22 mmol) in MeOH (1 mL) was added NHMe₂ (1M solution in MeOH, 10 mL) and the mixture was stirred at 70° C. overnight. The mixture was concentrated to dryness and the residue was purified by preparative HPLC to give the title compound as a white solid. ¹H NMR (500 MHz, DMSO-d₆): δ 12.03 (s, 1H), 10.08 (s, 1H), 8.19 (s, 1H), 8.07-8.05 (m, 1H), 7.87-7.80 (m, 2H), 7.56-7.31 (m, 3H), 6.50 (s, 1H), 4.22 (s, 3H), 2.96 (s, 3H), 2.60 (s, 3H). (ESI): m/z 390.2 [M+H]⁺.

Example 9: 1-Methyl-5-((2-(2-(trifluoromethyl)phenyl)-1H-pyrrolo[2,3-b]pyridin-6-yl) carbamoyl)-1H-pyrazole-3-carboxylic Acid (9)

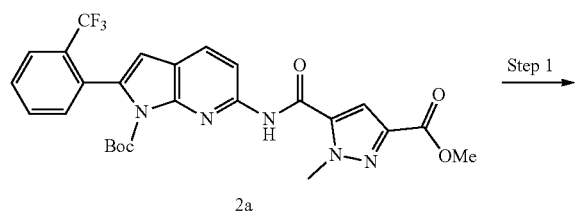

2a

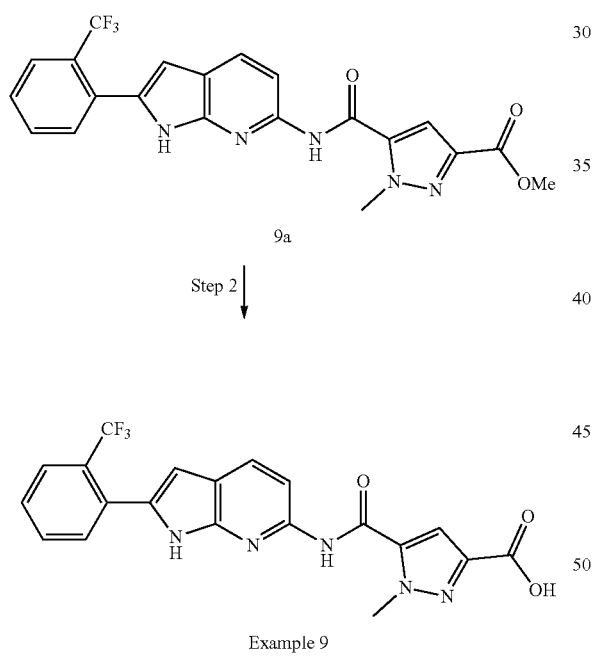

Step 1: Methyl 1-methyl-5-((2-(2-(trifluoromethyl)phenyl)-1H-pyrrolo[2,3-b]pyridin-6-yl) carbamoyl)-1H-pyrazole-3-carboxylate (9a)

To a mixture of tert-butyl 6-(3-(methoxycarbonyl)-1-methyl-1H-pyrazole-5-carboxamido)-2-(2-(trifluoromethyl)phenyl)-1H-pyrrolo[2,3-b]pyridine-1-carboxylate (2a) (150 mg, 0.27 mmol) in DCM (5 mL) TFA (5 mL) was added and the mixture was stirred at rt overnight. The mixture was concentrated to dryness and the residue was purified by preparative HPLC to give the title compound as a white solid.

Step 2: 1-Methyl-5-((2-(2-(trifluoromethyl)phenyl)-1H-pyrrolo[2,3-b]pyridin-6-yl) carbamoyl)-1H-pyrazole-3-carboxylic Acid (9)

Methyl 1-methyl-5-((2-(2-(trifluoromethyl)phenyl)-1H-pyrrolo[2,3-b]pyridin-6-yl) carbamoyl)-1H-pyrazole-3-carboxylate (9a) (111 mg, 0.25 mmol) was dissolved in a mixture of aqueous NaOH solution (10%, 2 mL) and THF (2 mL) and the mixture was stirred at rt for 1 h. The mixture was concentrated to dryness. Water was added and the pH was acidified to pH=4 using aqueous citric acid solution. The precipitated solid was filtered and dried to give the title compound. ¹H NMR (500 MHz, DMSO-d): δ ppm 12.90 (s, 1H), 11.87 (s, 1H), 10.83 (s, 1H), 8.04-8.03 (m, 1H), 7.91-7.90 (m, 1H), 7.84-7.79 (m, 2H), 7.72-7.66 (m, 3H), 6.55 (s, 1H), 4.19 (s, 3H). (ESI): m/z 430.1 [M+H]⁺.

Example 10: N-(3-Bromo-2-(2-(difluoromethyl)phenyl)-1H-pyrrolo[2,3-b]pyridin-6-yl)-1-methyl-1H-1-1,2,4-triazole-5-carboxamide (10)

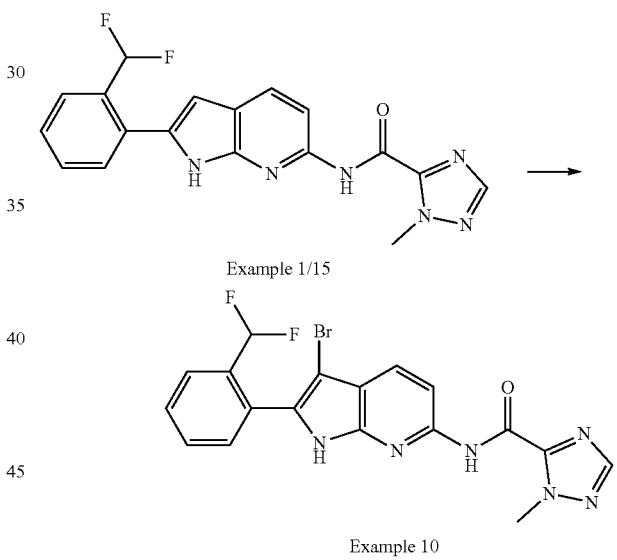

To a mixture of N-(2-(2-(difluoromethyl)phenyl)-1H-pyrrolo[2,3-b]pyridin-6-yl)-1-methyl-1H-1,2,4-triazole-5-carboxamide (Example 1/15) in DMF (4 mL) was added NBS (39 mg, 0.217 mol) at −60° C. to −55° C. The mixture was stirred at the same temperature for 2 h. The mixture was diluted with water (50 mL) and extracted with EtOAc (2×100 mL). The combined organic layers were dried over anhydrous Na₂SO₄, filtered and concentrated to dryness. The residue was purified by preparative HPLC to give the title compound as a white solid. ¹H NMR (DMSO-d₆, 400 MHz): δ ppm 12.44 (s, 1H), 10.26 (s, 1H), 8.19 (s, 1H), 8.02 (s, 1H), 7.83-7.80 (m, 1H), 7.73-7.70 (m, 2H), 7.59-7.57 (m, 1H), 6.89 (t, J=54.4 Hz, 1H), 4.22 (s, 3H). (ESI): m/z 446.9 [M+H]⁺.

Example 10/1: N-(3-Bromo-2-(5-chloro-2-(difluoromethyl)phenyl)-1H-pyrrolo[2,3-b]pyridin-6-yl)-1-methyl-1H-1,2,4-triazole-5-carboxamide (10/1)

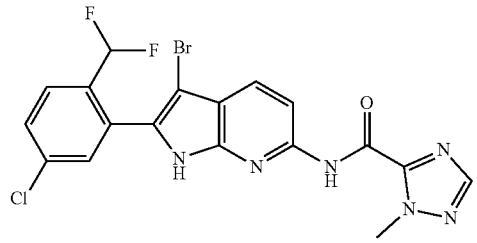 [SMILES: Cn1ncnc1C(=O)Nc1ccc2c(Br)c(-c3cc(Cl)ccc3C(F)F)[nH]c2n1]

The title compound was prepared similar as described for Example 10 using in Step 1 N-(2-(5-chloro-2-(difluoromethyl)phenyl)-1H-pyrrolo[2,3-b]pyridin-6-yl)-1-methyl-1H-1,2,4-triazole-5-carboxamide (Example 1/34) in place of N-(2-(2-(difluoromethyl) phenyl)-1H-pyrrolo[2,3-b]pyridin-6-yl)-1-methyl-11H-1,2,4-triazole-5-carboxamide (Example 1/15). $^1$H NMR (500 MHz, DMSO-$d_6$): δ ppm 12.48 (s, 1H), 10.27 (s, 1H), 8.19 (s, 1H), 8.03-8.02 (m, 2H), 7.86-7.71 (m, 3H), 6.89 (t, J=54.5 Hz, 1H), 4.22 (s, 3H). (ESI): m/z 481.0 [M+H]$^+$.

Example 11: N-(3-Chloro-2-(2-(difluoromethyl)-5-fluorophenyl)-1H-pyrrolo[2,3-b]pyridin-6-yl)-1-methyl-1H-1,2,4-triazole-5-carboxamide (11)

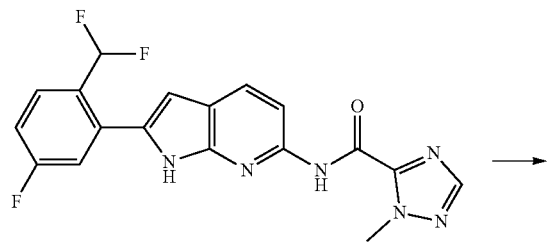

Example 4/9

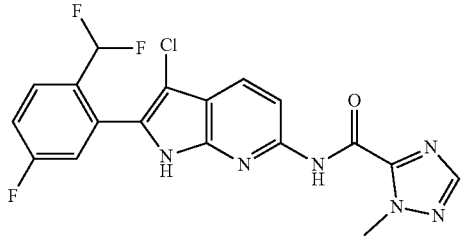

11

To a mixture of N-(2-(2-(difluoromethyl)-5-fluorophenyl)-1H-pyrrolo[2,3-b]pyridin-6-yl)-1-methyl-1H-1,2,4-triazole-5-carboxamide (Example 4/9) (105 mg, 0.272 mmol) in DMF (4 mL) was added NCS (36 mg, 0.272 mol). The mixture was stirred at rt overnight. The mixture was concentrated to dryness and the residue was purified by preparative HPLC to give the desired title compound as a white solid. $^1$H NMR (DMSO-ds, 400 MHz): δ ppm 12.40 (s, 1H), 10.27 (s, 1H), 8.19 (s, 1H), 8.11 (d, J=8.4 Hz, 1H), 8.02 (d, J=8.4 Hz, 1H), 7.91-7.88 (m, 1H), 7.58-7.51 (m, 2H), 6.92 (t, J=54.4 Hz, 1H), 4.23 (s, 1H). (ESI): m/z 421.0 [M+H]$^+$.

Example 12: 3-(6-(1-Methyl-1H-1,2,4-triazole-5-carboxamido)-1H-pyrrolo[2,3-b]pyridin-2-yl)benzoic Acid (12)

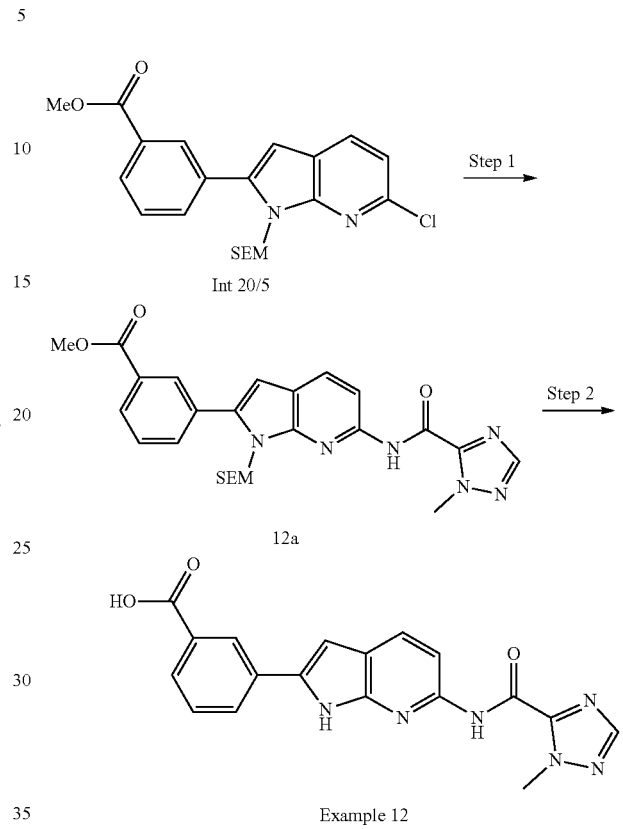

Step 1: Methyl 3-(6-(1-methyl-1H-1,2,4-triazole-5-carboxamido)-1-((2-(trimethylsilyl)ethoxy)methyl)-1H-pyrrolo[2,3-b]pyridin-2-yl)benzoate (12a)

A mixture of methyl 3-(6-chloro-1-((2-(trimethylsilyl)ethoxy)methyl)-1H-pyrrolo[2,3-b]pyridin-2-yl)benzoate (Int 20/5) (250 mg, 0.72 mmol), 1-methyl-1H-1,2,4-triazole-5-carboxamide (Int 3) (137 mg, 1.082 mmol), $K_2CO_3$ (298 mg, 2.63 mmol), tBuXPhos (300 mg) and $Pd_2(dba)_3$ (300 mg) in DMF (5 mL) was stirred at 140° C. for 5 h. The mixture was diluted with water (100 ml) and extracted with DCM (3×100 mL). The combined organic layers were dried over anhydrous $Na_2SO_4$, filtered and concentrated to dryness. The residue was purified by silica gel column chromatography (PE/EtOAc=20:1) to give the title compound as a yellow solid.

Step 2: 3-(6-(1-Methyl-1H-1,2,4-triazole-5-carboxamido)-1H-pyrrolo[2,3-b]pyridin-2-yl)benzoic Acid (12)

To a mixture of methyl 3-(6-(1-methyl-1H-1,2,4-triazole-5-carboxamido)-1-((2-(trimethylsilyl)ethoxy)methyl)-1H-pyrrolo[2,3-b]pyridin-2-yl)benzoate (12a) (0.50 g, 0.99 mmol) in DCM (3 mL) was added $BF_3·Et_2O$ (5 mL). The mixture was stirred at rt for 2 h. The mixture was diluted with water (2 mL) and concentrated. The residue was dissolved in MeOH (10 mL), and adjusted to pH=11 with 10% aqueous KOH. The mixture was stirred at rt for 2 h. The mixture was diluted with water (300 mL) and extracted with EtOAc (3×50 mL). The combined organic layers were dried over anhydrous Na₂SO₄, filtered and concentrated to dryness. The residue was purified by silica gel chromatography (DCM/MeOH=10:1) to afford the title compound as a white solid. ¹H NMR (DMSO-d₆, 400 MHz): δ ppm 12.27 (s, 1H), 10.05 (s, 1H), 8.49 (s, 1H), 8.19 (s, 1H), 8.13 (d, J=7.6 Hz, 1H), 8.05 (d, J=8.8 Hz, 1H), 7.91-7.87 (m, 2H), 7.57 (dd, J₁=J₂=7.6 Hz, 1H), 7.01 (s, 1H), 4.22 (s, 3H). (ESI): m/z 363.0 [M+H]⁺.

Example 12/1: 4-(6-(1-Methyl-1H-1,2,4-triazole-5-carboxamido)-1H-pyrrolo[2,3-b]pyridin-2-yl)benzoic Acid (12/1)

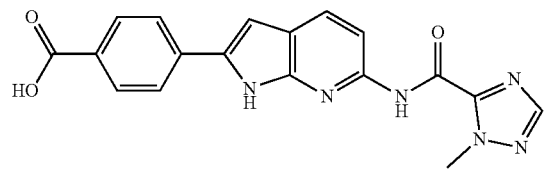 [SMILES: Cn1ncnc1C(=O)Nc1ccc2cc(-c3ccc(C(=O)O)cc3)[nH]c2n1]

The title compound was prepared similar as described for Example 12 using in step 1 methyl 4-(6-chloro-1-((2-(trimethylsilyl)ethoxy)methyl)-1H-pyrrolo[2,3-b]pyridin-2-yl)benzoate (Int 20/6) in place of methyl 3-(6-chloro-1-((2-(trimethylsilyl)ethoxy)methyl)-1H-pyrrolo[2,3-b]pyridin-2-yl)benzoate (Int 20/5). ¹H NMR (DMSO-d₆, 400 MHz): δ ppm 8.18 (s, 1H), 8.07 (d, J=8.8 Hz, 1H), 8.00-7.96 (m, 4H), 7.88 (d, J=8.4 Hz, 1H), 7.06 (s, 1H), 4.22 (s, 3H). (ESI): m/z 363.1 [M+H]⁺.

Example 13: N-(2-(2-(Difluoromethyl)phenyl)-1H-pyrrolo[2,3-b]pyridin-6-yl)-N,1-dimethyl-1H-1,2,4-triazole-5-carboxamide (13)

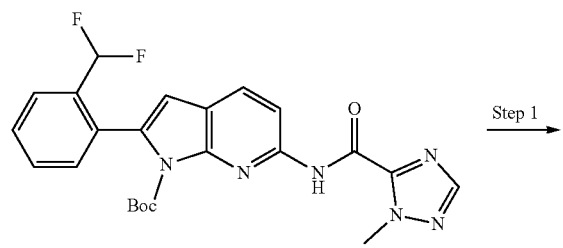

Example 1/15, Step 1

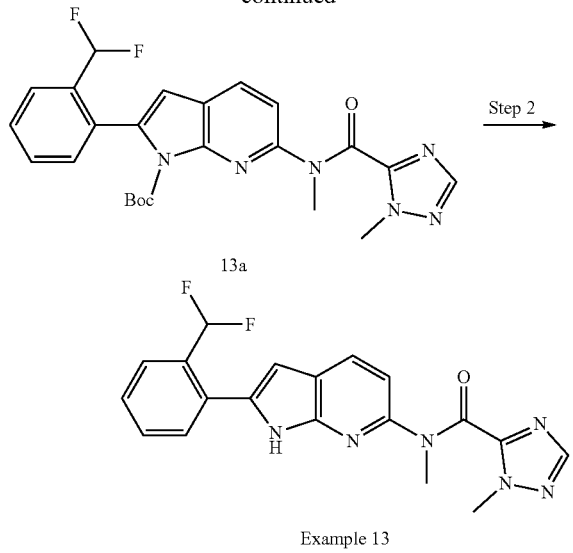

Example 13

Step 1: tert-Butyl 2-(2-(difluoromethyl)phenyl)-6-(N,1-dimethyl-1H-1,2,4-triazole-5-carboxamido)-1H-pyrrolo[2,3-b]pyridine-1-carboxylate (13a)

A mixture of tert-butyl 2-(2-(difluoromethyl)phenyl)-6-(1-methyl-1H-1,2,4-triazole-5-carboxamido)-1H-pyrrolo[2,3-b]pyridine-1-carboxylate (Intermediate for Example 1/15 Step 1) (300 mg, 0.64 mmol), Cs₂CO₃ (313 mg, 0.96 mmol) and MeI (109 mg, 0.77 mmol) in DMF (10 mL) was stirred at rt overnight. The mixture was concentrated to dryness and the residue was purified by preparative HPLC to give the title compound as white solid.

Step 2: N-(2-(2-(Difluoromethyl)phenyl)-1H-pyrrolo[2,3-b]pyridin-6-yl)-N,1-dimethyl-1H-1,2,4-triazole-5-carboxamide (13)

To a mixture of tert-butyl 2-(2-(difluoromethyl)phenyl)-6-(N,1-dimethyl-1H-1,2,4-triazole-5-carboxamido)-1H-pyrrolo[2,3-b]pyridine-1-carboxylate (13a) (250 mg, 0.52 mmol) in DCM (5 mL) was added TFA (2.5 mL) and the mixture was stirred at rt overnight. The mixture was concentrated to dryness and the residue was purified by preparative HPLC to give the title compound as a white solid. ¹H NMR (500 MHz, DMSO-d₆): δ ppm 12.13 (s, 1H), 7.98-7.96 (m, 1H), 7.81-7.80 (m, 1H), 7.73-7.68 (m, 3H), 7.62-7.59 (m, 1H), 7.25-6.98 (m, 2H), 6.56 (s, 1H), 4.03 (s, 3H), 3.53 (s, 3H). (ESI): m/z 383.2 [M+H]⁺.

Example 14: N-(3-Cyano-2-(2-(difluoromethyl)phenyl)-1H-pyrrolo[2,3-b]pyridin-6-yl)-1-methyl-1H-1,2,4-triazole-5-carboxamide (14)

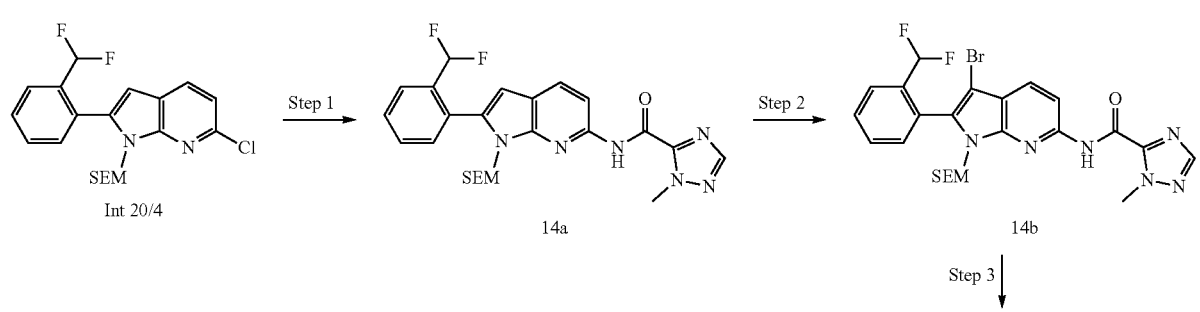

Step 3

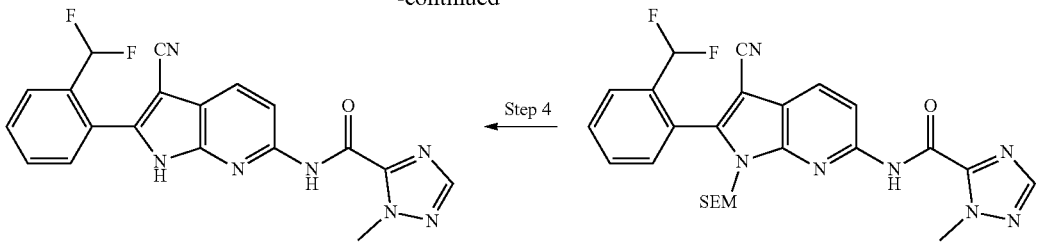

Example 14　　14c

Step 1: N-(2-(2-(Difluoromethyl)phenyl)-1-((2-(trimethylsilyl)ethoxy)methyl)-1H-pyrrolo[2,3-b]pyridin-6-yl)-1-methyl-1H-1,2,4-triazole-5-carboxamide (14a)

A mixture of 6-chloro-2-(2-(difluoromethyl)phenyl)-1-((2-(trimethylsilyl)ethoxy)methyl)-1H-pyrrolo[2,3-b]pyridine (Int 20/4) (20 g, 49 mmol), 1-methyl-1H-1,2,4-triazole-5-carboxamide (Int 3) (12.4 g, 98 mmol), $K_2CO_3$ (13.5 g, 98 mmol), tBuXPhos (12.0 g) and $Pd_2(dba)_3$ (12.0 g) in DMF (200 mL) was stirred at 135° C. for 12 h. The mixture was diluted with water (1000 ml) and extracted with DCM (3×800 mL). The combined organic layers were dried over $Na_2SO_4$, filtered and concentrated to dryness. The residue was purified by silica gel column chromatography (PE/EA=20:1) to give the title compound as a yellow solid.

Step 2: N-(3-Bromo-2-(2-(difluoromethyl)phenyl)-1-((2-(trimethylsilyl)ethoxy)methyl)-1H-pyrrolo[2,3-b]pyridin-6-yl)-1-methyl-1H-1,2,4-triazole-5-carboxamide (14b)

To a mixture of N-(2-(2-(difluoromethyl)phenyl)-1-((2-(trimethylsilyl)ethoxy)methyl)-1H-pyrrolo[2,3-b]pyridin-6-yl)-1-methyl-1H-1,2,4-triazole-5-carboxamide (14a) (220 mg, 0.44 mmol) in DMF (10 mL) was added NBS (79 mg, 0.44 mmol) at −60° C. to −55° C. and the mixture was stirred at the same temperature for 3 h. The mixture was diluted with water (30 ml) and extracted with EtOAc (3×10 mL). The combined organic layers were dried over $Na_2SO_4$, filtered and concentrated to dryness. The residue was purified by silica gel column chromatography (PE/EtOAc=6:1) to give the title compound as a white solid.

Step 3: N-(3-Cyano-2-(2-(difluoromethyl)phenyl)-1-((2-(trimethylsilyl)ethoxy)methyl)-1H-pyrrolo[2,3-b]pyridin-6-yl)-1-methyl-1H-1,2,4-triazole-5-carboxamide (14c)

A mixture of N-(3-bromo-2-(2-(difluoromethyl)phenyl)-1-((2-(trimethylsilyl)ethoxy) methyl)-1H-pyrrolo[2,3-b]pyridin-6-yl)-1-methyl-1H-1,2,4-triazole-5-carboxamide (14b) (150 mg, 0.26 mmol), zinc cyanide (92 mg, 0.78 mmol) and $Pd(PPh_3)_4$ (150 mg, 0.13 mmol) in DMF (6 mL) was heated under $N_2$ at 125° C. for 4 h. The mixture was cooled to rt and diluted with water. The mixture was extracted with DCM (2×300 mL). The combined organic layers were dried over $Na_2SO_4$, filtered and concentrated. The residue was purified by silica gel column chromatography (PE/EtOAc=4:1) to give the title compound as a yellow solid.

Step 4: N-(3-Cyano-2-(2-(difluoromethyl)phenyl)-1H-pyrrolo[2,3-b]pyridin-6-yl)-1-methyl-1H-1,2,4-triazole-5-carboxamide (14)

To a mixture of N-(3-cyano-2-(2-(difluoromethyl)phenyl)-1-((2-(trimethylsilyl)ethoxy) methyl)-1H-pyrrolo[2,3-b]pyridin-6-yl)-1-methyl-1H-1,2,4-triazole-5-carboxamide (14c) (110 mg, 0.21 mmol) in DCM (3 mL) was added $BF_3.Et_2O$ (0.5 mL) and the mixture was stirred at rt for 2 h. The mixture was diluted with water (1 mL) and concentrated to dryness. The residue was dissolved in MeOH (10 mL) and the pH was adjusted to pH=11 with 10% aqueous KOH solution. The mixture was stirred at rt for 2 h. The mixture was diluted with water (30 mL), and extracted with EtOAc (3×20 mL). The combined organic layers were dried over $Na_2SO_4$, filtered and concentrated to dryness. The residue was purified by silica gel column chromatography (DCM/MeOH=10:1) to give the title compound as a white solid. $^1H$ NMR (DMSO-$d_6$, 400 MHz): δ ppm 13.11 (s, 1H), 10.37 (d, J=4.2 Hz, 1H), 8.27-8.25 (m, 1H), 8.19 (s, 1H), 8.10-8.07 (m, 1H), 7.86-7.85 (m, 1H), 7.79-7.75 (m, 2H), 7.73-7.70 (m, 1H), 7.04 (t, J=54.4 Hz, 1H), 4.21 (s, 3H). (ESI): m/z 394.1 $[M+H]^+$.

Biological Assays

AhR Direct Luciferase Reporter Assay in HepG2 Cells

A stable cell line (HepG2 CYP1A1-LUC) was used in which part of the promoter region of the human CYP1A1 gene is stably integrated into the genome of human HepG2 hepatocytes (DSZM #ACC 180) in front of a *Photinus pyralis* Firefly Luciferase gene. A 1210 bp fragment comprising part of the human CYP1A1 promoter was isolated via SacI and BglIII restriction digestion from Lightswitch Clone S714555 (SwitchGearGenomics) and inserted between the SacI and BglIII sites in pGL4.30 (Promega #E8481) in front of the Firefly Luciferase gene. The resulting vector was linearized with NotI, transfected into HepG2 cells (DSMZ #ACC 180) and stably transfected clones selected with 250 µg/ml Hygromycin B. After repetitive rounds of subcloning and testing for robustly regulated luciferase activity after AhR agonist stimulation, a stable clonal HepG2 CYP1A1-Luc cell line was selected.

The HepG2 CYP1A1-Luc cells do express basal luciferase activity that can be increased via potent AhR agonists or decreased via potent AhR antagonists, added to the growth medium of the cells.

In typical reporter assays performed with this cell line, cells are grown in 96-well plates and AhR modulators are titrated into the growth medium in serial dilutions in RPMI-1640 Medium (Sigma #R7509) supplemented with 8,6% fetal calf serum (Sigma #F7524) and containing either no exogenous AhR agonist or 10 nM of the potent AhR agonist VAF347 (Calbiochem #182690). Cells are further cultivated for 18 hours and luciferase activities are determined from extracts of cells in buffers containing D-Luciferine and ATvP using a LUMIstar Optima microplate Luminometer from BMG Labtech.

The AhR antagonistic potency of the example compounds is shown in Table 1 below (A=IC$_{50}$<100 nM, B=IC$_{50}$ 100 nM–1 μM, C=IC$_{50}$>1 μM)

Table 1

| Example # | AhR potency |
|---|---|
| 1 | A |
| 1/1 | A |
| 1/2 | B |
| 1/3 | B |
| 1/4 | C |
| 1/5 | C |
| 1/6 | A |
| 1/7 | A |
| 1/8 | A |
| 1/9 | A |
| 1/10 | B |
| 1/11 | A |
| 1/12 | A |
| 1/13 | A |
| 1/14 | A |
| 1/15 | A |
| 1/16 | A |
| 1/17 | C |
| 1/18 | B |
| 1/19 | B |
| 1/20 | A |
| 1/21 | B |
| 1/22 | A |
| 1/23 | C |
| 1/24 | A |
| 1/25 | A |
| 1/26 | A |
| 1/27 | A |
| 1/28 | A |
| 1/29 | A |
| 1/30 | A |
| 1/31 | B |
| 1/32 | A |
| 1/33 | A |
| 1/34 | A |
| 1/35 | A |
| 2 | B |
| 3 | B |
| 4 | A |
| 4/1 | A |
| 4/2 | B |
| 4/3 | B |
| 4/4 | A |
| 4/6 | B |
| 4/7 | A |
| 4/8 | A |
| 4/9 | A |
| 5 | B |
| 5/1 | A |
| 5/2 | A |
| 6 | C |
| 7 | B |
| 8 | C |
| 12/1 | C |
| 14 | A |

What is claimed is:

1. A compound represented by Formula (I), or an enantiomer, diastereomer, tautomer, solvate, prodrug or pharmaceutical acceptable salt thereof:

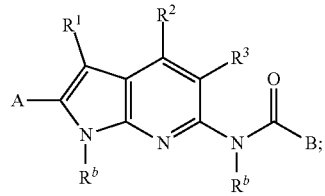

wherein:
A and B are independently selected from 6- to 10-membered mono- or bicyclic aryl and 5- to 10-membered mono- or bicyclic heteroaryl containing 1 to 4 heteroatoms independently selected from N, O and S,
  wherein aryl and heteroaryl are unsubstituted or substituted with 1 to 7 substituents independently selected from the group consisting of halogen, OH, CN, C$_{1-6}$-alkyl, O—C$_{1-6}$-alkyl, C(O)OR$^a$, OC(O)R$^a$, S(O)—C$_{1-6}$-alkyl, S(O)$_2$—C$_{1-6}$-alkyl, N(R$^a$)$_2$, C(O)N(R$^a$)$_2$, NR$^a$C(O)—C$_{1-6}$-alkyl, S(O)$_2$N(R$^a$)$_2$, NR$^a$S(O)$_2$—C$_{1-6}$-alkyl and C$_{3-6}$-cycloalkyl,
    wherein the alkyl and cycloalkyl are unsubstituted or substituted with 1 to 3 substituents independently selected from the group consisting of halogen, C$_{1-3}$-alkyl, halo-C$_{1-3}$-alkyl, OH, CN and oxo, or
  wherein two substituents on the aryl or heteroaryl group together with the atoms they are attached to may form a 5- to 7-membered saturated or partially unsaturated carbocyclic ring or heterocyclic ring containing 1 to 3 heteroatoms independently selected from O, N and S,
    wherein the carbocyclic or heterocyclic ring is unsubstituted or substituted with 1 to 5 substituents independently selected from the group consisting of halogen, C$_{1-6}$-alkyl and halo-C$_{1-6}$-alkyl;
R$^1$, R$^2$, R$^3$ are each independently selected from hydrogen, halogen, C$_{1-3}$-alkyl, halo-C$_{1-3}$-alkyl, OH, O-C$_{1-3}$-alkyl, and CN;
R$^a$ is hydrogen or C$_{1-6}$-alkyl; and
R$^b$ is hydrogen or C$_{1-6}$-alkyl.

2. The compound of claim 1, wherein R$^b$ is hydrogen.

3. The compound of claim 1, wherein A is substituted with 1 to 5 substituents independently selected from halogen, C$_{1-6}$-alkyl, halo-C$_{1-6}$-alkyl, CN, SO$_2$CH$_3$, C(O)OR$^a$, C(O)N(R$^a$)$_2$ and C$_{3-6}$-cycloalkyl which is unsubstituted or substituted with C$_{1-3}$-alkyl or halo-C$_{1-3}$-alkyl.

4. The compound of claim 1, wherein:
A is

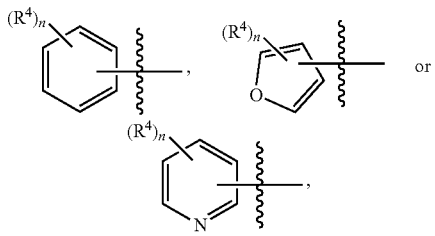

wherein:
R$^4$ is independently halogen, OH, CN, C$_{1-6}$-alkyl, O—C$_{1-6}$-alkyl, C(O)OR$^a$, OC(O)R$^a$, S(O)—C$_{1-6}$-alkyl, S(O)$_2$—C$_{1-6}$-alkyl, N(R$^a$)$_2$, C(O)N(R$^a$)$_2$, NR$^a$C(O)—C$_{1-6}$-alkyl, S(O)$_2$N(R$^a$)$_2$, NR$^a$S(O)$_2$—C$_{1-6}$-alkyl and C$_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo;

$R^a$ is hydrogen or $C_{1-6}$-alkyl; and n is 0 to 5.

5. The compound of claim 4, wherein n is 1 to 5 and $R^4$ is independently selected from halogen, $C_{1-6}$-alkyl, halo-$C_{1-6}$-alkyl, CN and $C_{3-6}$-cycloalkyl which is unsubstituted or substituted with 1 or 2 substituents independently selected from the group consisting of halogen, $C_{1-3}$-alkyl and halo-$C_{1-3}$-alkyl.

6. The compound of claim 4, wherein A is

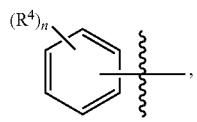

wherein:

$R^4$ is independently halogen, OH, CN, $C_{1-6}$-alkyl, O—$C_{1-6}$-alkyl, $C(O)OR^a$, $OC(O)R^a$, $S(O)$—$C_{1-6}$-alkyl, $S(O)_2$—$C_{1-6}$-alkyl, $N(R^a)_2$, $C(O)N(R^a)_2$, $NR^aC(O)$—$C_{1-6}$-alkyl, $S(O)_2N(R^a)_2$, $NR^aS(O)_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo;

$R^a$ is hydrogen or $C_{1-6}$-alkyl; and n is 0 to 5.

7. The compound of claim 1, wherein:

A is

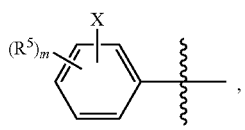

wherein:

X is halogen, $C_{1-6}$-alkyl or $C_{3-6}$-cycloalkyl, wherein the alkyl and cycloalkyl are unsubstituted or substituted with 1 to 3 substituents independently selected from the group consisting of halogen, $C_{1-3}$-alkyl and halo-$C_{1-3}$alkyl;

$R^5$ is independently halogen or CN; and m is 0 to 4.

8. The compound of claim 1, wherein:

A is

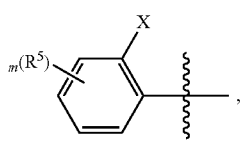

wherein:

X is $CH_3$, $CH_2CH_3$, $CHF_2$ or $CF_3$;

$R^5$ is independently halogen or CN; and m is 0 to 4.

9. The compound of claim 1, wherein B is a 5- or 6-membered heteroaryl containing 1 to 4 heteroatoms independently selected from N, O and S, which is unsubstituted or substituted with 1 to 5 substituents independently selected from the group consisting of halogen, OH, CN, $C_{1-6}$-alkyl, O—$C_{1-6}$-alkyl, $C(O)OR^a$, $OC(O)R^a$, $S(O)$—$C_{1-6}$-alkyl, $S(O)_2$—$C_{1-6}$-alkyl, $N(R^a)_2$, $C(O)N(R^a)_2$, $NR^aC(O)$—$C_{1-6}$-alkyl, $S(O)_2N(R^a)_2$, $NR^aS(O)_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo; and $R^a$ is hydrogen or $C_{1-6}$-alkyl.

10. The compound of claim 1, wherein B is a 5- or 6-membered heteroaryl containing 1 to 3 heteroatoms independently selected from N, O and S, which is unsubstituted or substituted with 1 to 2 substituents independently selected from the group consisting of $C_{1-6}$-alkyl, halo-$C_{1-6}$-alkyl, $C(O)OR^a$, $C(O)N(R^a)_2$ and $C_{3-6}$-cycloalkyl.

11. The compound of claim 1, wherein B is a 9- or 10-membered heteroaryl containing 1 to 4 heteroatoms independently selected from N, O and S, which is unsubstituted or substituted with 1 to 2 substituents independently selected from the group consisting of $C_{1-6}$-alkyl, halo-$C_{1-6}$-alkyl, and $C_{3-6}$-cycloalkyl or wherein B is a 6- or 10-membered aryl, which is unsubstituted or substituted with 1 to 2 substituents independently selected from the group consisting of halogen and $C_{1-6}$-alkyl.

12. The compound of claim 1, wherein:

B is

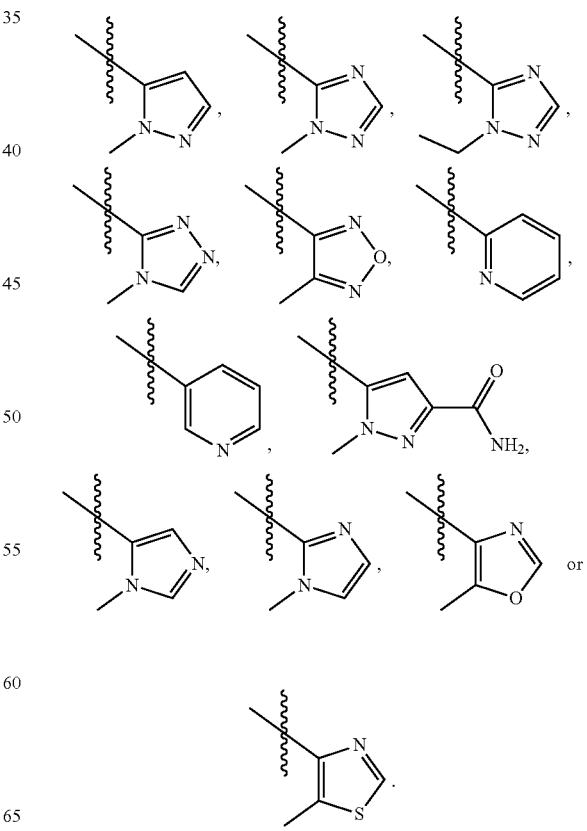

13. The compound of claim 1, wherein:
B is
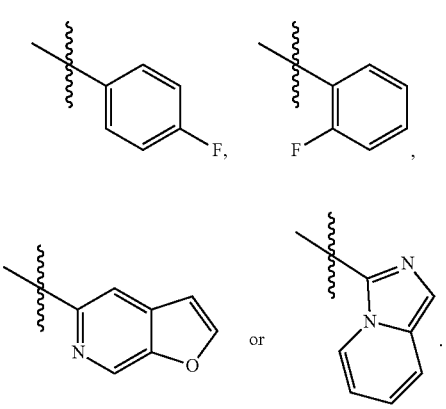
or.
14. The compound of claim 1, wherein each of $R^1$, $R^2$, $R^3$ are hydrogen.
15. The compound of claim 1 which is selected from
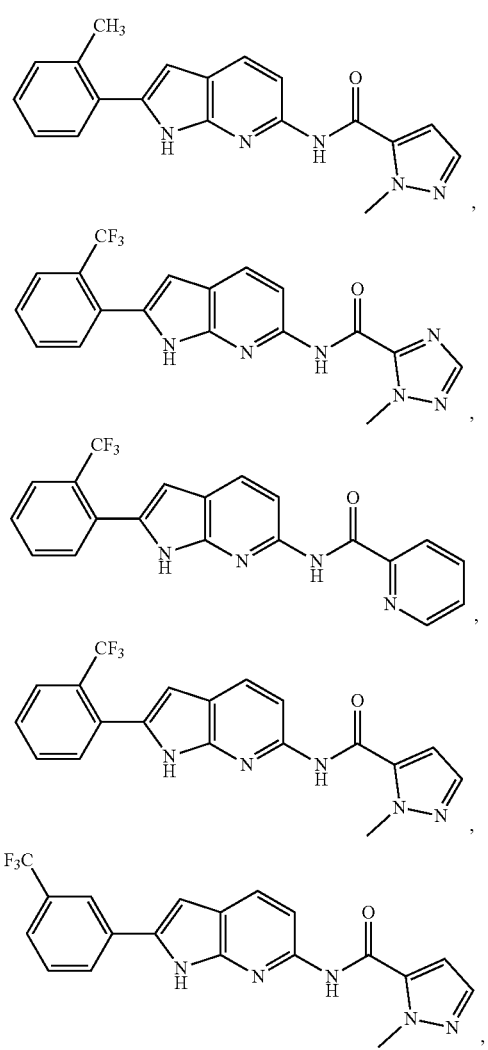
-continued
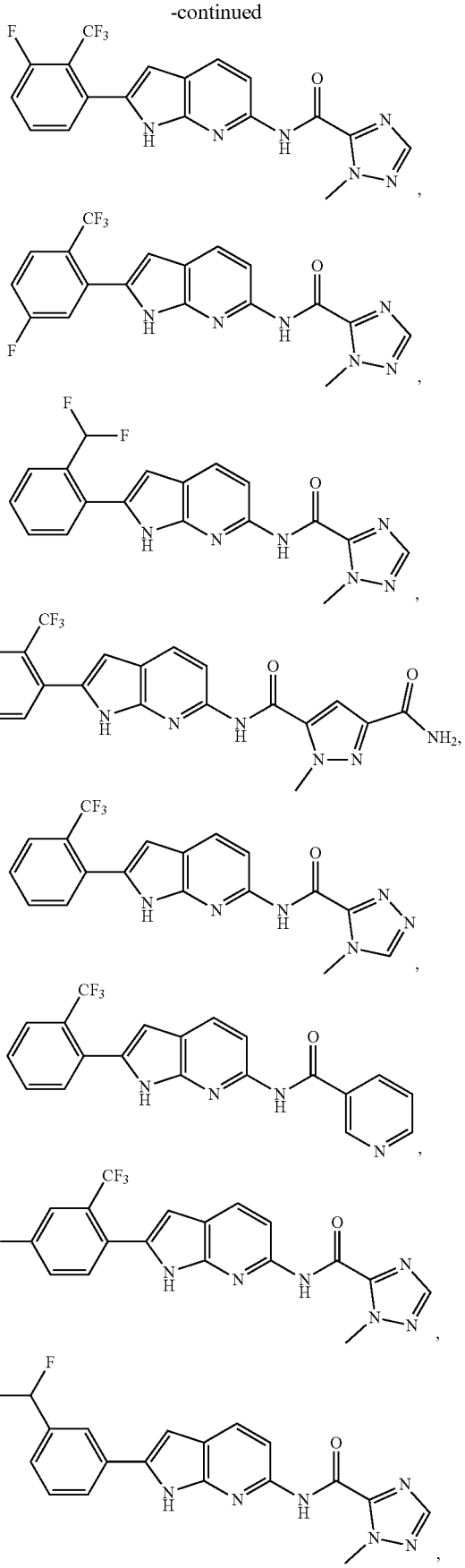

101
-continued
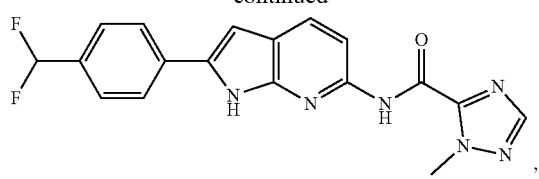
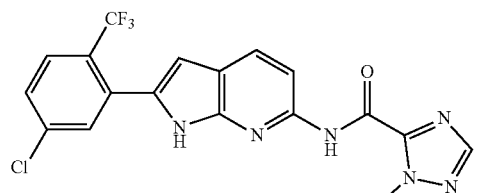
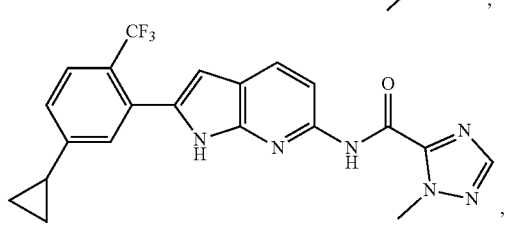
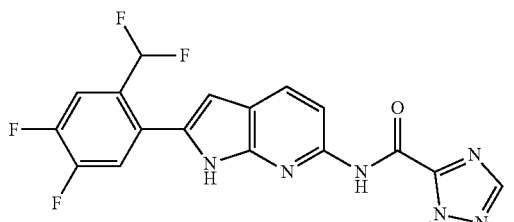
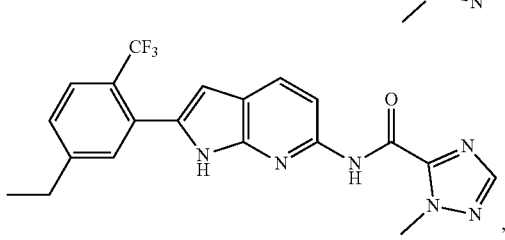
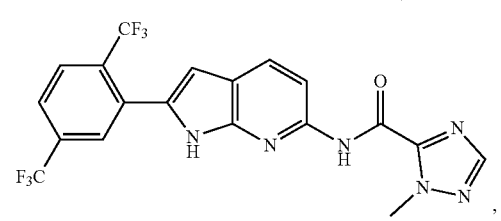
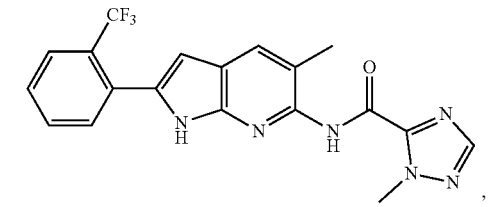
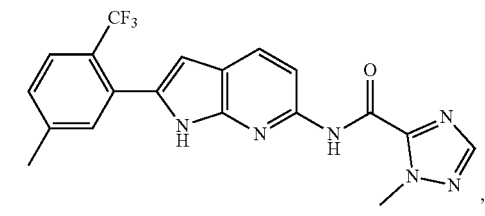
102
-continued
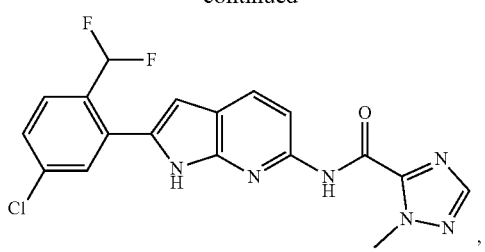
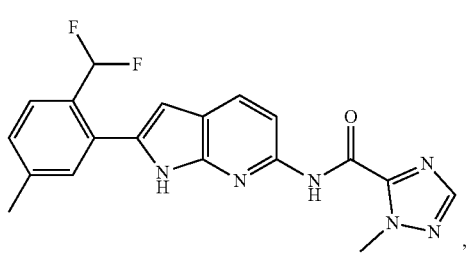
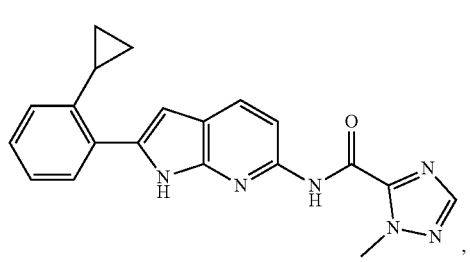
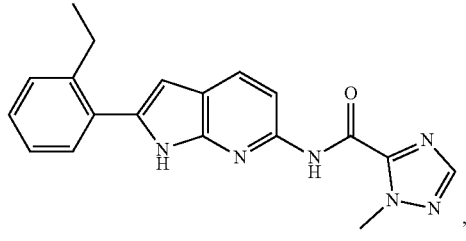
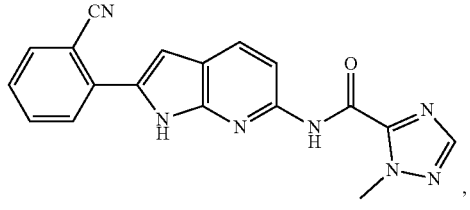
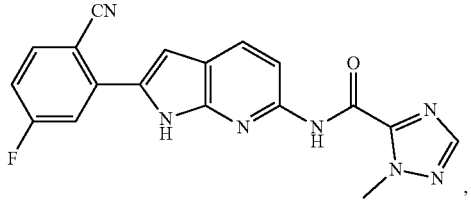
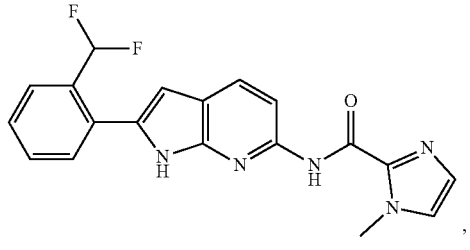

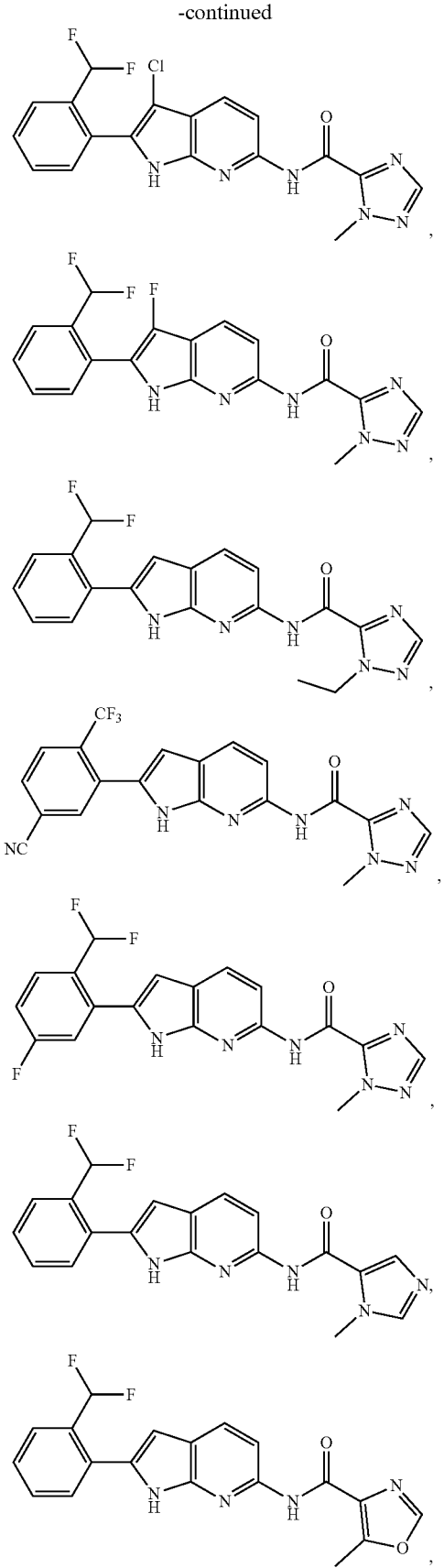

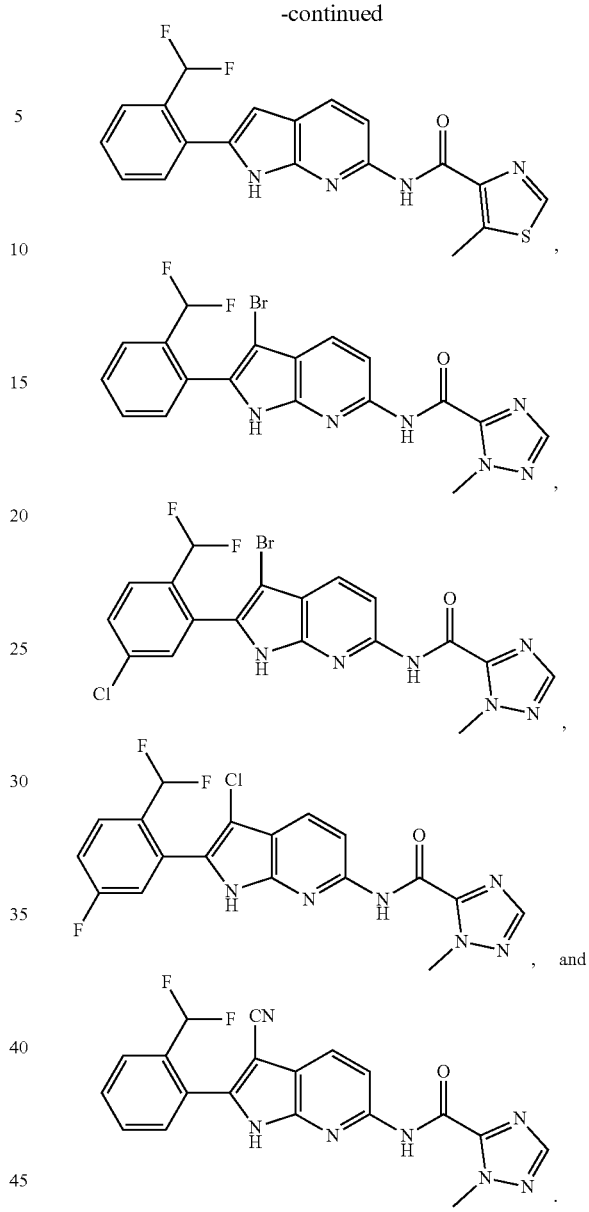

16. A pharmaceutical composition comprising a compound of claim 1, or an enantiomer, diastereomer, tautomer, solvate, prodrug or pharmaceutical acceptable salt thereof, and a physiologically acceptable excipient.

17. A method of treating a disease or condition mediated by aryl hydrocarbon receptor (AhR) in a mammal, wherein the method comprises administering to the mammal in need thereof an effective amount of a compound of claim 1, or an enantiomer, diastereomer, tautomer, solvate, prodrug or pharmaceutical acceptable salt thereof, or a pharmaceutical composition of claim 16 and wherein the disease or condition mediated by aryl hydrocarbon receptor (AhR) is cancer.

18. The method of claim 17, wherein the compound is administered with one or more therapeutic agents for cancer selected from the group consisting of PD-1 agent, PD-L1 agent, CTLA-4 agent, IDO1 inhibitor, chemotherapeutic agent, anticancer vaccine, and cytokine therapy, or wherein the compound is administered under irradiation therapy.

* * * * *

UNITED STATES PATENT AND TRADEMARK OFFICE
CERTIFICATE OF CORRECTION

| | | |
|---|---|---|
| PATENT NO. | : 10,981,908 B2 | Page 1 of 3 |
| APPLICATION NO. | : 16/479130 | |
| DATED | : April 20, 2021 | |
| INVENTOR(S) | : Christoph Steeneck et al. | |

It is certified that error appears in the above-identified patent and that said Letters Patent is hereby corrected as shown below:

In the Specification

Column 2, Line 15:
"thereof." should read: -- thereof --.

Column 2, Line 38:
"$NR^aS(O)_2$-$C_{1-3}$-alkyl and $C_{1-3}$-cycloalkyl," should read: -- $NR^aS(O)_2$-$C_{1-6}$-alkyl and $C_{3-6}$-cycloalkyl, --.

Column 22, Lines 38-42:

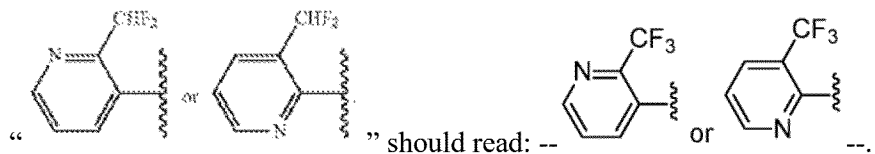 should read: --

Column 23, Line 41:
"$C_{1-6}$-cycloalkyl" should read: -- $C_{3-6}$-cycloalkyl --.

Column 29, Line 30:
"O-(7-azabenzotriazol-1-yl)-N,N,N,N'-tetramethyl-" should read: -- O-(7-azabenzotriazol-1-yl)-N,N,N',N'-tetramethyl- --.

Column 32, Lines 18-25:

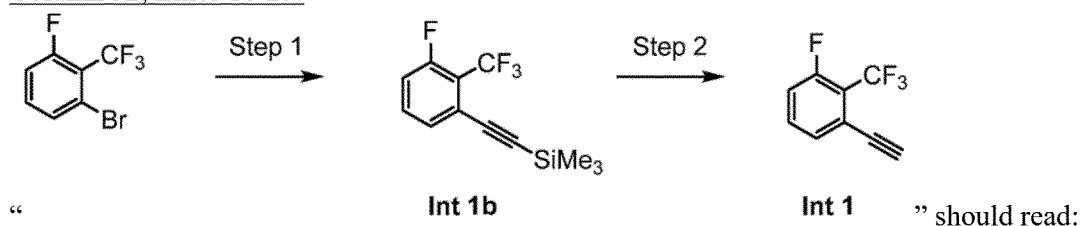 should read:

Signed and Sealed this
Sixth Day of December, 2022

Katherine Kelly Vidal
*Director of the United States Patent and Trademark Office*

CERTIFICATE OF CORRECTION (continued)
U.S. Pat. No. 10,981,908 B2

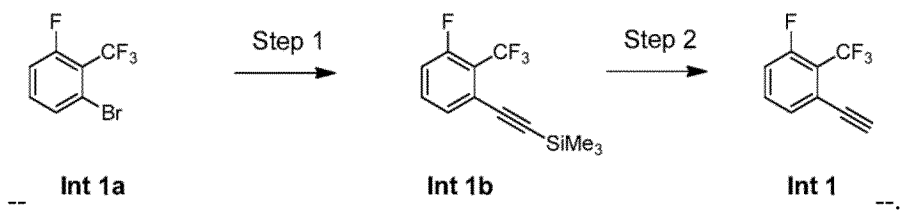

Column 47, Line 59:
"31-ethynyl-2-(trifluorom-" should read: -- 3 1-ethynyl-2-(trifluorom- --.

Column 48, Line 50:
"1-Ethyl-11*H*-1,2,4-triazole-5-carboxamide (Int 7)" should read: -- 1-Ethyl-1*H*-1,2,4-triazole-5-carboxamide (Int 7) --.

Column 49, Lines 5-44:

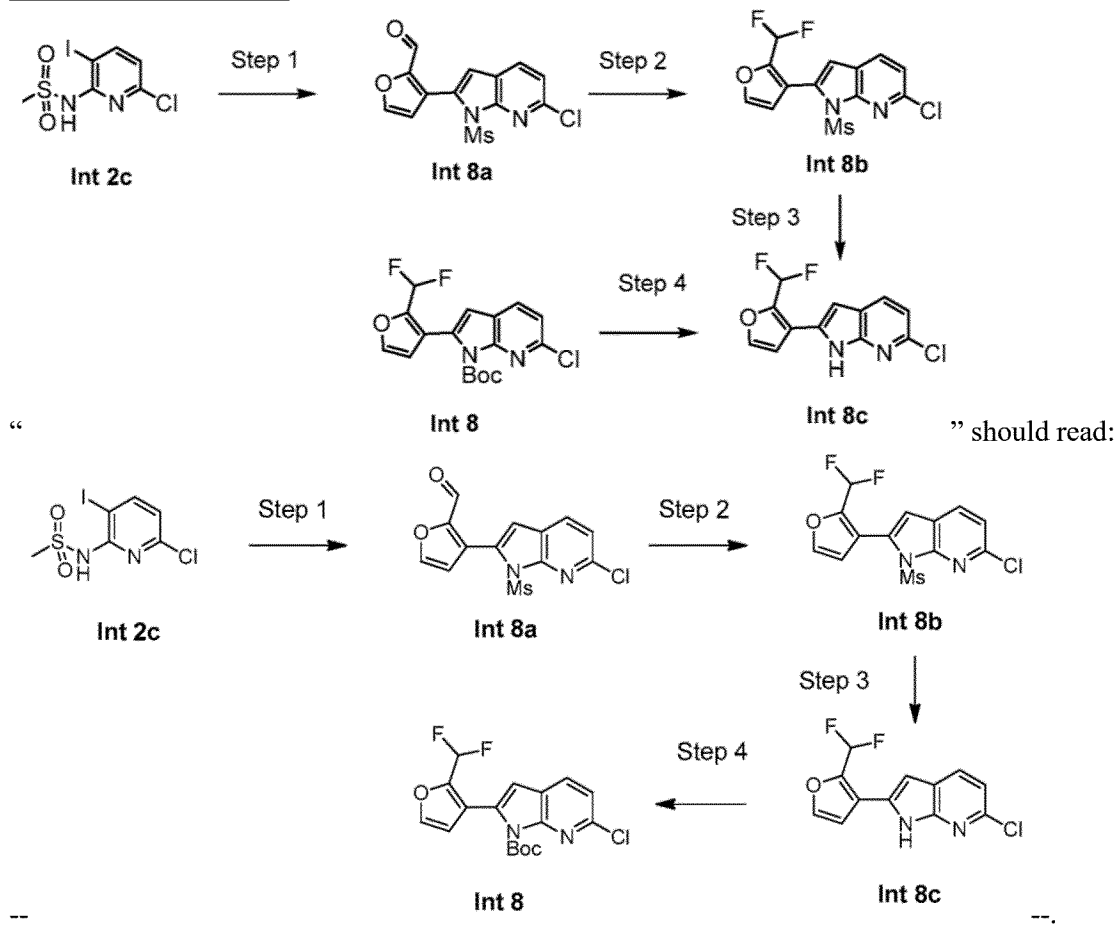

Column 58, Line 49:
"step 34-cyclopropyl-" should read: -- step 3 4-cyclopropyl- --.

CERTIFICATE OF CORRECTION (continued)

Column 60, Lines 8-28:

"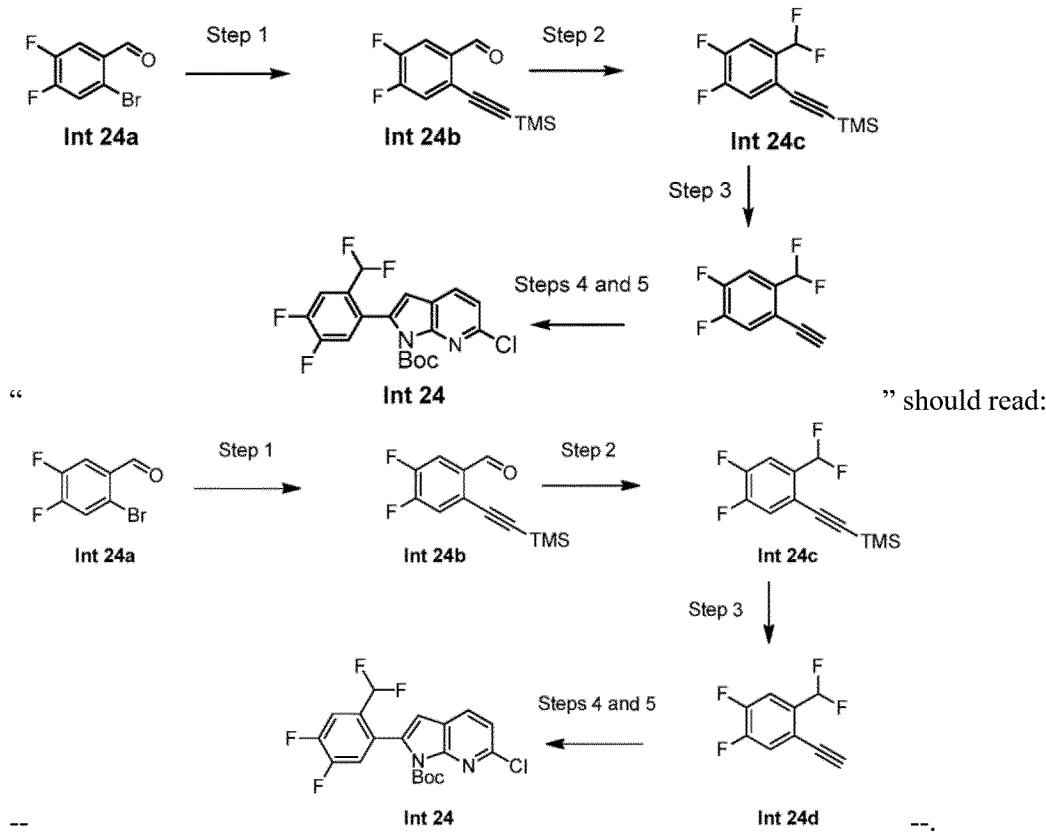" should read:

Column 60, Line 38:
"step 31-(difluorom-" should read: -- step 3 1-(difluorom- --.

Column 61, Line 22:
"Step 16-chloro-3-iodo-" should read: -- Step 1 6-chloro-3-iodo- --.

Column 61, Line 24:
"Step 31-ethynyl-2-(trifluorom-" should read: -- Step 3 1-ethynyl-2-(trifluorom- --.

Column 77, Line 1:
"1-Methyl-n$^5$-(2-(2-(trifluoromethyl)" should read: -- 1-Methyl-$N^5$-(2-(2-(trifluoromethyl) --.

Column 78, Line 18:
"step 16-chloro-1-methyly-2-(2-(trifluo-" should read: -- step 1 6-chloro-1-methyly-2-(2-(trifluo- --.